United States Patent
Chackalamannil et al.

(10) Patent No.: US 7,488,752 B2
(45) Date of Patent: Feb. 10, 2009

(54) THROMBIN RECEPTOR ANTAGONISTS

(75) Inventors: Samuel Chackalamannil, Califon, NJ (US); Mariappan V. Chelliah, Edison, NJ (US); Yan Xia, Edison, NJ (US); Keith A. Eagen, West Orange, NJ (US)

(73) Assignee: Schering Corporation, Kenilworth, NJ (US)

( * ) Notice: Subject to any disclaimer, the term of this patent is extended or adjusted under 35 U.S.C. 154(b) by 377 days.

(21) Appl. No.: 11/243,708

(22) Filed: Oct. 5, 2005

(65) Prior Publication Data

US 2006/0079684 A1    Apr. 13, 2006

Related U.S. Application Data

(60) Provisional application No. 60/617,514, filed on Oct. 8, 2004.

(51) Int. Cl.
| | | |
|---|---|---|
| A01N 43/08 | (2006.01) | |
| A61K 31/34 | (2006.01) | |
| C07D 307/00 | (2006.01) | |
| C07D 307/93 | (2006.01) | |
| C07D 407/00 | (2006.01) | |

(52) U.S. Cl. ...................... 514/469; 549/302
(58) Field of Classification Search ............... 549/302; 514/469

See application file for complete search history.

(56) References Cited

U.S. PATENT DOCUMENTS

| | | | |
|---|---|---|---|
| 6,063,847 | A | 5/2000 | Chackalamannil et al. |
| 6,326,380 | B1 | 12/2001 | Chackalamannil et al. |
| 6,645,987 | B2 | 11/2003 | Chackalamannil et al. |
| 7,037,920 | B2 | 5/2006 | Chackalamannil et al. |
| 2004/0152736 | A1 | 8/2004 | Chackalamannil et al. |

FOREIGN PATENT DOCUMENTS

| | | | |
|---|---|---|---|
| WO | | 0196330 | * 12/2001 |
| WO | WO 01/96330 A2 | | 12/2001 |

OTHER PUBLICATIONS

Bensaid et al., "The Cannabinoid $CB_1$ Receptor Antagonist SR141716 Increases Acrp30 mRNA Expression in Adipose Tissue of Obese fa/fa Rats and in Cultured Adipocyte Cells", Molecular Pharmacology, 63(4):908-914 (2003).
Bernatowicz et al., "Development of Potent Thrombin Receptor Antagonist Peptides", J. Med. Chem., 39:4879-4887 (1996).
Chackalamannil, "A Highly Efficient Total Synthesis of (+)-Himbacine", J. Am. Chem. Soc., 118:9812-9813 (1996).
Pertwee, "Pharmacology of Cannabinoid Receptor Ligands", Current Medicinal Chemistry, 6(8):635-664 (1999).
Wermuth, "Molecular Variations Based on Isosteric Replacements", The Practice of Medicinal Chemistry, pp. 203-237 (1996).
International Search Report for corresponding PCT Application No. PCT/US2005/035745 International Filing Date Jul. 19, 2006.

* cited by examiner

Primary Examiner—D. Margaret Seaman
Assistant Examiner—Niloofar Rahmani
(74) Attorney, Agent, or Firm—William Y. Lee; Serena Farquharson-Torres

(57) ABSTRACT

Heterocyclic-substituted tricyclics of the formula

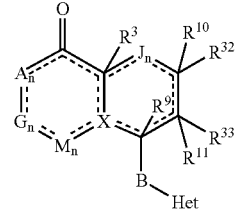

formula I or a pharmaceutically acceptable salt or solvate of said compound, isomer or racemic mixture wherein z,1 represents an optional double bond, the dotted line is optionally a bond or no bond, resulting in a double bond or a single bond, as permitted by the valency requirement and wherein A, B, G, M, X, J, n, Het, $R^3$, $R^{10}$, $R^{11}$, $R^{32}$ and $R^{33}$ are herein defined and the remaining substituents are as defined in the specification, are disclosed, as well as pharmaceutical compositions containing them and a method of treating diseases associated with thrombosis, atherosclerosis, restenosis, hypertension, angina pectoris, arrhythmia, heart failure, and cancer by administering said compounds. Combination therapy with other cardiovascular agents is also claimed.

25 Claims, No Drawings

THROMBIN RECEPTOR ANTAGONISTS

CROSS REFERENCE TO RELATED APPLICATIONS

This application claims the benefit of U.S. Provisional Application No. 60/617,514 filed on Oct. 8, 2004.

BACKGROUND OF THE INVENTION

The present invention relates to nor-seco himbacine derivatives, which can be useful as thrombin receptor antagonists in the treatment of diseases associated with thrombosis, atherosclerosis, restenosis, hypertension, angina pectoris, arrhythmia, heart failure, cerebral ischemia, stroke, neurodegenerative diseases and cancer. Thrombin receptor antagonists are also known as protease activated receptor-1 (PAR-1) antagonists. The compounds of the invention also can be useful as cannabinoid ($CB_2$) receptor inhibitors for the treatment of rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis. The invention also relates to pharmaceutical compositions comprising said compounds.

Thrombin is known to have a variety of activities in different cell types. Thrombin receptors are known to be present in such cell types as human platelets, vascular smooth muscle cells, endothelial cells and fibroblasts. It is therefore expected that thrombin receptor antagonists will be useful in the treatment of thrombotic, inflammatory, atherosclerotic and fibroproliferative disorders, as well as other disorders in which thrombin and its receptor play a pathological role.

Thrombin receptor antagonist peptides have been identified based on structure-activity studies involving substitutions of amino acids on thrombin receptors. In Bernatowicz et al., *J. Med. Chem.*, 39 (1996), p. 4879-4887, tetra- and pentapeptides are disclosed as being potent thrombin receptor antagonists, for example N-trans-cinnamoyl-p-fluoroPhe-p-guanidinoPhe-Leu-Arg-Arg-$NH_2$ and N-trans-cinnamoyl-p-fluoroPhe-p-guanidinoPhe-Leu-Arg-Arg-$NH_2$. Peptide thrombin receptor antagonists are also disclosed in WO 94/03479, published Feb. 17, 1994.

Cannabinoid receptors belong to the superfamily of G-protein coupled receptors. They are classified into the predominantly neuronal $CB_1$ receptors and the predominantly peripheral $CB_2$ receptors. These receptors exert their biological actions by modulating adenylate cyclase and $Ca^{+2}$ and $K^+$ currents. While the effects of $CB_1$ receptors are principally associated with the central nervous system, $CB_2$ receptors are believed to have peripheral effects related to bronchial constriction, immunomodulation and inflammation. As such, a selective $CB_2$ receptor binding agent is expected to have therapeutic utility in the control of diseases associated with rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis (R. G. Pertwee, *Curr. Med. Chem.* 6(8), (1999), 635; M. Bensaid, *Molecular Pharmacology*, 63 (4), (2003), 908.).

Himbacine, a piperidine alkaloid of the formula

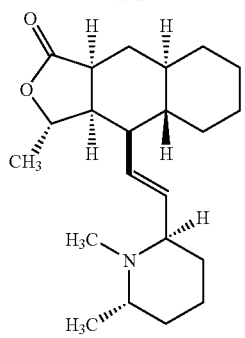

has been identified as a muscarinic receptor antagonist. The total synthesis of (+)-himbacine is disclosed in Chackalamannil et al., *J. Am. Chem. Soc.*, 118 (1996), p. 9812-9813.

Substituted tricyclic thrombin receptor antagonists are disclosed in U.S. Pat. No. 6,063,847, U.S. Pat. No. 6,326,380 and U.S. Ser. Nos. 09/880222 (WO 01/96330) and 10/271715.

SUMMARY OF THE INVENTION

The present invention relates to compounds represented by the formula I:

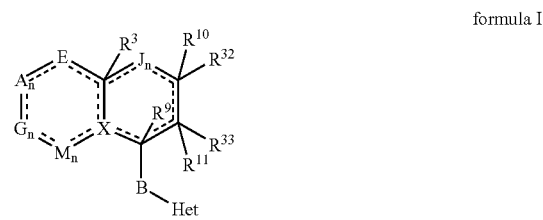

formula I or a pharmaceutically acceptable salt of said compound, wherein ===== represents a double bond or a single bond, as permitted by the valency requirement; with the proviso that $R^3$ is absent when the carbon to which $R^3$ would be attached is part of a double bond;

B is —$(CH_2)_{n3}$—, —$(CH_2)$—O—, —$(CH_2)$S—, —$(CH_2)$—$NR^6$—, —C(O)$NR^6$—, —$NR^6$C(O)—,

—$(CH_2)_{n4}CR^{12}$=$CR^{12a}(CH_2)_{n5}$— or —$(CH_2)_{n4}$C≡C($CH_2)_{n5}$— wherein $n_3$ is 0-5, $n_4$ and $n_5$ are independently 0-2, and $R^{12}$ and $R^{12a}$ are independently selected from the group consisting of hydrogen, alkyl and halogen;

E is

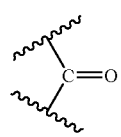

or —$S(O)_m$—, where m is 0, 1 or 2;

A, G, M and J are independently selected from the group consisting of —N(R$^{54}$)—, —(CR$^1$R$^2$)—, —O—,

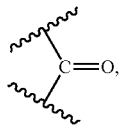

—S—, —S(O)—, —S(O)$_2$— and

X is

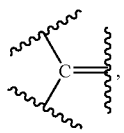

—CH— or —N—, with the proviso that selection of A, G, M and X do not result in adjacent oxygen or sulfur atoms;

each n is 0, 1 or 2 with the proviso that all n variables cannot be 0;

Het is a mono-, bi- or tricyclic heteroaromatic group of 5 to 14 atoms comprised of 1 to 13 carbon atoms and 1 to 4 heteroatoms independently selected from the group consisting of N, O and S, with the proviso that there are no adjacent oxygen or sulfur atoms present in the heteroaromatic group, wherein a ring nitrogen can form an N-oxide or a quaternary group with an alkyl group, wherein Het is attached to B by a carbon atom ring member, and wherein the Het group is substituted by 1 to 4 moieties, W, wherein each W is independently selected from the group consisting of hydrogen; alkyl; fluoroalkyl; difluoroalkyl; trifluoroalkyl; cycloalkyl; heterocycloalkyl; heterocycloalkyl substituted by alkyl or alkenyl; alkenyl; R$^{21}$-arylalkyl; R$^{21}$-aryl-alkenyl; heteroaryl; heteroarylalkyl; heteroarylalkenyl; hydroxyalkyl; dihydroxyalkyl; aminoalkyl; alkylaminoalkyl; di-(alkyl)-aminoalkyl; thioalkyl; alkoxy; alkenyloxy; halogen; —NR$^4$R$^5$; —CN; —OH; —C(O)OR$^{17}$; —COR$^{16}$; —OS(O$_2$)CF$_3$; —CH$_2$OCH$_2$CF$_3$; alkylthio; —C(O)NR$^4$R$^5$; —OCHR$^6$-phenyl; phenoxyalkyl; —NHCOR$^{16}$; —NHSO$_2$R$^{16}$; biphenyl; —OC(R$^6$)$_2$COOR$^7$; —OC(R$^6$)$_2$C(O)NR$^4$R$^5$; alkoxy substituted by alkyl, amino or —NHC(O)OR$^{17}$; aryl; aryl substituted by 1 to 3 substituents independently selected from the group consisting of alkyl, halogen, alkoxy, methylenedioxy, carboxylic acid, carboxamide, amine, urea, amide, sulfonamide, —CN, —CF$_3$, —OCF$_3$, —OH, alkylamino-, di-(alkyl) amino-, —NR$^{25}$R$^{26}$alkyl-, hydroxyalkyl-, —C(O)OR$^{17}$, —COR$^{17}$, —NHCOR$^{16}$, —NHS(O)$_2$R$^{16}$, —NHS(O)$_2$CH$_2$CF$_3$, —C(O)NR$^{25}$R$^{26}$, —NR$^{25}$—C(O)—NR$^{25}$R$^{26}$; —S(O)R$^{13}$, —S(O)R$^{13}$ and —SR$^{13}$; or alkyl optionally substituted with —NR$^1$R$^2$, —NR$^1$COR$^2$, —NR$^1$CONR$^1$R$^2$, —NR$^1$C(O)OR$^2$, —NR$^1$S(O)$_2$R$^2$, —NR$^1$S(O)$_2$NR$^1$R$^2$, —C(O)OH, —C(O)OR$^1$, —CONR$^1$R$^2$heteroaryl, hydroxyalkyl, alkyl or —S(O)$_2$-alkyl; —C(O)NR$^4$R$^5$ or heteroaryl; wherein adjacent carbons on the Het ring can optionally form a ring with a methylenedioxy group;

R$^1$ and R$^2$ are independently selected from the group consisting of hydrogen, alkyl, fluoroalkyl, difluoroalkyl, trifluoroalkyl, cycloalkyl, alkenyl, alkoxy, arylalkyl, arylalkenyl, heteroarylalkyl, heteroarylalkenyl, hydroxy, hydroxyalkyl, alkoxyalkyl, aminoalkyl, aryl and thioalkyl; or R$^1$ and R$^2$ when attached to nitrogen, taken together, form a mono or bicyclic heterocyclic ring of 4 to 10 atoms, with 1-3 heteroatoms selected from —O—, —N—, —S—, —S(O)—, —S(O)$_2$— and

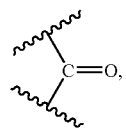

with the proviso that S and O ring atoms are not adjacent to each other, where said heterocyclic ring is unsubstituted or substituted with one or more groups selected from alkyl, halogen, hydroxy, alkoxy, aryloxy and arylalkoxy;

R$^3$ is aralkoxy, aryloxy, heteroaryl, heteroaralkoxy, —CN, —NO$_2$, —O-aryl, —O-heteroaryl, N$_3$, —C(O)NR$^{18}$R$^{19}$, —C(=NR$^1$)NR$^1$R$^2$, —N(R$^1$)C=(NR$^1$)NR$^1$R$^2$; —N=C (R$^1$)NR$^1$R$^2$, —NR$^{18}$C(O)R$^{19}$, —NR$^{18}$C(O)NR$^{18}$R$^{19}$, —NR$^{18}$C(O)OR$^{19}$, —NR$^{18}$S(O)$_2$R$^{19}$, —NR$^{18}$S(O)$_2$NR$^{18}$R$^{19}$, —NHNR$^{18}$R$^{19}$, —NR$^{18}$NR$^{18}$R$^{19}$ or -alkyl-NR$^{18}$R$^{19}$;

R$^6$ is hydrogen, alkyl or phenyl;

R$^7$ is hydrogen or alkyl;

each R$^{13}$ is independently selected from hydrogen, alkyl, cycloalkyl, haloalkyl, halogen, —(CH$_2$)$_{n6}$NHC(O)OR$^{16b}$, —(CH$_2$)$_{n6}$NHC(O)R$^{16b}$, —(CH$_2$)$_{n6}$NHC(O)NR$^4$R$^5$, —(CH$_2$)$_{n6}$NHSO$_2$R$^{16}$, —(CH$_2$)$_{n6}$NHSO$_2$NR$^4$R$^5$, and —(CH$_2$)$_{n6}$C(O)NR$^{28}$R$^{29}$, where n$_6$ is 0-4;

each R$^{14}$ is independently selected from the group consisting of hydrogen, alkyl, —OH, alkoxy, arylalkyl, heteroaryl, heteroarylalkyl, heterocyclyl, heterocyclylalkyl, halogen, haloalkyl, —(CH$_2$)$_{n6}$NHC(O)OR$^{16b}$; —(CH$_2$)$_{n6}$NHC(O) R$^{16b}$, —(CH$_2$)$_{n6}$NHC(O)NR$^4$R$^5$, —(CH$_2$)$_{n6}$NHSO$_2$R$^{16}$, —(CH$_2$)$_{n6}$NHSO$_2$NR$^4$R$^5$, and —(CH$_2$)$_{n6}$C(O)NR$^{28}$R$^{29}$ where n$_6$ is 0-4; where R$^4$ and R$^5$ are independently selected from the group consisting of hydrogen, alkyl, phenyl, benzyl and cycloalkyl, or R$^4$ and R$^5$ together can form a ring with the nitrogen to which they are attached, wherein said ring formed by R$^4$ and R$^5$ is optionally substituted with =O, OH, OR$^1$ or —C(O)OH; or R$^{13}$ and R$^{14}$ taken together form a spirocyclic or a heterospirocyclic ring of 3-6 ring atoms, wherein said heterospirocyclic ring contains 2 to 5 carbon ring atoms and 1 or 2 hetero ring atoms selected from the group consisting of O, S and N;

R$^{16}$ is independently selected from the group consisting of hydrogen, alkyl, phenyl and benzyl;

R$^{16a}$ is independently selected from the group consisting of hydrogen, alkyl, phenyl and benzyl;

R$^{16b}$ is hydrogen, alkoxy, alkyl, alkoxyalkyl-, R$^{22}$—O—C (O)-alkyl-, cycloalkyl, R$^{21}$-aryl, R$^{21}$-arylalkyl, haloalkyl, alkenyl, halo substituted alkenyl, alkynyl, halo substituted alkynyl, R$^{21}$-heteroaryl, (R$^{21}$-heteroaryl)-alkyl-, (R$^{21}$-heterocycloalkyl)-alkyl-, R$^{28}$R$^{29}$N-alkyl-, R$^{28}$R$^{29}$N—C(O)-alkyl-, R$^{28}$R$^{29}$N—C(O)O-alkyl-, R$^{28}$OC(O)N(R$^{29}$)-alkyl-, R$^{28}$S(O)$_2$N(R$^{29}$)-alkyl-, R$^{28}$R$^{29}$N—C(O)—N(R$^{29}$)-alkyl-, R$^{28}$R$^{29}$N—S(O)$_2$N(R$^{29}$)-alkyl-, R$^{28}$—C(O)N(R$^{29}$)-alkyl-, R$^{28}$R$^{29}$N—S(O)$_2$-alkyl-, HOS(O)$_2$-alkyl-, (OH)$_2$P(O)$_2$-alkyl-, R$^{28}$—S-alkyl-, R$^{28}$—S(O)$_2$-alkyl- or hydroxyalkyl;

$R^{17}$ is independently selected from the group consisting of hydrogen, alkyl, phenyl and benzyl;

$R^{18}$ and $R^{19}$ are hydrogen, alkyl, aryl, $R^{21}$-aryl, heteroaryl, cycloalkyl, heterocyclyl, alkoxyalkyl, haloalkoxyalkyl, aryloxyalkyl, arylalkoxyalkyl, heteroaryloxyalkyl, heteroarylalkoxyalkyl, cycloalkyloxyalkyl, (heterocyclyl)alkyloxyalkyl, alkoxyalkyloxyalkyl, —S(O)$_2$-alkyl, —C(NH)NR$^1$R$^2$ or alkyl substituted with one or two moieties selected from cycloalkyl, halogen, hydroxy, —NR$^1$R$^2$, —NR$^1$C(O)R$^2$, —NR$^1$C(O)NR$^1$R$^2$, —NR$^1$C(O)OR$^2$, —NR$^1$S(O)$_2$R$^2$, —NR$^1$S(O)$_2$NR$^1$R$^2$, —C(O)OH, —C(O)OR$^1$ and —C(O)NR$^1$R$^2$; or $R^{18}$ and $R^{19}$ together with the nitrogen to which they are attached, form a mono or bicyclic heterocyclic ring of 4 to 10 atoms, having 1-3 hetero ring atoms selected from —O—, —N—, —S—, —S(O)—, —S(O)$_2$— and

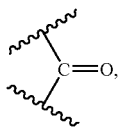

with the proviso that S and O atoms are not adjacent to each other, the ring being unsubstituted or substituted with one or more groups selected from alkyl, halogen, hydroxy, alkoxy, aryloxy, arylalkoxy, —NR$^1$R$^2$, —NR$^1$COR$^2$, —NR$^1$C(O)NR$^1$R$^2$, —NR$^1$C(O)OR$^2$, —NR$^1$S(O)$_2$R$^2$, —NR$^1$S(O)$_2$NR$^1$R$^2$, —C(O)OR$^1$, —CONR$^1$R$^2$ and alkyl substituted with —NR$^1$R$^2$, —NR$^1$COR$^2$, —NR$^1$CONR$^1$R$^2$, —NR$^1$C(O)OR$^2$, —NR$^1$S(O)$_2$R$^2$, —NR$^1$S(O)$_2$NR$^1$R$^2$, —C(O)OR$^1$ or —CONR$^1$R$^2$;

$R^{21}$ is 1 to 3 moieties and each $R^{21}$ is independently selected from the group consisting of hydrogen, —CN, —CF$_3$, —OCF$_3$, halogen, —NO$_2$, alkyl, —OH, alkoxy, alkylamino-, di-(alkyl)amino-, —NR$^{25}$R$^{26}$alkyl-, hydroxyalkyl-, —C(O)OR$^{17}$, —COR$^{17}$, —NHCOR$^{16}$, —NHS(O)$_2$R$^{16}$, —C(NH)—NH$_2$, —NHS(O)$_2$CH$_2$CF$_3$, —C(O)NR$^{25}$R$^{26}$, —NR$^{25}$—C(O)—NR$^{25}$R$^{26}$, —S(O)R$^{13}$, —S(O)$_2$R$^{13}$, —SR$^{13}$, —SO$_2$NR$^4$R$^5$ and —CONR$^4$R$^5$ and —CONR$^4$R$^5$; or two adjacent $R^{21}$ moieties can form a methylenedioxy group;

$R^{22}$ is hydrogen, alkyl, phenyl, benzyl, —COR$^{16}$, —CONR$^{18}$R$^{19}$, —COR$^{23}$, —S(O)R$^{31}$, —S(O)$_2$R$^{31}$, —S(O)$_2$NR$^{24}$R$^{25}$ or —C(O)OR$^{27}$; $R^{23}$ is

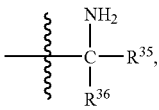

wherein $R^{35}$ and $R^{36}$ are independently selected from the group consisting of hydrogen, alkyl, and $R^{37}$-substituted alkyl, wherein $R^{37}$ is selected from the group consisting of HO—, HS—, CH$_2$S—, —NH$_2$, phenyl, p-hydroxyphenyl and indolyl; or $R^{23}$ is alkyl; haloalkyl; alkenyl; haloalkenyl; alkynyl; cycloalkyl; cycloalkylalkyl; cycloalkyl substituted by 1 to 3 substituents selected from the group consisting of alkoxyalkyl, alkyl, halogen, hydroxy, alkoxy, aryloxy, arylalkoxy, —NR$^1$R$^2$, —NR$^1$C(O)R$^2$, —NR$^1$C(O)NR$^1$R$^2$, —NR$^1$C(O)OR$^2$, —NR$^1$S(O)$_2$R$^2$, —NR$^1$S(O)$_2$NR$^1$R$^2$, —C(O)OH, —C(O)OR$^1$ and —CONR$^1$R$^2$; aryl; aralkyl; heteroaryl; heterocycloalkyl; alkyl substituted with —NR$^1$R$^2$, —NR$^1$COR$^2$, —NR$^1$CONR$^1$R$^2$, —NR$^1$C(O)OR$^2$—NR$^1$S(O)$_2$R$^2$, —NR$^1$S(O)$_2$NR$^1$R$^2$, —C(O)OH, —C(O)OR$^1$, —CONR$^1$R$^2$ and —SO$_3$H;

$R^{24}$, $R^{25}$ and $R^{25}$ are independently selected from the group consisting of hydrogen, alkyl, haloalkyl, alkenyl, alkynyl, aryl, aralkyl, cycloalkyl, halocycloalkyl, alkoxyalkyl, hydroxy and alkoxy;

$R^{27}$ is 1 to 3 moieties and each $R^{27}$ is selected from the group consisting of hydrogen, alkyl, and cycloalkyl, wherein $R^{27}$ is optionally substituted with —OH, —C(O)OH, halogen and alkoxy;

$R^{28}$ and $R^{29}$ are independently selected from the group consisting of hydrogen, alkyl, alkoxy, arylalkyl, heteroaryl, heteroarylalkyl, hydroxyalkyl, alkoxyalkyl, heterocyclyl, heterocyclylalkyl, and haloalkyl; or $R^{28}$ and $R^{29}$ taken together form a spirocyclic or a heterospirocyclic ring having 3-6 ring atoms;

$R^{32}$ and $R^{33}$ are independently selected from the group consisting of hydrogen, $R^{34}$-alkyl, $R^{34}$-alkenyl, $R^{34}$-alkynyl, $R^{40}$-heterocycloalkyl, $R^{38}$-aryl, $R^{38}$-aralkyl, $R^{42}$-cycloalkyl, $R^{42}$-cycloalkenyl, —OH, —OC(O)R$^{43}$, —C(O)OR$^{43}$, —C(O)R$^{43}$, —C(O)NR$^{43}$R$^{44}$, —NR$^{43}$R$^{44}$, —NR$^{43}$C(O)R$^{44}$, —NR$^{43}$C(O)NR$^{44}$R$^{45}$, —NHS(O)$_2$R$^{43}$, —OC(O)NR$^{43}$R$^{44}$, $R^{37}$-alkoxy, $R^{37}$-alkenyloxy, $R^{37}$-alkynyloxy, $R^{40}$-heterocycloalkyloxy, $R^{42}$-cycloalkyloxy, $R^{42}$-cyclo-alkenyloxy, $R^{42}$-cycloalkyl-NH—, —NHSO$_2$NHR$^{16}$ and —CH(=NOR$^{17}$);

or $R^{32}$ and $R^{33}$ can be combined to form a ring structure Q, below

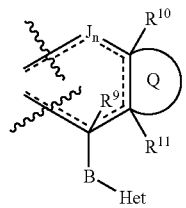

where $R^9$ is hydrogen, OH, alkoxy, halogen or haloalkyl;

Q is fused R-substituted aryl, R-substituted heteroaryl, R-substituted heterocyclic ring of 4-8 atoms containing 1-3 heteroatoms selected from O, S, S(O), S(O)$_2$ and NR$^{22}$ with the proviso that S and O cannot be adjacent to one another; or Q is

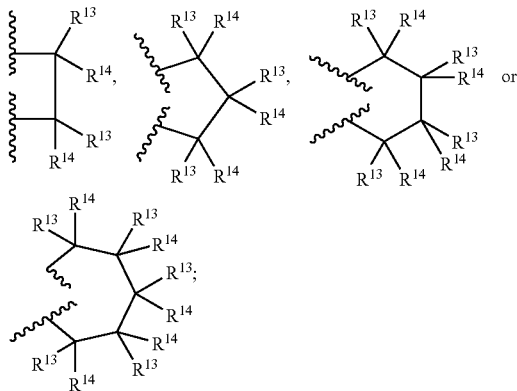

wherein $R^{10}$ and $R^{11}$ are independently selected from the group consisting of $R^1$ and —OR$^1$, provided that when ring Q is aromatic and the carbon atoms bearing $R^{10}$ and $R^{11}$ are connected by a double bond, $R^{10}$ and $R^{11}$ are absent;

R is 1 to 5 moieties and each R is independently selected from the group consisting of hydrogen, alkyl, halogen, hydroxy, amino, alkylamino, dialkylamino, alkoxy, —$COR^{16}$, —$C(O)OR^{17}$, —$C(O)NR^4R^5$, —$SOR^{16}$, —$S(O_2)R^{16}$, —$NR^6COR^{16a}$, —$NR^{16}C(O)OR^{16a}$, —$NR^{16}CONR^4R^5$, —$NR^{16}S(O_2)NR^4R^5$, fluoroalkyl, difluoroalkyl, trifluoroalkyl, cycloalkyl, alkenyl, arylalkyl, arylalkenyl, heteroarylalkyl, heteroarylalkenyl, hydroxyalkyl, aminoalkyl, aryl and thioalkyl;

$R^{34}$ is 1 to 3 moieties and each $R^{34}$ is independently selected from the group consisting of hydrogen, halogen, —OH, alkoxy, $R^{47}$-aryl, alkyl-$C(O)$—, alkenyl-$C(O)$—, alkynyl-$C(O)$—, heterocycloalkyl, $R^{39}$-cycloalkyl, $R^{39}$-cycloalkenyl, —$OC(O)R^{43}$, —$C(O)OR^{43}$, —$C(O)R^{43}$, —$C(O)NR^{43}R^{44}$, —$NR^{43}R^{44}$, —$NR^{43}C(O)R^{44}$, —$NR^{43}C(O)NR^{44}R^{45}$, —$NHSO_2R^{43}$, —$OC(O)NR^{43}R^{44}$, $R^{34}$-alkenyloxy, $R^{34}$-alkynyloxy, $R^{40}$-heterocycloalkyloxy, $R^{42}$-cycloalkyloxy, $R^{42}$-cycloalkenyloxy, $R^{42}$-cycloalkyl-NH—, —$NHSO_2NHR^{16}$ and —$CH(=NOR^{17})$;

$R^{38}$ is 1 to 3 moieties and each $R^{38}$ is independently selected from the group consisting of hydrogen, heterocycloalkyl, halogen, —$C(O)OR^{48}$, —CN, —$C(O)NR^{49}R^{50}$, —$NR^{51}C(O)R^{52}$, —$OR^{48}$, cycloalkyl, cycloalkylalkyl, alkylcycloalkylalkyl, haloalkylcycloalkylalkyl, hydroxyalkyl, alkoxyalkyl, and $R^{52}$-heteroaryl; or two $R^{38}$ groups on adjacent ring carbons form a fused methylenedioxy group;

$R^{39}$ is 1 to 3 moieties and each $R^{39}$ is independently selected from the group consisting of hydrogen, halogen and alkoxy;

$R^{40}$ is 1 to 3 moieties and each $R^{40}$ is independently selected from the group consisting of hydrogen, $R^{41}$-alkyl, $R^{41}$-alkenyl and $R^{41}$-alkynyl;

$R^{41}$ is hydrogen, —OH or alkoxy;

$R^{42}$ is 1 to 3 moieties and each $R^{42}$ is independently selected from the group consisting of hydrogen, alkyl, —OH, alkoxy and halogen;

$R^{43}$, $R^{44}$ and $R^{45}$ are independently selected from the group consisting of hydrogen, alkyl, alkoxyalkyl, $R^{38}$-arylalkyl, $R^{46}$-cycloalkyl, $R^{53}$-cycloalkylalkyl, $R^{38}$-aryl, heterocycloalkyl, heteroaryl, heterocycloalkylalkyl and heteroarylalkyl;

$R^{46}$ is hydrogen, alkyl, hydroxyalkyl or alkoxy;

$R^{47}$ is 1 to 3 moieties and each $R^{47}$ is independently selected from the group consisting of hydrogen, alkyl, —OH, halogen, —CN, alkoxy, trihaloalkoxy, alkylamino, di(alkyl)amino, —$OCF_3$, hydroxyalkyl, —CHO, —$C(O)$alkylamino, —$C(O)$di(alkyl)amino, —$NH_2$, —$NHC(O)$alkyl and —$N(alkyl)C(O)$alkyl;

$R^{48}$ is hydrogen, alkyl, haloalkyl, dihaloalkyl or trifluoroalkyl;

$R^{49}$ and $R^{50}$ are independently selected from the group consisting of hydrogen, alkyl, aralkyl, phenyl and cycloalkyl, or $R^{49}$ and $R^{50}$ together are —$(CH_2)_4$—, —$(CH_2)_5$— or —$(CH_2)_2$—$NR^{39}$—$(CH_2)_2$— and form a ring with the nitrogen to which they are attached;

$R^{51}$ and $R^{52}$ are independently selected from the group consisting of hydrogen, alkyl, aralkyl, phenyl and cycloalkyl, or $R^{51}$ and $R^{52}$ in the group —$NR^{39}C(O)R^{40}$, together with the nitrogen atoms to which they are attached, form a cyclic lactam having 5-8 ring members;

$R^{53}$ is hydrogen, alkoxy, —$SOR^{16}$, —$SO_2R^{17}$, —$C(O)OR^{17}$, —$C(O)NR^{18}R^{19}$, alkyl, halogen, fluoroalkyl, difluoroalkyl, trifluoroalkyl, cycloalkyl, alkenyl, aralkyl, arylalkenyl, heteroarylalkyl, heteroarylalkenyl, hydroxyalkyl, aminoalkyl, aryl, thioalkyl, alkoxyalkyl or alkylaminoalkyl, and $R^{54}$ is selected from the group consisting of hydrogen; alkyl; fluoroalkyl; difluoroalkyl; trifluoroalkyl; cycloalkyl; cycloalkyl substituted by 1 to 3 substituents selected from the group consisting of alkoxyalkyl, alkyl, halogen, hydroxy, alkoxy, aryloxy, arylalkoxy, —$NR^1R^2$, —$NR^1C(O)R^2$, —$NR^1C(O)NR^1R^2$, —$NRC(O)OR^2$, —$NR^1S(O)_2R^2$, —$NR^1S(O)_2NR^1R^2$, —$C(O)OH$, —$C(O)OR^1$ and —$CONR^1R^2$; alkenyl; alkoxy; arylalkyl; arylalkenyl; heteroarylalkyl; heteroarylalkenyl; hydroxy; alkoxy; hydroxyalkyl; alkoxyalkyl; aminoalkyl; aryl; heteroaryl; thioalkyl and alkyl substituted by 1 to 3 subsituents selected from the group consisting of urea, sulfonamide, carboxamide, carboxylic acid, carboxylic ester and sulfonyl urea;

and pharmaceutically acceptable salts thereof.

Pharmaceutical compositions comprising at least one compound of formula I and a pharmaceutically acceptable carrier are also provided. The compounds of the present invention can be useful as Thrombin receptor antagonists or PAR-1 antagonists for the treatment of a cardiovascular or circulatory disease or condition, an inflammatory disease or condition, a respiratory tract or disease or condition, cancer, acute renal failure, astrogliosis, a fibrotic disorder of the liver, kidney, lung or intestinal tract, Alzheimer's disease, diabetes, diabetic neuropathy, rheumatoid arthritis, neurodegenerative disease, neurotoxic disease, systemic lupus erythematosus, multiple sclerosis, osteoporosis, glaucoma, macular degeneration, psoriasis, radiation fibrosis, endothelial dysfunction, a wound or a spinal cord injury, or a symptom or result thereof.

Thrombin receptor antagonist compounds of the present invention can have anti-thrombotic, anti-platelet aggregation, anti-atherosclerotic, anti-restenotic and/or anti-coagulant activity. Thrombosis-related diseases treated by the compounds of this invention include thrombosis, atherosclerosis, restenosis, hypertension, angina pectoris, arrhythmia, heart failure, myocardial infarction, glomerulonephritis, thrombotic and thromboembolytic stroke, peripheral vascular diseases, other cardiovascular diseases, cerebral ischemia, inflammatory disorders and cancer, as well as other disorders in which thrombin and its receptor play a pathological role.

Certain embodiments of this invention also relate to a method of using at least one compound of Formula I in combination with one or more additional cardiovascular agents. Such combinations can be useful for the treatment of thrombosis, atherosclerosis, restenosis, hypertension, angina pectoris, angiogenesis related disorders, arrhythmia, a cardiovascular or circulatory disease or condition, heart failure, myocardial infarction, glomerulonephritis, thrombotic stroke, thromboembolytic stroke, peripheral vascular diseases, cerebral ischemia, rheumatoid arthritis, rheumatism, astrogliosis, a fibrotic disorder of the liver, kidney, lung or intestinal tract, systemic lupus erythematosus, multiple sclerosis, osteoporosis, glomerulonephritis, renal disease, acute renal failure, chronic renal failure, renal vascular homeostasis, renal ischemia, bladder inflammation, diabetes, diabetic neuropathy, cerebral stroke, cerebral ischemia, nephritis, cancer, melanoma, renal cell carcinoma, neuropathy and/or malignant tumors, neurodegenerative and/or neurotoxic diseases, conditions, or injuries, inflammation, asthma, glaucoma, macular degeneration, psoriasis, endothelial dysfunction disorders of the liver, kidney or lung inflammatory disorders of the lungs and gastrointestinal tract, respiratory tract disease or condition, radiation fibrosis, endothelial dysfunction, periodontal diseases or wounds or a spinal cord injury, or a symptom or result thereof. It is contemplated that a combination of this invention may be useful in treating more than one of the diseases listed.

Pharmaceutical compositions comprising a therapeutically effective amount of a combination of at least one compound of formula I and at least one additional cardiovascular agent in a pharmaceutically acceptable carrier are also provided.

An embodiment of the invention relate to the use of a thrombin receptor antagonist disclosed in any of U.S. Pat. No. 6,063,847, U.S. Pat. No. 6,326,380, U.S. Pat. No. 6,645,987, U.S. Ser. No. 10/271,715, all of which are incorporated herein by reference, in combination with one or more additional cardiovascular agents, for the treatment of thrombosis, platelet aggregation, coagulation, cancer, inflammatory diseases or respiratory diseases. In particular, the present invention relates to a method of using said combination in the treatment of thrombosis, atherosclerosis, restenosis, hypertension, angina pectoris, angiogenesis related disorders, arrhythmia, a cardiovascular or circulatory disease or condition, heart failure, myocardial infarction, glomerulonephritis, thrombotic stroke, thromboembolytic stroke, peripheral vascular diseases, cerebral ischemia, rheumatoid arthritis, rheumatism, astrogliosis, a fibrotic disorder of the liver, kidney, lung or intestinal tract, systemic lupus erythematosus, multiple sclerosis, osteoporosis, glomerulonephritis, renal disease, acute renal failure, chronic renal failure, renal vascular homeostasis, renal ischemia, bladder inflammation, diabetes, diabetic neuropathy, cerebral stroke, cerebral ischemia, nephritis, cancer, melanoma, renal cell carcinoma, neuropathy and/or malignant tumors, neurodegenerative and/or neurotoxic diseases, conditions, or injuries, inflammation, asthma, glaucoma, macular degeneration, psoriasis, endothelial dysfunction disorders of the liver, kidney or lung inflammatory disorders of the lungs and gastrointestinal tract, respiratory tract disease or condition, radiation fibrosis, endothelial dysfunction, periodontal diseases or wounds or a spinal cord injury, or a symptom or result thereof. Pharmaceutical compositions comprising a thrombin receptor antagonist disclosed in any of U.S. Pat. No. 6,063,847, U.S. Pat. No. 6,326,380, U.S. Pat. No. 6,645,987, U.S. Ser. No. 10/271715, and a cardiovascular agent with a pharmaceutically acceptable carrier are provided.

It is further contemplated that the combination of the invention can be provided as a kit comprising in a single package at least one compound of formula I in a pharmaceutical composition, and at least one separate pharmaceutical composition comprising a cardiovascular agent.

DETAILED DESCRIPTION

In one embodiment, the present invention provides compounds represented by structural formula I, or pharmaceutically acceptable salt thereof, wherein the various moieties are as described as above.

For compounds of Formula I, preferred embodiments of the compounds of formula I are as follows:

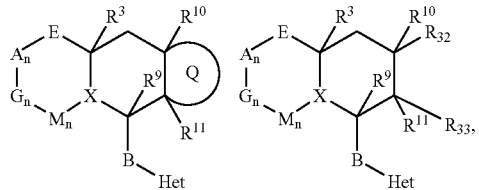

where X is —CH— or —N—.

Additional preferred embodiments of the compounds of formula I are as follows:

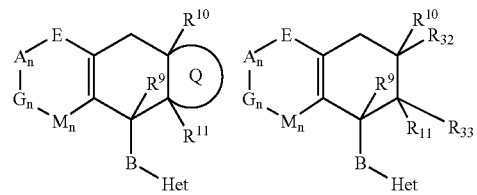

More preferred embodiments of formula I are as follows:

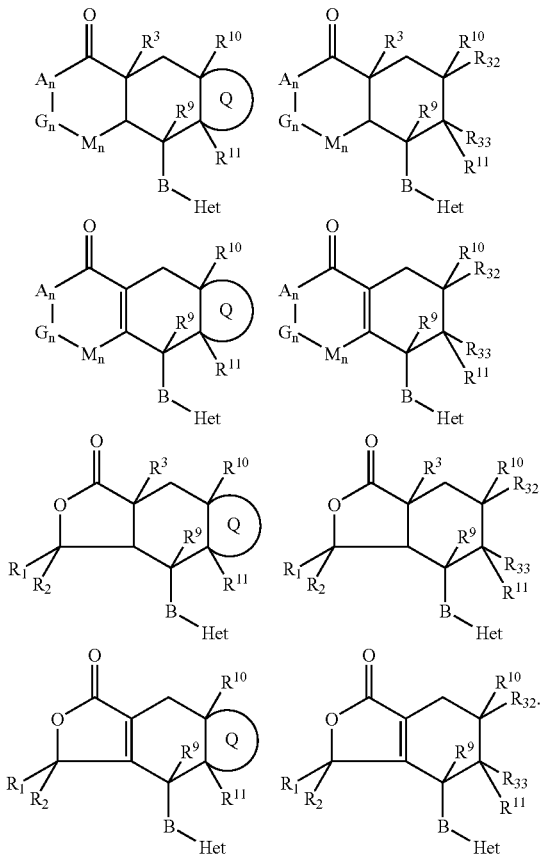

More preferred embodiments of formula I are as follows:

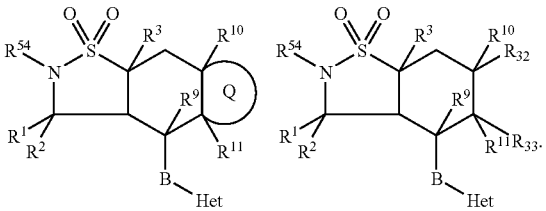

In one embodiment of a compound of formula I, $R^3$ is absent and a double bond is present between X and the carbon where $R^3$ is otherwise attached.

In an embodiment of a compound of formula I, $R^{32}$ and $R^{33}$ are combined to form the ring Q.

In another embodiment of a compound of formula I, A is O.

In another embodiment of a compound of formula I, for $A_n$, n is 1.

In another embodiment of a compound of formula I, for $M_n$, n is 0.

In another embodiment of a compound of formula I, G is —$CR^1R^2$—.

In another embodiment of a compound of formula I, wherein $R^1$ is hydrogen and $R^2$ is methyl.

In an embodiment of a compound of formula I, J is —$CR^1R^2$—.

In another embodiment of a compound of formula I, for $J_n$, n is 1.

In another embodiment of a compound of formula I, X is CH.

In another embodiment of a compound of formula I, B is —$(CH_2)_{n4}CR^{12}$=$CR^{12a}(CH_2)_{n5}$—, where $n_4$ and $n_5$ are 0.

In another embodiment of a compound of formula I, $R^3$ is heteroaryl, —$C(O)NR^{18}R^{19}$, —$NR^{18}C(O)R^{19}$, —$NR^{18}C(O)OR^{19}$, —$NR^{18}S(O)_2R^{19}$ or —$NR^{18}C(O)NR^{18}R^{19}$.

In another embodiment of a compound of formula I, $R^{18}$ and $R^{19}$ are hydrogen, alkyl, heteroaryl, —C(NH)—$NH_2$, aryl, $R^{21}$-aryl, or alkyl substituted with one or two moieties selected from cycloalkyl, halogen, hydroxy, —$NR^1R^2$, —$NR^1C(O)R^2$, —$NR^1C(O)NR^1R^2$, —$NR^1C(O)OR^2$, —$NR^1S(O)_2R^2$, —$NR^1S(O)_2NR^1R^2$, —C(O)OH, —$C(O)OR^1$ or —$C(O)NR^1R^2$; where $R^1$ and $R^2$ are hydrogen, alkyl or alkoxy; or $R^{18}$ and $R^{19}$ together with the nitrogen to which they are attached, form a mono or bicyclic heterocyclic ring of 4 to 10 atoms, with 1-3 heteroatoms selected from O, N, S, S(O), $S(O)_2$ and C=O, with the proviso that the S or O atom are not adjacent to each other, unsubstituted or substituted with one or more groups selected from alkyl, halogen, hydroxy, alkoxy, aryloxy, arylalkoxy, —$NR^1R^2$, —$NR^1COR^2$, —$NR^1C(O)NR^1R^2$, —$NR^1C(O)OR^2$, —$NR^1S(O_2)NR^1R^2$, —C(O)OH, —$C(O)OR^1$, —$CONR^1R^2$ and alkyl optionally substituted with —$NR^1R^2$, —$NR^1COR^2$, —$NR^1CONR^1R^2$, —$NR^1C(O)OR^2$, —$NR^1S(O)_2R^2$, —$NR^1S(O)_2NR^1R_2$, —C(O)OH, —$C(O)OR^1$ or —$CONR^1R^2$.

In another embodiment of a compound of formula I, Het is heteroaryl.

In another embodiment of a compound of formula I, W is aryl, heteroaryl or aryl substituted by halogen or —CN.

In another embodiment of a compound of formula I, $R^{32}$ and $R^{33}$ are hydrogen or alkyl or $R^{32}$ and $R^{33}$ are combined to form a ring structure Q, where Q is

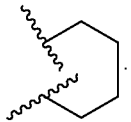

In an additional embodiment of a compound of formula I, B is cis or trans —$(CH_2)_{n4}CR^{12}$=$CR^{12a}(CH_2)_{n5}$—, where $n_4$ and $n_5$ are 0;

A, is O where n is 1;
$G_n$ is $CH_2$, CH(alkyl) or C(alkyl)$_2$;
X is —CH—
$J_n$ is $CH_2$ where n is 1;
$R^3$ is —$C(O)NR^{18}R^{19}$;
$R^{10}$ and $R^{11}$ are hydrogen;

R18 and $R^{19}$ are hydrogen, alkyl, heteroaryl, —C(NH)—$NH_2$, aryl, $R^{21}$-aryl, or alkyl substituted with one or two moieties selected from cycloalkyl, halogen, hydroxy, —$NR^1R^2$, —$NR^1C(O)R^2$, —$NR^1C(O)NR^1R^2$, —$NR^1C(O)OR^2$, —$NR^1S(O)_2R^2$, —$NR^1S(O)_2NR^1R^2$, —C(O)OH, —$C(O)OR^1$ or —$C(O)NR^1R^2$; where $R^1$ and $R^2$ are hydrogen, alkyl or alkoxy; or $R^{18}$ and $R^{19}$ together with the nitrogen to which they are attached, form a mono or bicyclic heterocyclic ring of 4 to 10 atoms, with 1-3 heteroatoms selected from O, N, S, S(O), $S(O)_2$ and C=O, with the proviso that the S or O atom are not adjacent to each other, unsubstituted or substituted with one or more groups selected from alkyl, halogen, hydroxy, alkoxy, aryloxy, arylalkoxy, —$NR^1R^2$, —$NR^1COR^2$, —$NR^1C(O)NR^1R^2$, —$NR^1C(O)OR^2$, —$NR^1S(O)_2R^2$, —$NR^1S(O_2)NR^1R^2$, —C(O)OH, —$C(O)OR^1$, —$CONR^1R^2$ and alkyl optionally substituted with —$NR^1R^2$, —$NR^1COR^2$, —$NR^1CONR^1R^2$, —$NR^1C(O)OR^2$, —$NR^1S(O)_2R^2$, —$NR^1S(O)_2NR^1R_2$, —C(O)OH, —$C(O)OR^1$ or —$CONR^1R^2$;

Het is heteroaryl;

W is aryl, heteroaryl or aryl substituted by halogen or —CN; and $R^{32}$ and $R^{33}$ are hydrogen or alkyl or $R^{32}$ and $R^{33}$ are optionally combined to form a ring structure Q, where Q is

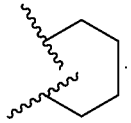

In an additional embodiment of a compound of formula I, B is —CH=CH—;

Het is heteroaryl substituted with W;

W is aryl substituted with halogen or CN;

$R^{32}$ and $R^{33}$ are combined to form Q and Q is

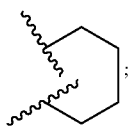

and $R^3$ is defined as follows:

| $R^3$ |
|---|
| 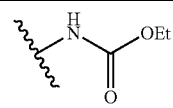 |
| 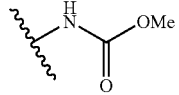 |

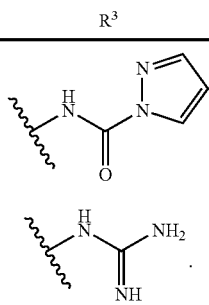

In an additional embodiment of a compound of formula I, B is cis or trans —$(CH_2)_{n4}CR^{12}=CR^{12a}(CH_2)_{n5}$ where $n_4$ and $n_5$ are 0;

$A_n$ is O where n is 1;

$G_n$ is $CH_2$, CH(alkyl) or C(alkyl)$_2$;

X is —CH—;

$J_n$ is $CH_2$ where n is 1;

$R^3$ is heteroaryl, —$NR^{18}C(O)R^{19}$, —$NR^{18}C(O)OR^{19}$ or —$NR^{18}S(O)_2R^{19}$;

$R^{10}$ and $R^{11}$ are hydrogen;

$R^{18}$ and $R^{19}$ are hydrogen, alkyl, heteroaryl, heterocyclyl, —C(NH)—$NH_2$, aryl, $R^{21}$, aryl, or alkyl substituted with one or two moieties selected from cycloalkyl, halogen, hydroxy, —$NR^1R^2$, —$NR^1C(O)R^2$, —$NR^1C(O)NR^1R^2$, —$NR^1C(O)OR^2$, —$NR^1S(O)_2R^2$, —$NR^1S(O)_2NR^1R^2$, —C(O)OH, —$C(O)OR^1$ or —$C(O)NR^1R^2$; where $R^1$ and $R^2$ are hydrogen, alkyl or alkoxy; or $R^{18}$ and $R^{19}$ together with the nitrogen to which they are attached, form a mono or bicyclic heterocyclic ring of 4 to 10 atoms, with 1-3 heteroatoms selected from O, N, S, S(O), S(O)$_2$ and C=O, with the proviso that the S or O atom are not adjacent to each other, unsubstituted or substituted with one or more groups selected from alkyl, halogen, hydroxy, alkoxy, aryloxy, arylalkoxy, —$NR^1R^2$, —$NR^1COR^2$, —$NR^1C(O)NR^1R^2$, —$NR^1C(O)OR^2$, —$NR^1S(O)_2R^2$, —$NR^1S(O_2)NR^1R^2$, —C(O)OH, —$C(O)OR^1$, —$CONR^1R^2$ and alkyl optionally substituted with —$NR^1R^2$, —$NR^1COR^2$, —$NR^1CONR^1R^2$, —$NR^1C(O)OR^2$, —$NR^1S(O)_2R^2$, —$NR^1S(O)_2NR^1R^2$, —C(O)OH, —$C(O)OR^1$ or —$CONR^1R^2$;

Het is heteroaryl;

W is aryl, heteroaryl or aryl substituted by halogen or —CN; and $R^{32}$ and $R^{33}$ are hydrogen or alkyl or $R^{32}$ and $R^{33}$ are optionally combined to form a ring structure Q, where Q is

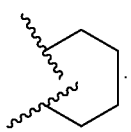

In an additional embodiment of a compound of formula I, B is —CH=CH—;

Het is heteroaryl substituted with W;

W is aryl substituted with halogen;

$R^{32}$ and $R^{33}$ are combined to form Q and Q is

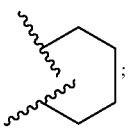

and $R^3$ is defined as follows:

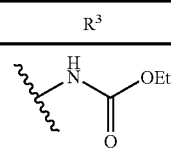

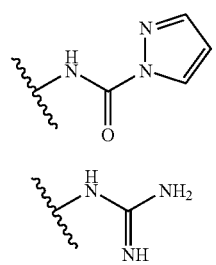

In an additional embodiment of a compound of formula I, B is cis or trans —$(CH_2)_{n4}CR^{12}=CR^{12a}(CH_2)_{n5}$, where $n_4$ and $n_5$ are 0;

$A_n$ is O where n is 1;

$G_n$ is $CR^1R^2$ where n is 1, where $R^1$ and $R^2$ are alkyl or hydrogen;

X is —CH—;

$J_n$ is $CR^1R^2$ where n is 1, where $R^1$ and $R^2$ are hydrogen;

$R^3$ is heteroaryl, heteroarylalkyl, —O-aryl, $N_3$, —$NR^{18}C(O)OR^{19}$, —$NR^{18}COR^{19}$, —$NHNR^{18}R^{19}$, —$NR^{18}S(O)_2R^{19}$, —$NR^{18}C(O)NR^{18}R^{19}$ or —$NR^{18}NR^{19}$;

$R^9$, $R^{10}$ and $R^{11}$ are hydrogen;

$R^{18}$ is hydrogen;

$R^{19}$ is O-alkyl or $NH_2$;

Het is a heteroaryl;

W is aryl substituted by 1 to 3 substituents independently selected from the group consisting of halogen, —$CF_3$, CN, alkyl, alkoxy and —$C(O)OR^{17}$; and $R^{32}$ and $R^{33}$ are alkyl or $R^{32}$ and $R^{33}$ and with the carbons to which they are attached, are combined to form Q.

In another embodiment of a compound of formula I, Q is cycloalkyl, preferably Q is cyclohexyl.

In another embodiment of a compound of formula I, W is phenyl substituted with halogen or CN.

In another embodiment of a compound of formula I, said halogen is F.

In another embodiment of a compound of formula I, R³ is —NHC(O)O-ethyl, —C(O)NHCH₂CH₂OH, —NHC(NH)—NH₂, N₃, —O-phenyl or

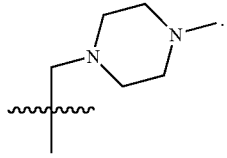

An inventive group of compounds is selected from the group consisting of:

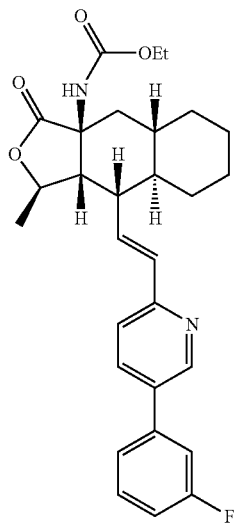

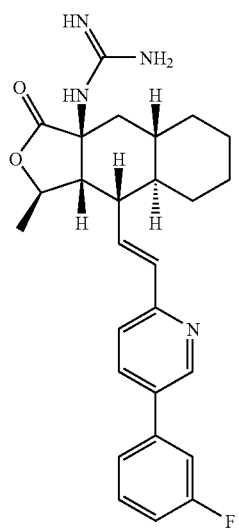

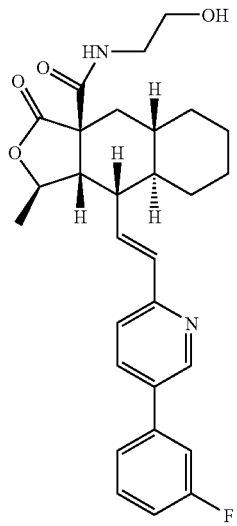

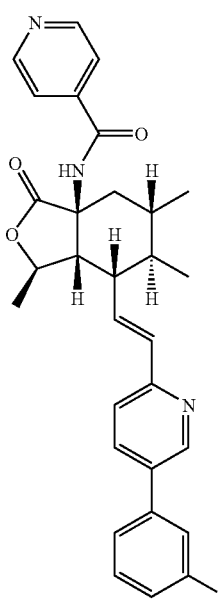

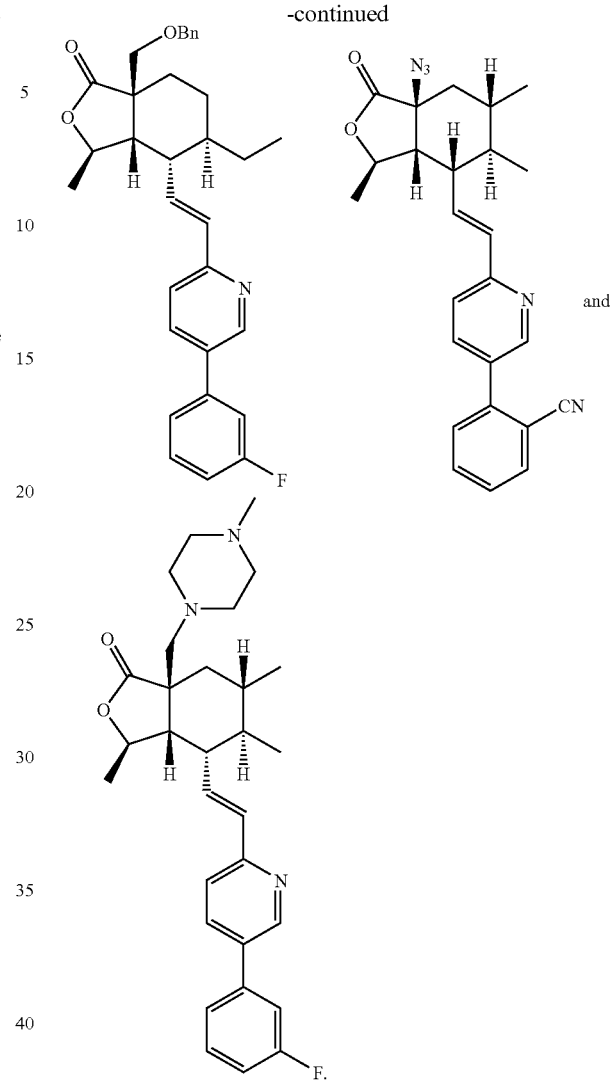

In another embodiment of a compound of formula I, a compound of the following structure

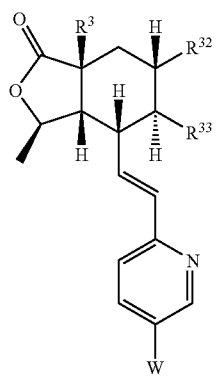

wherein R³, R³² and R³³ are herein defined.

In another embodiment of a compound of formula I, a compound of the following structure

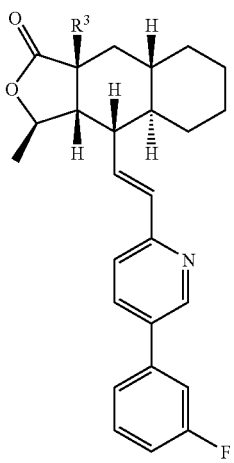

wherein $R^3$ is herein defined.

In another embodiment of a compound of formula I, B is cis or trans $-(CH_2)_{n4}CR^{12}=CR^{12a}(CH_2)_{n5}$, where $n_4$ and $n_5$ are 0;

$A_n$ is O where n is 1;

$G_n$ is $CR^1R^2$ where n is 1, where $R^1$ and $R^2$ are alkyl or hydrogen;

$J_n$ is $CR^1R^2$ where n is 1, where $R^1$ and $R^2$ are hydrogen;

$R^9$, $R^{10}$ and $R^{11}$ are hydrogen;

Het is a heteroaryl;

W is aryl substituted by 1 to 3 substituents independently selected from the group consisting of halogen, $-CF_3$, CN, alkyl, alkoxy and $-C(O)OR^{17}$; and $R^{32}$ and $R^{33}$ are alkyl or $R^{32}$ and $R^{33}$ and with the carbons to which they are attached, are combined to form Q.

In another embodiment of a compound of formula I, a compound of the following structure

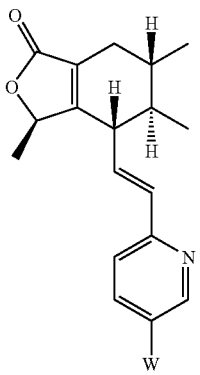

wherein W is

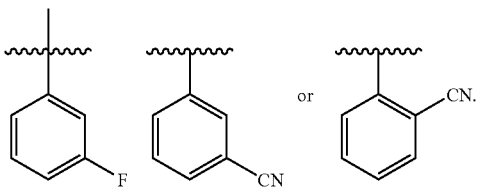

In another embodiment of a compound of formula I, a compound of the following structure

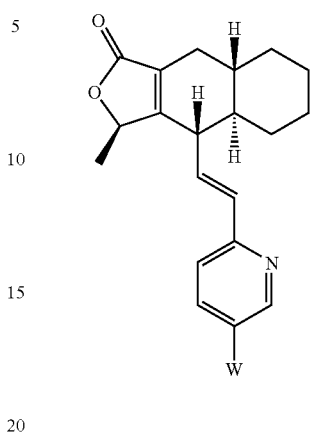

wherein W is

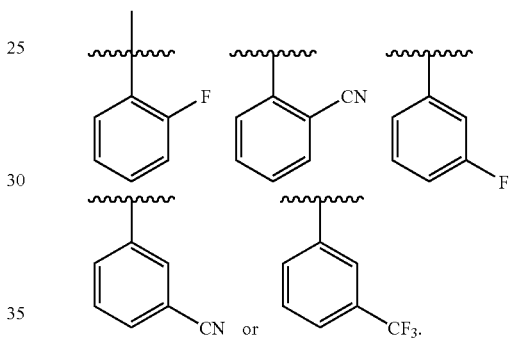

As used above, and throughout this disclosure, the following terms, unless otherwise indicated, shall be understood to have the following meanings:

"Patient" includes both human and animals.

"Subject" includes both mammals and non-mammalian animals.

"Mammal" means humans and other mammalian animals.

The following definitions apply regardless of whether a term is used by itself or in combination with other terms, unless otherwise indicated. Therefore, the definition of "alkyl" applies to "alkyl" as well as the "alkyl" portions of "hydroxyalkyl", "haloalkyl", "alkoxy", etc.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, $-NH$(alkyl), $-NH$(cycloalkyl), $-N$(alkyl)$_2$, carboxy and $-C(O)$O-alkyl. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Alkenyl" means an aliphatic hydrocarbon group (straight or branched carbon chain) comprising one or more double bonds in the chain and which can be conjugated or unconjugated. Useful alkenyl groups can comprise 2 to about 15 carbon atoms in the chain, preferably 2 to about 12 carbon atoms in the chain, and more preferably 2 to about 6 carbon atoms in the chain. The alkenyl group can be substituted by one or more substituents independently selected from the group consisting of halo, alkyl, aryl, cycloalkyl, cyano and alkoxy. Non-limiting examples of suitable alkenyl groups include ethenyl, propenyl, n-butenyl, 3-methylbut-enyl and n-pentenyl.

Where an alkyl or alkenyl chain joins two other variables and is therefore bivalent, the terms alkylene and alkenylene, respectively, are used.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl, naphthyl, indenyl, tetrahydronaphthyl and indanyl. "Arylene" means a bivalent phenyl group, including ortho, meta and para-substitution.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

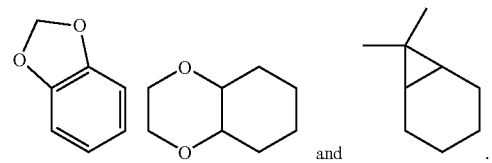

and

The term "Boc" refers to N-tert-butoxycarbonyl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclobutyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Cycloalkylene" refers to a corresponding bivalent ring, wherein the points of attachment to other groups include all positional isomers.

"Dihydroxyalkyl" refers to an alkyl chain substituted by two hydroxy groups on two different carbon atoms.

"Fluoroalkyl", "difluoroalkyl" and "trifluoroalkyl" mean alkyl chains wherein the terminal carbon is substituted by 1, 2 or 3 fluoroatoms, respectively, e.g., —CF$_3$, —CH$_2$CF$_3$, —CH$_2$CHF$_2$ or —CH$_2$CH$_2$F.

"Halo" refers to fluorine, chlorine, bromine or iodine radicals. Preferred are fluoro, chloro or bromo, and more preferred are fluoro and chloro.

"Halogen" means fluorine, chlorine, bromine, or iodine. Preferred are fluorine, chlorine and bromine.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination, provided that the rings do not include adjacent oxygen and/or sulfur atoms. N-oxides of the ring nitrogens are also included, as well as compounds wherein a ring nitrogen is substituted by an alkyl group to form a quaternary amine. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, oxadiazolyl, tetrazolyl, pyrimidyl, furazanyl, pyrrolyl, pyrazolyl, triazolyl, 1,2,4-thiadiazolyl, pyrazinyl, pyridazinyl, quinoxalinyl, phthalazinyl, oxindolyl, naphthyridyl (e.g., 1, 5 or 1,7), pyrido[2,3]imidazolyl, imidazo[1,2-a]pyridinyl, imidazo[2,1-b]thiazolyl, benzofuranyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzoxazolyl, benzothiazolyl, pyridopyrimidinyl, 7-azaindolyl and the like. The term "heteroaryl" also refers to partially saturated heteroaryl moieties such as, for example, tetrahydroisoquinolyl, tetrahydroquinolyl and the like. All positional isomers are contemplated, e.g., 2-pyridyl, 3-pyridyl and 4-pyridyl.

The term "Het" is exemplified by the single ring, bicyclic and benzofused heteroaryl groups as defined immediately above. Het groups are joined to group B by a carbon ring member, e.g., Het is 2-pyridyl, 3-pyridyl or 2-quinolyl. The Het ring can be substituted on any available ring carbon by a group W; 1 to 4 W substituents can be present on a Het ring.

"Heterocyclyl" or "heterocycloalkyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxanyl, 1,4-dioxanyl, tetrahydrofuranyl, tetrahydrothiopyranyl, tetrahydrothiophenyl, lactam, lactone, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

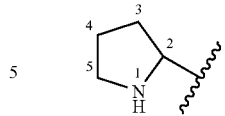

there is no —OH attached directly to carbons marked 2 and 5.

It should also be noted that tautomeric forms such as, for example, the moieties:

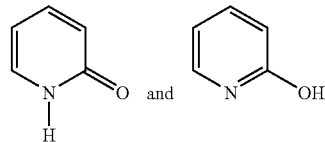

are considered equivalent in certain embodiments of this invention.

The term "heterospirocyclic" refers to a spirocyclic structure containing 3 to 5 carbon atoms and 1 or 2 heteroatoms selected from the group consisting of N, S and O, provided that the heteroatoms are not adjacent.

"Alkylamino" means an alkyl-amino group in which the alkyl group is as previously described. The bond to the parent moiety is through the amino.

"Alkylaminoalkyl" means an alkyl-amino-alkyl group in which the alkyl groups are as previously described. The bond to the parent moiety is through the alkyl.

"Alkylcycloalkylalkyl" means an alkyl-cycloalkyl-alkyl group in which the alkyl and cycloalkyl groups are as previously described. The bond to the parent moiety is through the alkyl.

"Alkylheteroaryl" means an alkyl-heteroaryl group in which the alkyl and heteroaryl groups are as previously described. The bond to the parent moiety is through the heteroaryl.

"Alkylheterocycloalkyl" means an alkyl-heterocycloalkyl group in which the alkyl and heterocycloalkyl groups are as previously described. The bond to the parent moiety is through the heterocycloalkyl group.

"Alkoxyalkyloxyalkyl" means an alkoxy-alkyl-O-alkyl group in which the alkoxy and alkyl groups are as previously described. The bond to the parent moiety is through the alkyl group.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Haloalkyl" means a halo-alkyl- group in which the alkyl group is as previously described. The bond to the parent moiety is through the alkyl. Non-limiting examples of suitable haloalkyl groups include fluoromethyl and difluoromethyl.

"Heteroaralkyl" or "heteroarylalkyl" means a heteroarylalkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Heteroarylalkenyl" means a heteroaryl-alkenyl group in which the heteroaryl and alkenyl are as previously described. Preferred heteroarylalkenyl contain a lower alkenyl group. The bond to the parent moiety is through the alkenyl group.

"Heterocyclylalkyl" or "heterocycloalkylalkyl" means a heterocyclyl-alkyl group in which the heterocyclyl and alkyl groups are as previously described. The bond to the parent moiety is through the alkyl group.

"Heterocycloalkyloxy" means a heterocycloalkyl-O— group in which the heterocycloalkyl group is as previously described. The bond to the parent moiety is through the ether atom.

"Heteroarylalkoxyalkyl" means a heteroaryl-alkoxyalkyl group in which the heteroaryl and alkoxyalkyl groups are as described above. The bond to the parent moiety is through the alkyl group.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aminoalkyl" means an amino-alkyl group in which the alkyl group is as previously described. The bond to the parent moiety is through the alkyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkenyloxy" means an alkenyl-O— group in which the alkenyl group is as previously described. The bond to the parent moiety is through the ether oxygen.

"Alkynyloxy" means an alkynyl-O— group in which the alkenyl group is as previously described. The bond to the parent moiety is through the ether oxygen.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aralkoxy" or "arylalkoxy" means an aralkyl-O— group in which the aralkyl group is as previously described. The bond to the parent moiety is through the oxygen atom.

"Alkoxyalkyl" or "alkyloxyalkyl" means an alkyl-O-alkyl group in which the alkyl and alkyl groups are as previously described. Non-limiting examples of suitable alkyloxyalkyl groups include methoxymethyl and ethoxymethyl. The bond to the parent moiety is through the alkyl group.

"Aryloxy" means an aryl-O— group in which the aryl group is as previously described. Non-limiting examples of suitable aryloxy groups include phenoxy and naphthoxy. The bond to the parent moiety is through the ether oxygen.

"Aryloxyalkyl" means an aryl-O-alkyl group in which the aryl and alkyl groups are as previously described. Non-limiting examples of suitable aryloxyalkyl groups include phenoxymethyl and naphthoxymethyl. The bond to the parent moiety is through the alkyl group.

"Arylalkoxyalkyl" means an aryl-alkoxyalkyl group in which the aryl and alkoxyalkyl groups are as previously described. The bond to the parent moiety is through the alkyl group.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Arylalkenyl" means an aryl-alkenyl- group in which the aryl and alkenyl groups are as previously described. The bond to the parent moiety is through the alkenyl.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

"Cycloalkenyloxy" means a cycloalkenyl-O— group in which the cycloalkenyl group is as previously described. The bond to the parent moiety is through the ether atom.

"Cycloalkylyalkyl" means a cycloalkyl-alkyl group in which the cycloalkyl and alkyl groups are as previously described. The bond to the parent moiety is through the alkyl group.

"Cycloalkyloxy" or "cycloalkoxy" means a cycloalkyl-O— group in which the cycloalkyl group is as previously described. The bond to the parent moiety is through the ether atom.

"Cycloalkyloxyalkyl" means a cycloalkyl-O-alkyl group in which the cycloalkyl and alkyl groups are as previously described. The bond to the parent moiety is through the alkyl group.

"Haloalkoxyalkyl" means a halo alkoxyalkyl group in which the alkoxyalkyl group is as previously described. The bond to the parent moiety is through the alkyl group.

"Heterocyclylalkoxyalkyl" means a heterocyclyl-alkoxyalkyl group in which the alkoxyalkyl group is as previously described. The bond to the parent moiety is through the alkyl group.

The optional double bond represented by =====means that at least a single bond must be present, but that a double bond can be present; when the double bond is present, $R^{10}$ is absent.

When $R^4$ and $R^5$ join to form a ring with the nitrogen to which they are attached, the rings formed are 1-pyrrolidinyl, 1-piperidinyl and 1-piperazinyl, wherein the piperazinyl ring may also be substituted at the 4-position nitrogen by a group $R^7$.

The above statements, wherein, for example, $R^4$ and $R^5$ are said to be independently selected from a group of substituents, means that $R^4$ and $R^5$ are independently selected when attached to the same nitrogen, but also that where an $R^4$ or $R^5$ variable occurs more than once in a molecule, those occurrences are independently selected. Similarly, each occurrence of $R^{13}$ or $R^{14}$ is independent of any other $R^{13}$ or $R^{14}$ in the same Q ring. Those skilled in the art will recognize that the size and nature of the substituent(s) will affect the number of substituents which can be present.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

The structure ==== in the compound of formula I, represents an optional double bond, the dotted line is a bond or no bond, resulting in a double bond or a single bond, as permitted by the valency requirement; with the proviso that $R^3$ is absent when the carbon to which $R^3$ would be attached is part of a double bond.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the, specified amounts.

Prodrugs, solvates and co-crystals of the compounds of the invention are also contemplated herein. The term "prodrug", as employed herein, denotes a compound that is a drug precursor which, upon administration to a subject, undergoes chemical conversion by metabolic or chemical processes to yield a compound of Formula I or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

A co-crystal is a crystalline superstructure formed by combining an active pharmaceutical intermediate with an inert molecule that produces crystallinity to the combined form. Co-crystals are often made between a dicarboxlyic acid such as fumaric acid, succinic acid etc. and a basic amine such as the one represented by compound I of this invention in different proportions depending on the nature of the co-crystal. (Rmenar, J. F. et. al. *J Am. Chem. Soc.* 2003, 125, 8456).

"Effective amount" or "therapeutically effective amount" is meant to describe an amount of compound or a composition of the present invention effective as thrombin receptor antagonists and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula I, and salts, solvates, co-crystals and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates, co-crystals and prodrugs of the compounds as well as the salts and solvates, co-crystals of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Polymorphic forms of the compounds of Formula I, and of the salts, solvates, co-crystals and prodrugs of the compounds of Formula I, are intended to be included in the present invention.

The compounds according to the invention have pharmacological properties; in particular, the compounds of Formula I can be nor-seco himbacine derivatives useful as thrombin receptor antagonists.

Compounds of the invention have at least one asymmetrical carbon atom and therefore all isomers, including enantiomers, stereoisomers, rotamers, tautomers and racemates of the compounds of Formula (I) (where they exist) are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of Formula I. Isomers may also include geometric isomers, e.g., when a double bond is present. Polymorphous forms of the compounds of Formula (I), whether crystalline or amorphous, also are contemplated as being part of this invention.

Those skilled in the art will appreciate that for some of the compounds of Formula I, one isomer will show greater pharmacological activity than other isomers.

Typical preferred compounds of the present invention have the following stereochemistry:

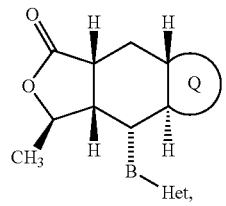

with compounds having that absolute stereochemistry being more preferred.

Those skilled in the art will appreciate that for some compounds of Formula I, one isomer will show greater pharmacological activity than other isomers.

Compounds of the present invention in which are generally prepared by processes in accordance with the following.

Some of the following below compounds, intermediates and processes, can be practiced by the methods as disclosed in any of U.S. Pat. No. 6,063,847, U.S. Pat. No. 6,326,380, U.S. Pat. No. 6,645,987, U.S. Ser. No. 10/271,715, all of which are incorporated herein by reference Following are examples of preparing starting materials and compounds of formula I. In the procedures, the following abbreviations are used:

rt room temperature
THF tetrahydrofuran
Et$_2$O ethyl ether
Me methyl
Et ethyl
EtOAc ethyl acetate
BnOCH$_2$Cl benzylchloromethylether
BuLi Butyl Lithium
DBAD Di-tert-butyl azodicarboxylate
DCE 1,2-dichloroethane
DCM Dichloromethane
DMF N,N-Dimethylformamide
DMSO Methyl sulfoxide
HATU hexafluorophosphate
HOBT or HOBt Hydroxybezotriazole
KHMDS Potassium bis(trimethylsilyl)amide
LiHMDS or LHMDS: Lithium bis(trimethylsilyl)amide
NaB(O$_2$CCH$_3$)$_3$H Sodium triacetoxyborohydride
PhSeBr Phenyl selenium bromide
PS Polymer supported
PS-EDC Polymer supported dimethyl aminopropyl ethyl-carbodiimide hydrochloride
PS—NCO Polymer supported isocyanate
PS-Tris-NH$_2$ Polymer supported trisamine
TFA Trifluoroacetic acid
THF Tetrahydrofuran
Ti(OiPr)$_4$ titanium isopropoxide;
TLC thin layer chromatography
TMSI Trimethylsilyl iodide or iodotrimethylsilane 7a-Carboxylic Acid and Amides The 7a-carboxylic acids can be prepared by the following representative procedure:

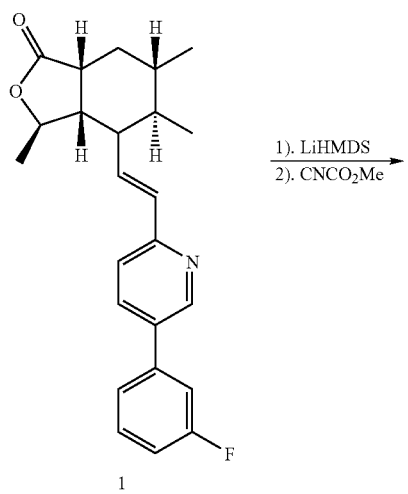

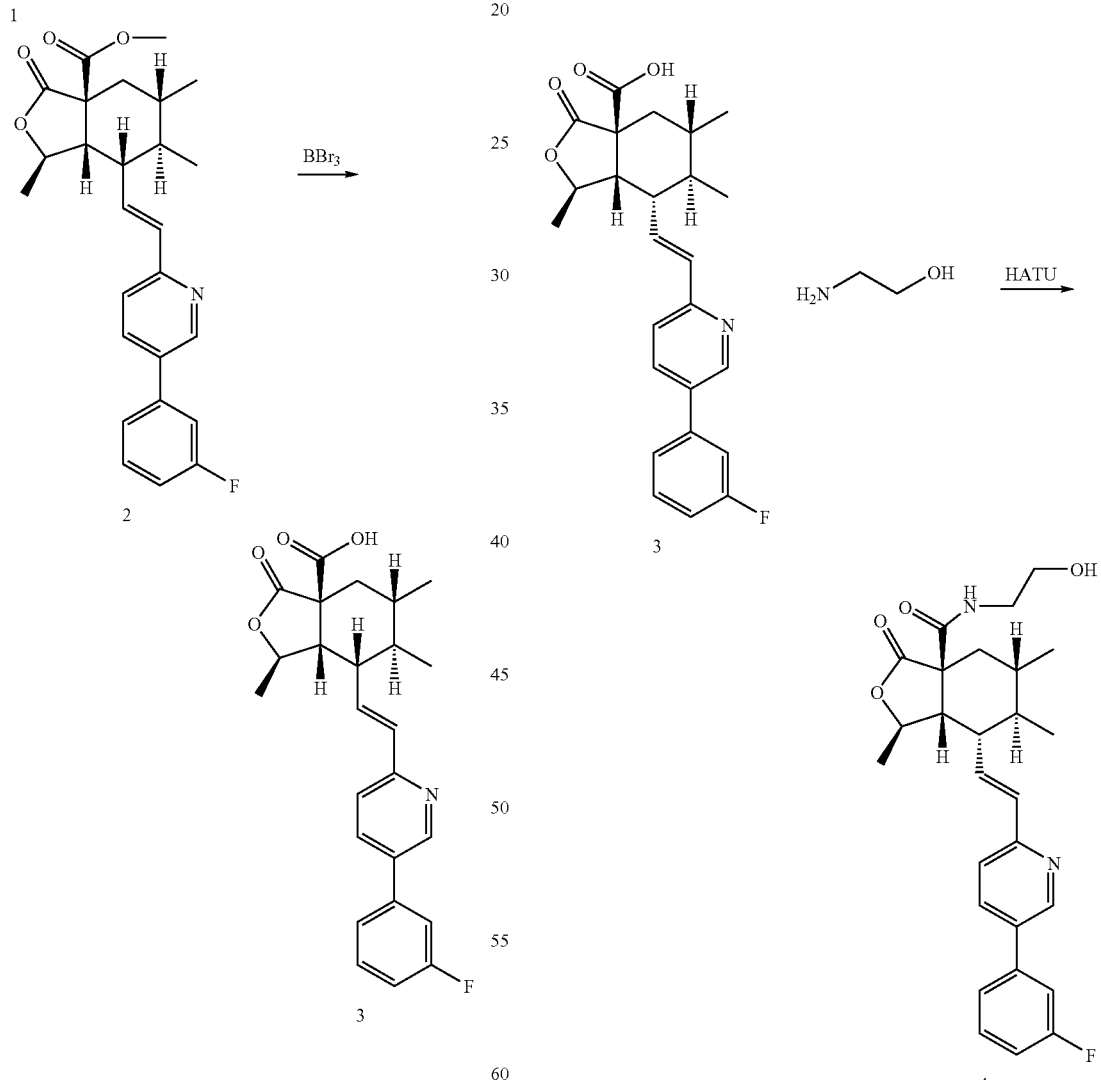

To a stirred solution of 2.5 g of compound 1 (6.59 mmol), in 50 ml of dry THF at 0° C. under argon, was added LHMDS (9.88 mmol, 9.9 ml of a 1.0M solution in THF) and the mixture allowed to stir for 30 minutes. The temperature was lowered to −78° C. and 785 μL (9.88 mmol) of methylcyanoformate was added. After 2 hours, approximately 75 mL of an aqueous solution of ammonium iron(II)sulfate hexahydrate (10% w/v) was added and the mixture then extracted with three portions of ethyl acetate. The combined organic extracts were washed with brine, dried with magnesium sulfate, filtered and evaporated to dryness. Purification by flash chromatography using 15% ethyl acetate in hexanes yielded 2.47 g of compound 2.

MS (ESI) m/z 424 (MH$^+$)

To a stirred solution of 2.47 g of compound 2 (5.65 mmol) in 50 mL of dry THF at 0° C. under N$_2$, was added boron tribromide (11.3 mmol) and the mixture allowed to stir for approximately 30 min. The reaction mixture was diluted with about 50 mL of dichloromethane and the pH adjusted, with aqueous sodium bicarbonate, to approximately pH=4 and the mixture extracted with three portions of dichloromethane. The combined organic extracts were washed with brine, dried with magnesium sulfate, filtered and evaporated yielding 2.32 g of compound 3.

MS (ESI) m/z 424.1(MH$^+$)

7a-Carboxamides

This acid can be converted to the amide 4 using standard coupling procedures. Using either commercially available amines or amines that can be prepared by synthesis, a wide variety of amide analogs were prepared. The following table summarizes some of these analogs.

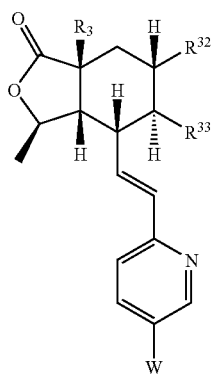
| EX. | R³ | R³² | R³³ | W | Analytical Data |
|---|---|---|---|---|---|
| A | ⤳C(O)NH-CH₂CH₂-NEt₂ | —CH₃ | Et | phenyl | MS (MH⁺) 518.1 |
| B | ⤳C(O)NH-CH₂CH₂-NMe₂ | —CH₃ | Et | phenyl | MS (MH⁺) 490.1 |
| C | ⤳C(O)NH-CH₂CH₂-OH | —CH₃ | Et | phenyl | MS (MH⁺) 463.1 |
| D | ⤳C(O)NH-CH₂CH₂-NEt₂ | —CH₃ | Et | 3-F-phenyl | HRMS (MH⁺) 539.1674 |
| E | ⤳C(O)NH-CH₂CH₂-NH₂ | —CH₃ | —CH₃ | 3-F-phenyl | HRMS (MH⁺) 466.2512 |
| F | ⤳C(O)-morpholinyl | —CH₃ | —CH₃ | 3-F-phenyl | HRMS (MH⁺) 493.2507 |
| G | ⤳C(O)NH-CH₂CH₂-OH | —CH₃ | —CH₃ | 3-F-phenyl | HRMS (MH⁺) 467.2343 |

-continued

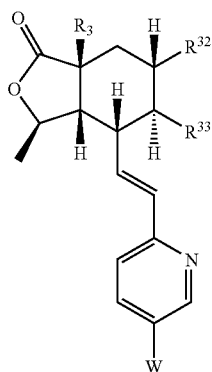

| EX. | R³ | R³² | R³³ | W | Analytical Data |
|---|---|---|---|---|---|
| H | piperazine-carbonyl (NH) | —CH₃ | —CH₃ | 3-F-phenyl | HRMS (MH⁺) 492.2655 |
| I | 4-ethylpiperazine-carbonyl | —CH₃ | —CH₃ | 3-F-phenyl | HRMS (MH⁺) 520.2980 |
| J | N-(2-pyrrolidin-1-yl-ethyl)carboxamide | —CH₃ | —CH₃ | 3-F-phenyl | HRMS (MH⁺) 520.2979 |
| K | N-(pyridin-3-yl)carboxamide | —CH₃ | —CH₃ | 3-F-phenyl | MS (MH⁺) 500.1 |
| L | (3-hydroxypyrrolidin-1-yl)carbonyl | —CH₃ | —CH₃ | 3-F-phenyl | HRMS (MH⁺) 493.2510 |
| M | N-(2-hydroxyethyl)carboxamide | —CH₃ | —CH₃ | 3-CN-phenyl | HRMS (MH⁺) 474.2397 |
| N | N-(tert-butoxycarbonylmethyl)carboxamide | —CH₃ | —CH₃ | 3-F-phenyl | MS (MH⁺) 537.1 |

-continued
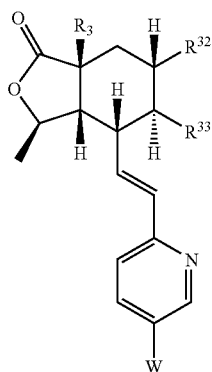
| EX. | R³ | R³² | R³³ | W | Analytical Data |
|---|---|---|---|---|---|
| O | ⟿C(O)NH-CH₂-COOH | —CH₃ | —CH₃ | 3-F-phenyl | HRMS (MH⁺) 481.2135 |
| P | ⟿C(O)NH-CH₂CH₂-OH | —CH₃ | —CH₃ | 2-CN-phenyl | MS (MH⁺) 474.3 |
| Q | ⟿C(O)NH-CH₂CH₂-NHC(O)OMe | —CH₃ | —CH₃ | 3-F-phenyl | HRMS (MH⁺) 524.2569 |
| R | ⟿C(O)NH-CH₂CH₂-NHC(O)OEt | —CH₃ | —CH₃ | 3-F-phenyl | HRMS (MH⁺) 538.2713 |
| S | ⟿C(O)NH-CH(CH₃)-CH₂OH | —CH₃ | —CH₃ | 3-F-phenyl | HRMS (MH⁺) 481.2503 |
| T | ⟿C(O)NH-CH(CH₃)-CH₂OH | —CH₃ | —CH₃ | 3-F-phenyl | HRMS (MH⁺) 481.2503 |

-continued
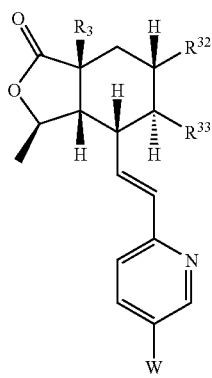
| EX. | R³ | R³² | R³³ | W | Analytical Data |
|---|---|---|---|---|---|
| U | ⸺C(O)NH-CH₂CH₂-NHSO₂Et | —CH₃ | —CH₃ | 3-F-phenyl | HRMS (MH⁺) 558.2434 |
| V | ⸺C(O)NH-C(CH₃)₂-CH₂OH | —CH₃ | —CH₃ | 3-F-phenyl | HRMS (MH⁺) 495.2651 |
| W | ⸺C(O)NH-CH₂-CH(OH)CH₃ (R) | —CH₃ | —CH₃ | 3-F-phenyl | HRMS (MH⁺) 481.2498 |
| X | ⸺C(O)NH-CH₂-CH(OH)CH₃ (S) | —CH₃ | —CH₃ | 3-F-phenyl | HRMS (MH⁺) 481.2498 |
| Y | ⸺C(O)-(3-hydroxypyrrolidinyl) | —CH₃ | —CH₃ | 3-F-phenyl | HRMS (MH⁺) 493.2503 |
| Z | ⸺C(O)NH-CH₂-C(O)NH₂ | —CH₃ | —CH₃ | 3-F-phenyl | HRMS (MH⁺) 480.2299. |

-continued
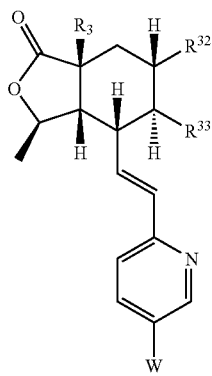
| EX. | R³ | R³² | R³³ | W | Analytical Data |
|---|---|---|---|---|---|
| AA | ![acyl-N(Me)-CH2-C(O)-N(Me)2] | —CH₃ | —CH₃ | 3-F-phenyl | HRMS (MH⁺) 544.2601 |
| BB | ![acyl-NH-CH2-(1-hydroxycyclopropyl)] | —CH₃ | —CH₃ | 2-CN-phenyl | MS (MH⁺) 500.1 |
| CC | ![acyl-NH-CH(CH3)-CH2OH] | —CH₃ | —CH₃ | 2-CN-phenyl | HRMS (MH⁺) 488.2549 |
| DD | ![acyl-NH-CH(CH3)-CH2OH] | —CH₃ | —CH₃ | 2-CN-phenyl | HRMS (MH⁺) 488.2549 |
| EE | ![acyl-NH-CH2-C(CH3)2-OH] | —CH₃ | —CH₃ | 2-CN-phenyl | MS (MH⁺) 502.1 |
| FF | ![acyl-NH-(1-(hydroxymethyl)cyclopropyl)] | —CH₃ | —CH₃ | 2-CN-phenyl | HRMS (MH⁺) |

The following tricyclic analogs were prepared using a similar procedure:

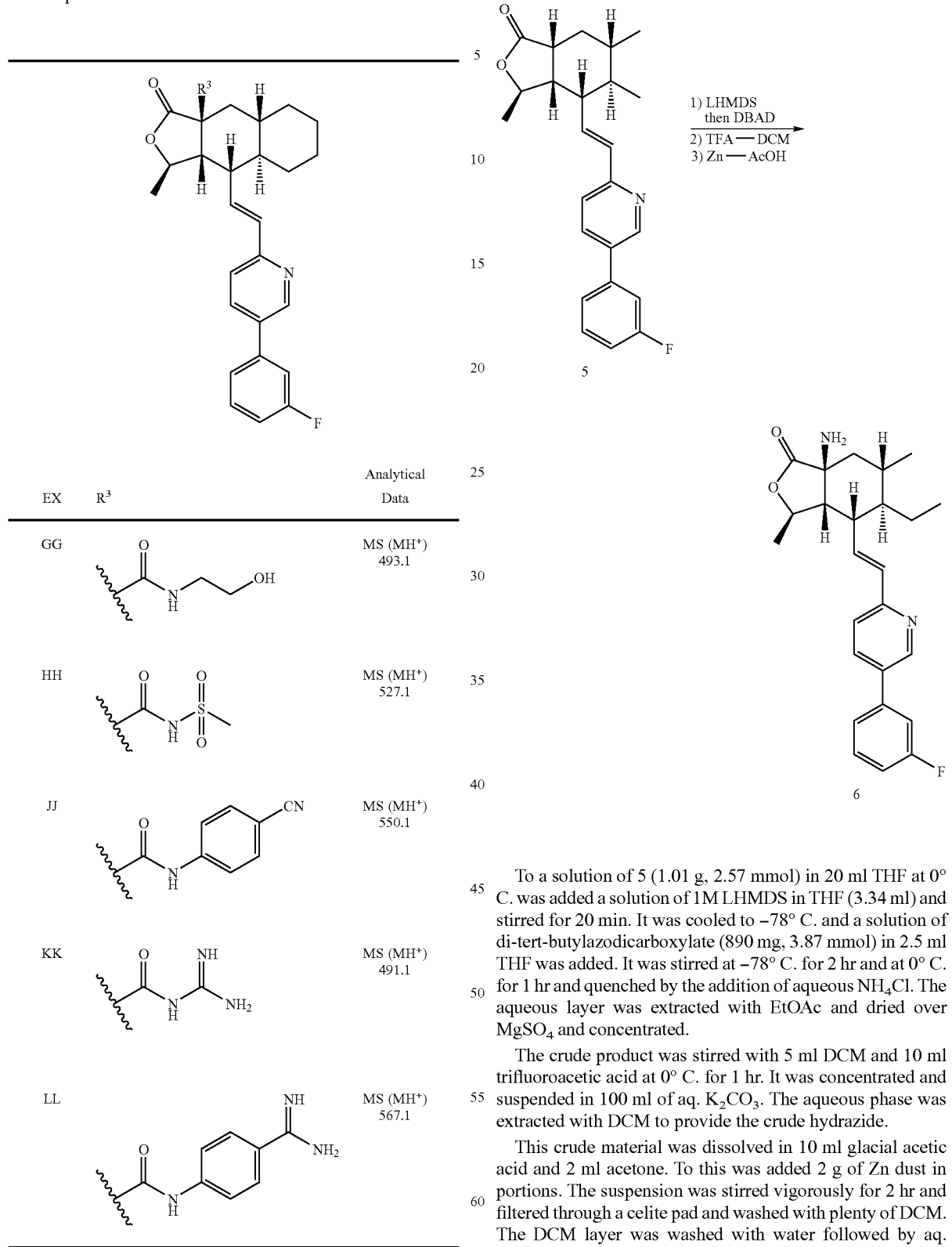

| EX | R³ | Analytical Data |
|---|---|---|
| GG | ~~~C(O)NH-CH₂CH₂-OH | MS (MH⁺) 493.1 |
| HH | ~~~C(O)NH-S(O)₂CH₃ | MS (MH⁺) 527.1 |
| JJ | ~~~C(O)NH-C₆H₄-CN | MS (MH⁺) 550.1 |
| KK | ~~~C(O)NH-C(NH)NH₂ | MS (MH⁺) 491.1 |
| LL | ~~~C(O)NH-C₆H₄-C(NH)NH₂ | MS (MH⁺) 567.1 |

7a-Amino Derivatives

The 7a-amino compounds can be prepared by the following representative procedure:

To a solution of 5 (1.01 g, 2.57 mmol) in 20 ml THF at 0° C. was added a solution of 1M LHMDS in THF (3.34 ml) and stirred for 20 min. It was cooled to −78° C. and a solution of di-tert-butylazodicarboxylate (890 mg, 3.87 mmol) in 2.5 ml THF was added. It was stirred at −78° C. for 2 hr and at 0° C. for 1 hr and quenched by the addition of aqueous NH₄Cl. The aqueous layer was extracted with EtOAc and dried over MgSO₄ and concentrated.

The crude product was stirred with 5 ml DCM and 10 ml trifluoroacetic acid at 0° C. for 1 hr. It was concentrated and suspended in 100 ml of aq. K₂CO₃. The aqueous phase was extracted with DCM to provide the crude hydrazide.

This crude material was dissolved in 10 ml glacial acetic acid and 2 ml acetone. To this was added 2 g of Zn dust in portions. The suspension was stirred vigorously for 2 hr and filtered through a celite pad and washed with plenty of DCM. The DCM layer was washed with water followed by aq. NaHCO₃ and brine. It was dried over MgSO₄, concentrated and purified by chromatography to give 500 mg of 6. MS: 409.2 (MH⁺)

The 7a-amino compounds can also be prepared by the following alternate method:

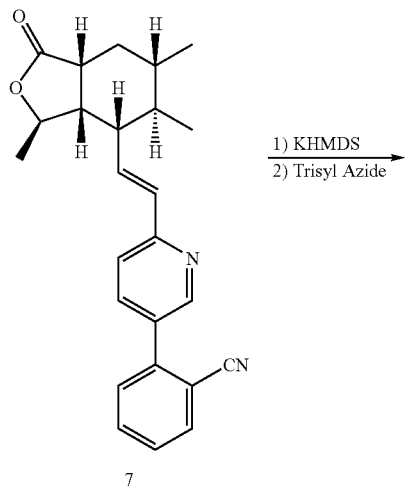

7

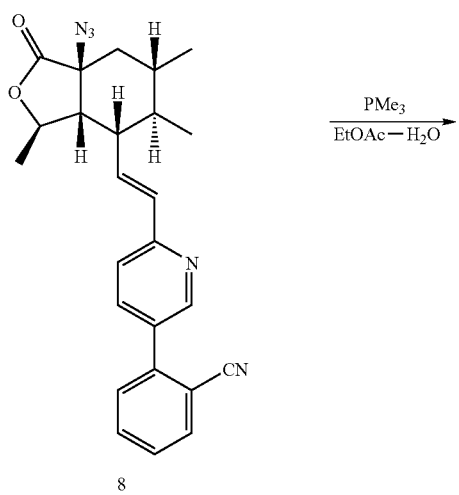

8

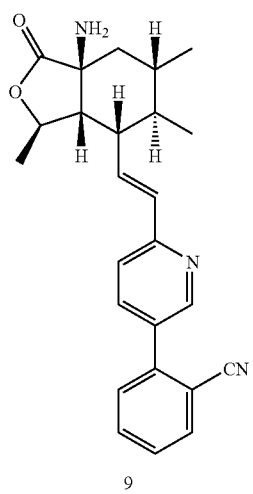

9

To a solution of 7 (2.0 g, 5.18 mmol) in 40 ml THF at 0° C. was added 0.5M solution of KHMDS in toluene (13.5 ml, 13.5 mmol, 1.3 eq) and the mixture was stirred for 15 min then cooled to −78° C. To this was added a solution of trisyl azide (2.4 g, 7.76 mmol, 1.5 eq.) in 8 ml THF and stirred for approximately 3 min. The reaction was quenched with the addition of acetic acid (0.9 m, 15.72 mmol, 3 eq.) and immediately warmed to rt using a water-bath. The mixture was stirred for 1 hr and the THF was evaporated under reduced pressure. The residue was dissolved in 100 ml $CH_2Cl_2$ and washed with 2×50 ml aq.$NaHCO_3$ and 50 ml brine, dried over $MgSO_4$, filtered, concentrated and purified by flash chromatography to provide 1.8 g of 8 as a resin. MS: 428.2 ($MH^+$)

To a solution of 8 (3.6 g, 8.42 mmol) in 50 ml EtOAc and 5 ml $H_2O$ was added a solution of 1M $PMe_3$ in THF (12.6 ml, 12.6 mmol, 1.5 eq.) and the mixture was stirred overnight at rt. The solution was concentrated and purified by chromatography to provide 2.7 g of 9 as white foam. MS: 402.1 ($MH^+$)

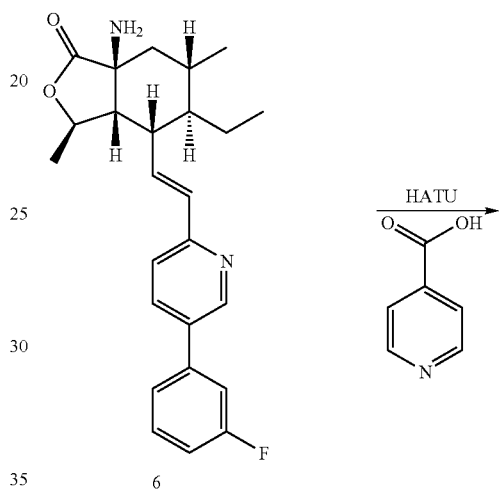

6

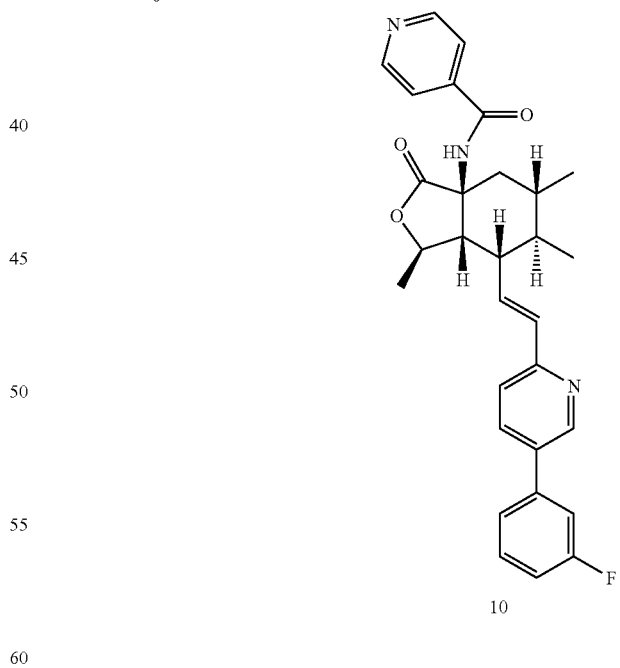

10

Amines such as 6 can be converted to amide 10 by coupling with iso-nicotinic acid. Similarly, the amines can be reacted with reagents such as aldehydes, alkyl halides, acids or acid chlorides, chloroformates, sulfonyl chlorides and isocyanates to provide secondary and tertiary amines, amides, carbamates, sulfonamides and ureas. Some of these analogs are presented in the following table.

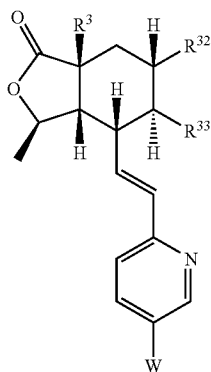
| Ex. | R³ | R³² | R³³ | W | Analytical Data |
|---|---|---|---|---|---|
| MM | ~NH-C(O)-O-tBu | —CH₃ | Et | phenyl | MS (MH⁺) 491.1 |
| NN | ~NH-C(O)-O-tBu | H | Et | phenyl | MS (MH⁺) 477.1 |
| OO | ~NH-C(O)-OEt | H | Et | phenyl | MS (MH⁺) 449.1 |
| PP | ~NH-C(O)-OEt | —CH₃ | Et | phenyl | MS (MH⁺) 463.1 |
| QQ | ~NH-C(O)-OEt | —CH₃ | Et | 3-F-phenyl | HRMS (MH⁺) 481.2492 |
| RR | ~NH-C(O)-OEt | —CH₃ | —CH₃ | 3-F-phenyl | HRMS (MH⁺) 467.2356 |
| SS | ~NH-C(O)-(3-pyridyl) | —CH₃ | Et | 3-F-phenyl | HRMS (MH⁺) 514.2501 |

-continued

| Ex. | R³ | R³² | R³³ | W | Analytical Data |
|---|---|---|---|---|---|
| TT | (4-pyridyl)C(O)NH- | —CH₃ | Et | 3-F-phenyl | HRMS (MH⁺) 514.2506 |
| UU | (3-pyridyl)C(O)NH- | —CH₃ | —CH₃ | 3-F-phenyl | HRMS (MH⁺) 500.2341 |
| VV | (4-pyridyl)C(O)NH- | —CH₃ | —CH₃ | 3-F-phenyl | HRMS (MH⁺) 500.2352 |
| WW | H₂N-CH(CH₃)-C(O)NH- | —CH₃ | Et | 3-F-phenyl | HRMS (MH⁺) 480.2658 |
| XX | H₂N-CH(CH₃)-C(O)NH- | —CH₃ | —CH₃ | 3-F-phenyl | HRMS (MH⁺) 466.2512 |
| YY | H₂N-CH(iPr)-C(O)NH- | —CH₃ | —CH₃ | phenyl | HRMS (MH⁺) 476.2924 |
| ZZ | (2-pyrrolidinyl)C(O)NH- | —CH₃ | —CH₃ | phenyl | HRMS (MH⁺) 474.2771 |

-continued
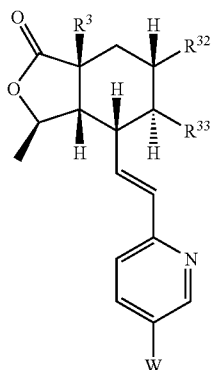
| Ex. | R³ | R³² | R³³ | W | Analytical Data |
|---|---|---|---|---|---|
| AAA | -NH-C(O)-piperidin-4-yl | —CH₃ | —CH₃ | phenyl | HRMS (MH⁺) 488.2904 |
| BBB | -NH-C(O)-pyridin-3-yl | —CH₃ | —CH₃ | 2-CN-phenyl | HRMS (MH⁺) 507.2405 |
| CCC | -NH-C(O)-(pyridin-3-yl N-oxide) | —CH₃ | —CH₃ | phenyl | HRMS (MH⁺) 498.2389 |
| DDD | pyrrolidin-1-yl | —CH₃ | —CH₃ | phenyl | MS (MH⁺) 431.1 |
| EEE | -NH-C(O)-OEt | —CH₃ | —CH₃ | 2-CN-phenyl | HRMS (MH⁺) 474.2387 |
| FFF | -NH-C(O)-OEt | —CH₃ | —CH₃ | 3-CN-phenyl | HRMS (MH⁺) 474.2387 |
| GGG | -NH-S(O)₂-CH₃ | —CH₃ | —CH₃ | 2-CN-phenyl | MS (MH⁺) 480.1 |

-continued

| Ex. | R³ | R³² | R³³ | W | Analytical Data |
|---|---|---|---|---|---|
| HHH | -NH-SO₂-Et | —CH₃ | —CH₃ | 2-CN-phenyl | MS (MH⁺) 494.1 |
| III | -NH-SO₂-cyclopropyl | —CH₃ | —CH₃ | 2-CN-phenyl | MS (MH⁺) 506.1 |
| JJJ | -NH-SO₂-Ph | —CH₃ | —CH₃ | 2-CN-phenyl | MS (MH⁺) 542.1 |

The following tricyclic analogs were prepared using similar procedure:

| EX | R³ | Analytical Data |
|---|---|---|
| KKL | -NH-C(O)-OEt | MS (MH⁺) 493.1 |

| EX | R³ | Analytical Data |
|---|---|---|
| LLL | -NH-C(O)-OMe | MS (MH⁺) 479.1 |

-continued

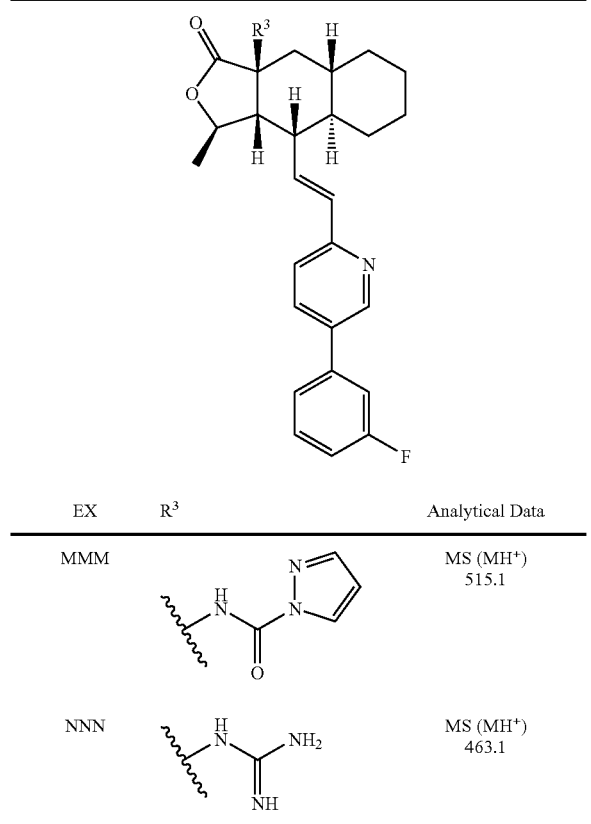

| EX | R³ | Analytical Data |
|---|---|---|
| MMM | ![pyrazole urea] | MS (MH⁺) 515.1 |
| NNN | ![guanidine] | MS (MH⁺) 463.1 |

High Throughput Synthesis:

A high throughput synthetic technique was employed to couple 7a-carboxylic acid 11 with amines to generate a 128 7a-carboxamide library 12. Similarly 7a-amino analog 9 was converted to a library of 48 ureas 13 and a library of amide 14.

Compound 11 can be prepared using a similar procedure used for the preparation of 3.

7a-Carboxamide Library

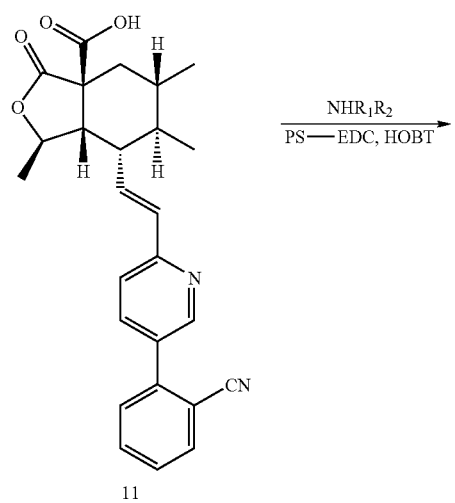

11

-continued

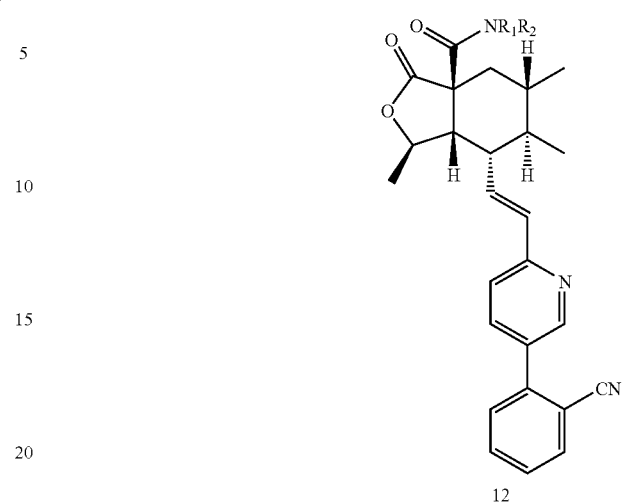

12

To 144 wells of two 96 well deep well polypropylene microtiter plates was added about 36 mg of PS-EDC (3 eq.) followed by 1 mL of a stock solution containing 1.2 g of the carboxylic acid core 9 and 565 mg of HOBT (1.5 eq.) dissolved in DMF (30 mL), MeCN (70 mL) and THF (50 mL). 1.2 eq. of 144 individual amines (1.0M solutions) were added to each well, one amine per well, and the plates were then sealed and shaken for 20 hours. The solutions were filtered through a polypropylene frit into a second set of plates containing about 36 mg of PS-isocyanate resin (3 eq.) and 26 mg of PS-Trisamine resin (6 eq.) in each well. After each well of the first plates were washed with 0.5 mL of MeCN, the second plates were sealed and shaken for 20 hours. The second plates were then filtered through a polypropylene frit into 96 well collection plates, each well washed with 0.5 mL of MeCN. The solutions were transferred from the collection plates into 2 dram vials and evaporated to dryness in a SpeedVac evaporator to provide the carboxamides.

7a-Urea Library

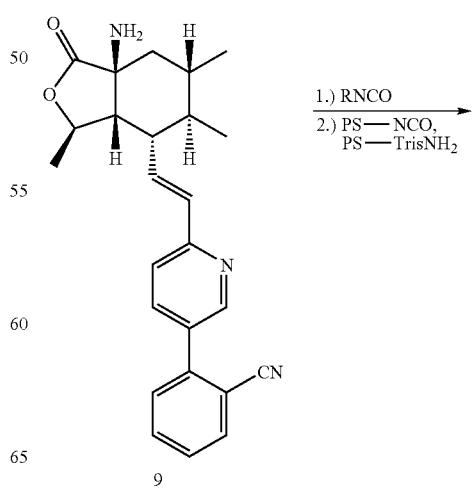

9

-continued

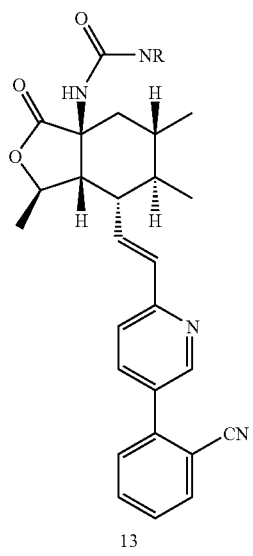

13

To 48 wells of a 96 well deep well polypropylene microtiter plate were added 1 mL of a solution containing the amine core 9 dissolved in 48mL of DCE/MeCN (1:1). 80 µL of 0.5M solutions (in DCE) of 48 individual isocyanates were then added to the wells, one isocyanate per well. The plate was sealed and shaken for 20 hours. The seal was removed and to each well were added about 33 mg of PS-isocyanate resin (3 eq.) and 30 mg of PS-Trisamine resin (6 eq.). The plate was resealed and shaken for 20 hours. The solutions were filtered through a polypropylene frit into a collection plate, each well washed with 0.5 mL of MeCN. The solutions were transferred from the collection plate into 2 dram vials and evaporated to dryness in a SpeedVac evaporator to provide the ureas.

7a-Amide Library

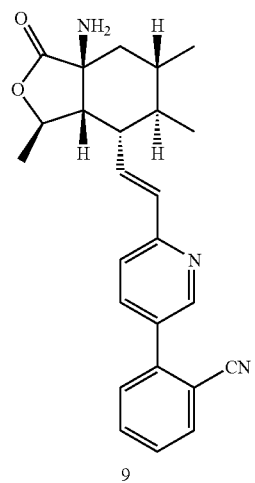

9

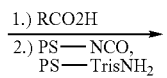

1.) RCO2H
2.) PS—NCO, PS—TrisNH2

-continued

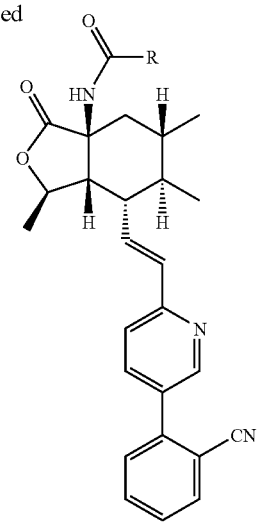

14

To each well in a deep well polypropylene microtiter plate, (where said plate contains 96 wells), was added about 56 mg of PS-EDC (3 eq.) followed by 1 mL of a stock solution containing 0.8 g of the amine core 9 and 520 mg of HOBT (1.5 eq.) dissolved in MeCN (96 mL). 1.3 eq. of 96 individual carboxylic acids (1.0M solutions) were added to each well, one carboxylic acid per well, and the plate then sealed and shaken for 20 hours. The solutions were filtered through a polypropylene frit into a second plate containing about 44 mg of PS-isocyanate resin (3 eq.) and 42 mg of PS-Trisamine resin (6 eq.) in each well. After each well of the first plate was washed with 0.5 mL of MeCN, the second plate was then sealed and shaken for 20 hours. The second plate was then filtered through a polypropylene frit into a 96 well collection plate, each well washed with 0.5 mL of MeCN. The solutions were transferred from the collection plate into 2 dram vials and evaporated to dryness in a SpeedVac evaporator to provide the amides.

Representative examples from this library of analogs are presented below:

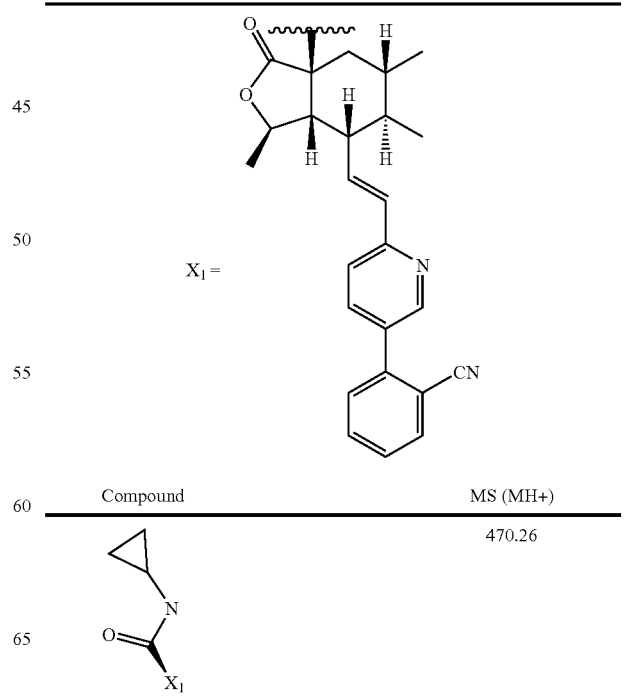

| Compound | MS (MH+) |
|---|---|
|  | 470.26 |

-continued
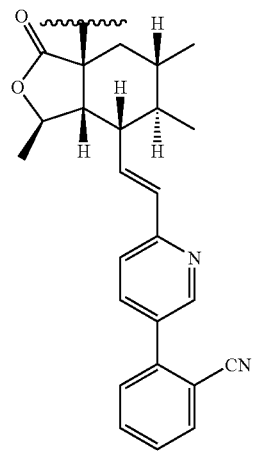
X₁ =
| Compound | MS (MH+) |
|---|---|
| H₃C-CH₂-CH₂-N(X₁)-C(=O) | 472.26 |
| N≡C-CH₂-CH₂-N(X₁)-C(=O) | 483.27 |
| cyclopropyl-CH₂-N(X₁)-C(=O) | 484.27 |
| (H₃C)₂CH-CH₂-N(X₁)-C(=O) | 486.27 |
| H₃C-O-CH₂-CH₂-CH₂-N(X₁)-C(=O) | 502.28 |
-continued
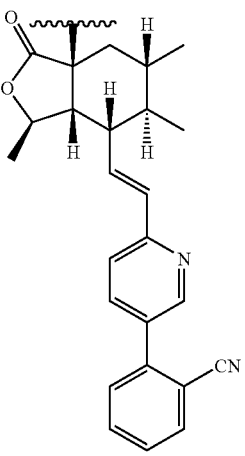
X₁ =
| Compound | MS (MH+) |
|---|---|
| furan-2-yl-CH₂-N(X₁)-C(=O) | 510.28 |
| tetrahydrofuran-2-yl-CH₂-N(X₁)-C(=O) | 514.28 |
| phenyl-CH₂-N(X₁)-C(=O) | 520.29 |
| thiophen-2-yl-CH₂-N(X₁)-C(=O) | 526.29 |

-continued
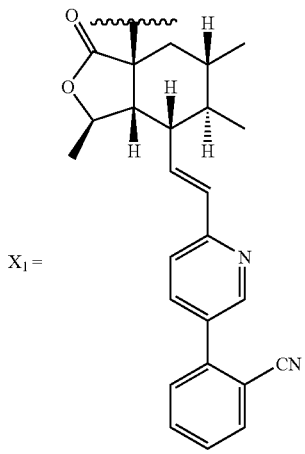
X₁ =
| Compound | MS (MH+) |
|---|---|
| 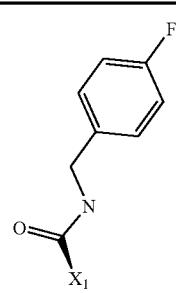 | 538.3 |
| 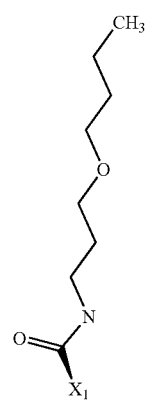 | 544.3 |
| 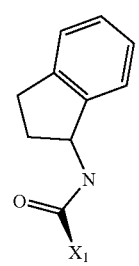 | 546.3 |
-continued
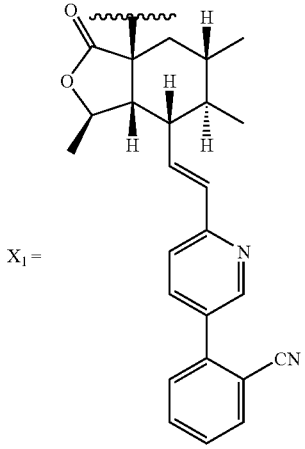
X₁ =
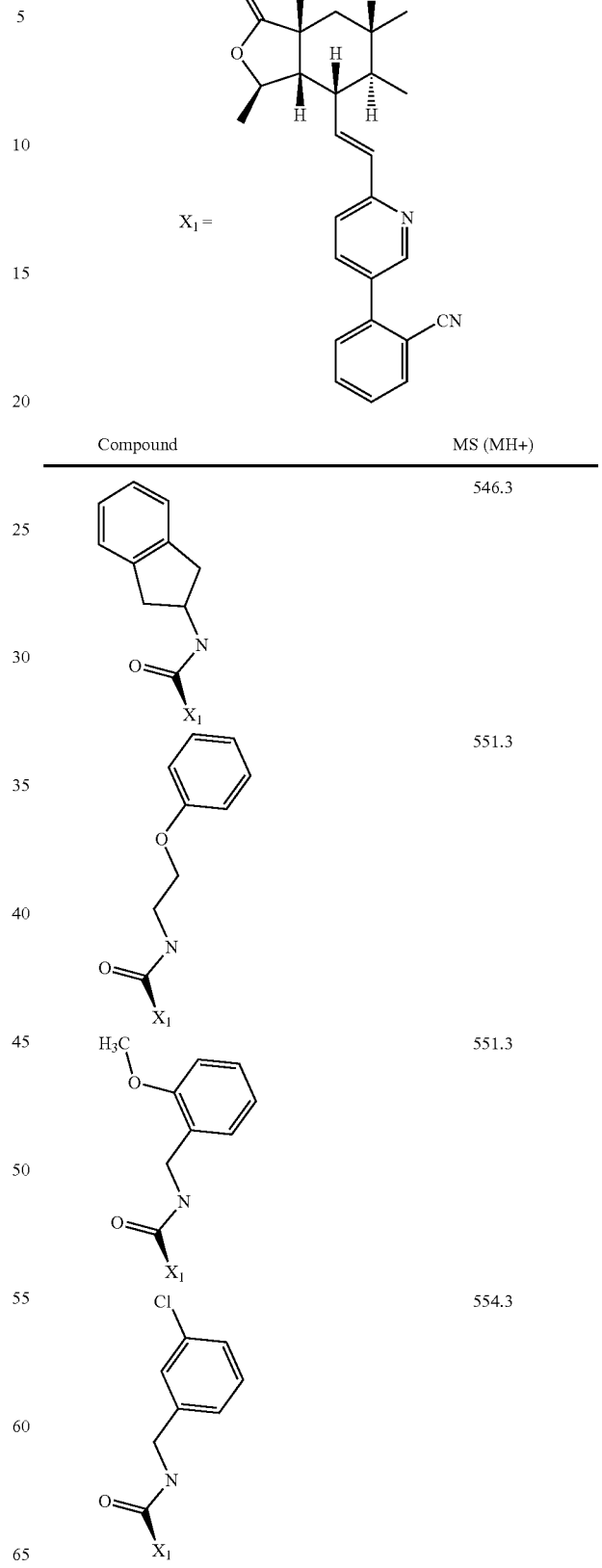
| Compound | MS (MH+) |
|---|---|
| | 546.3 |
| | 551.3 |
| | 551.3 |
| | 554.3 |

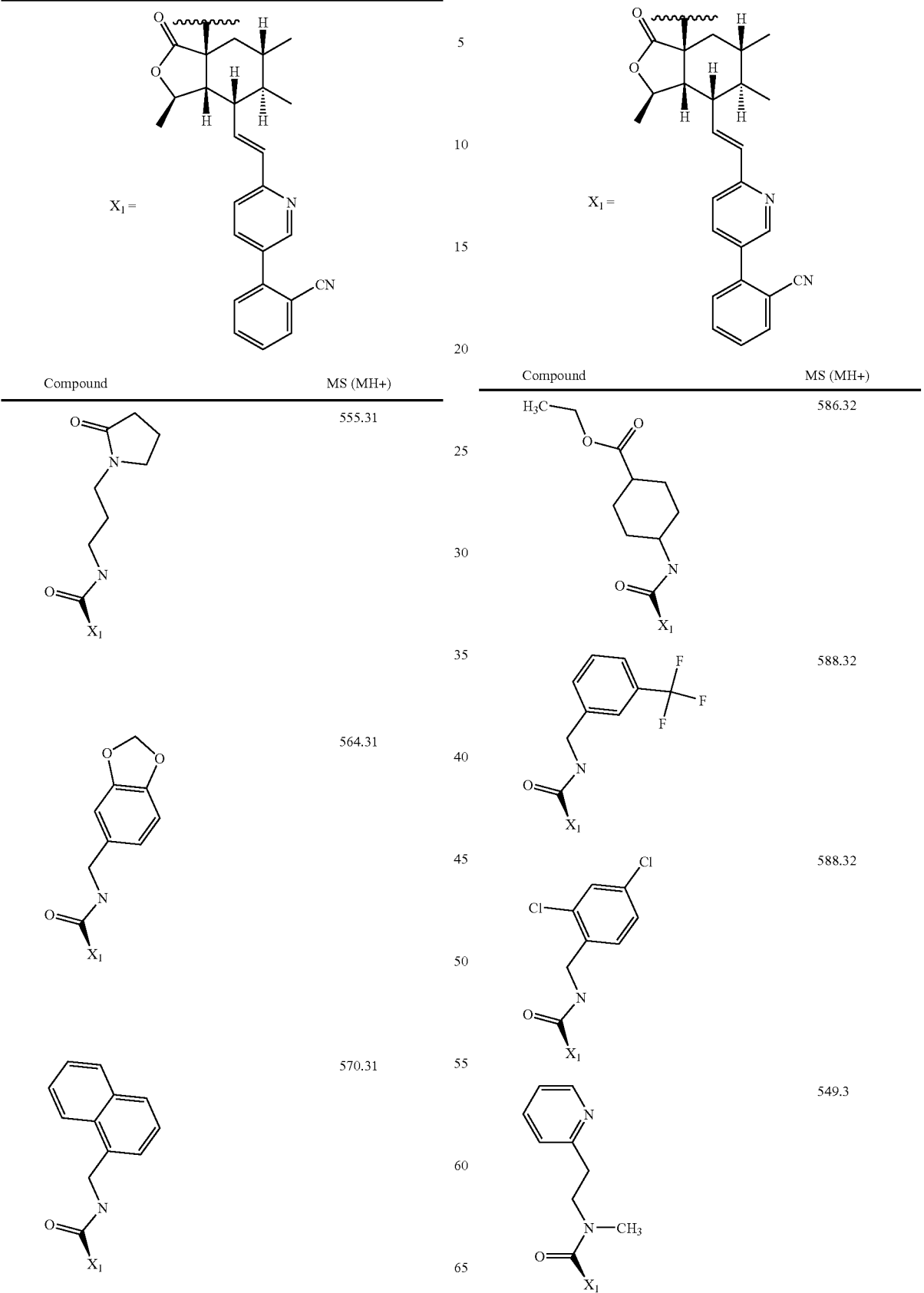

-continued
| | |
|---|---|
| $X_1$ = 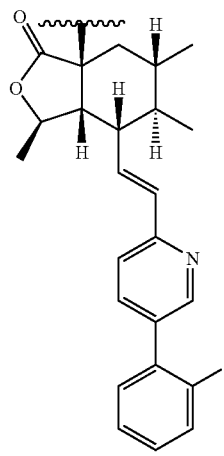 | $X_1$ = 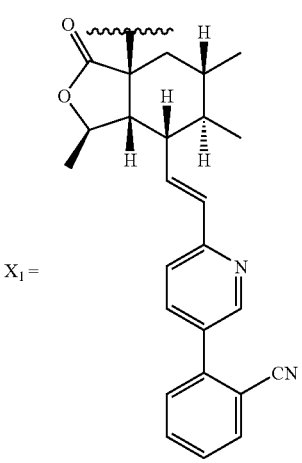 |
| Compound | MS (MH+) | Compound | MS (MH+) |
|---|---|---|---|
| 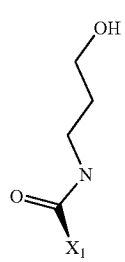 | 488.27 | 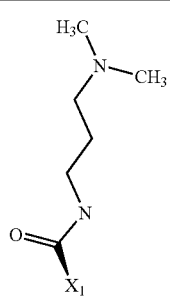 | 515.28 |
| 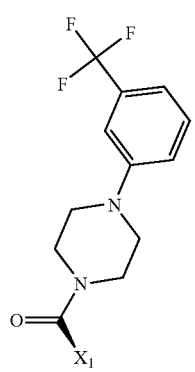 | 643.35 | | 537.3 |
| 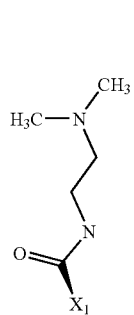 | 501.28 | 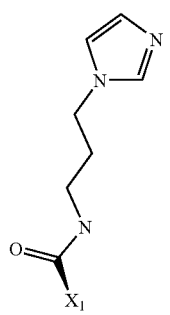 | 538.3 |

-continued
65
$X_1 =$ 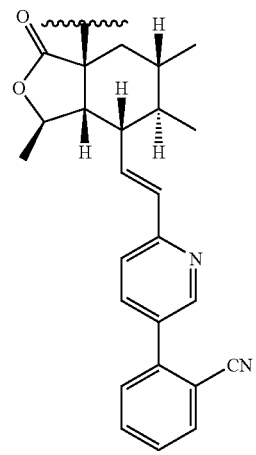
| Compound | MS (MH+) |
|---|---|
| 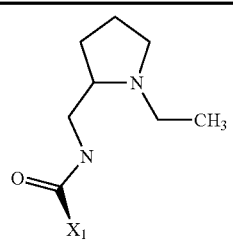 | 541.3 |
|  | 542.3 |
|  | 543.3 |
| 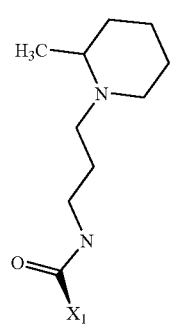 | 569.31 |
-continued
66
$X_1 =$ 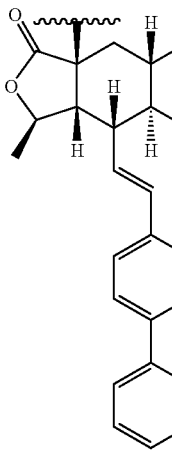
| Compound | MS (MH+) |
|---|---|
| 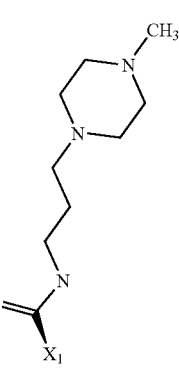 | 570.31 |
| 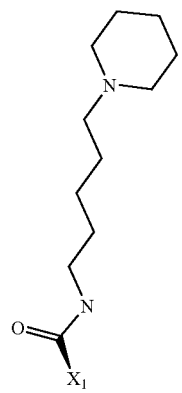 | 584.32 |
| 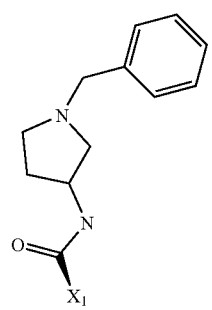 | 589.32 |

| 67 | 68 |
|---|---|
| -continued | -continued |
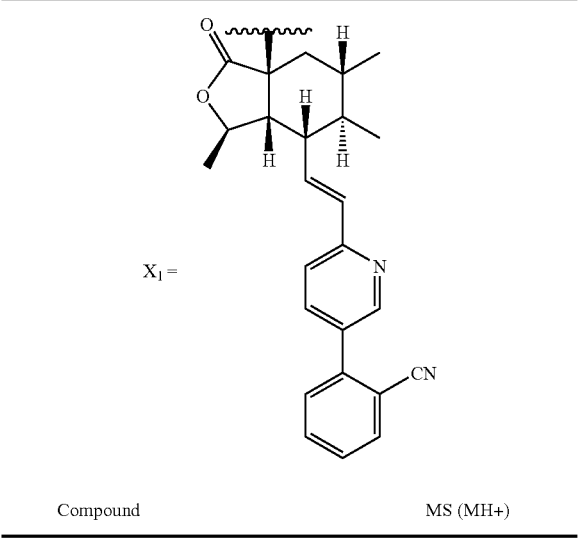
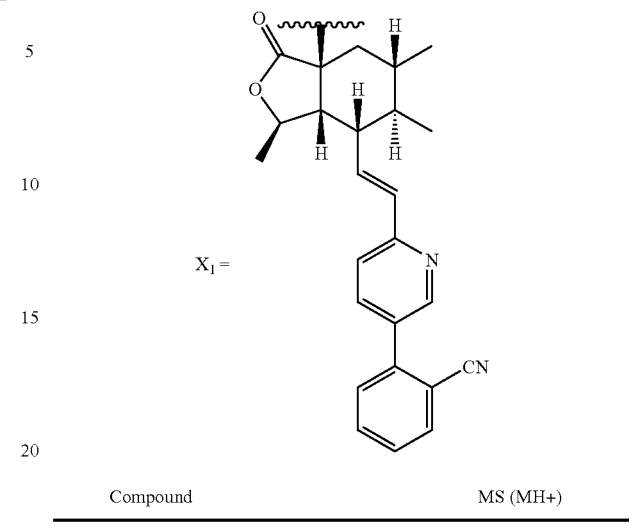
| Compound | MS (MH+) | Compound | MS (MH+) |
|---|---|---|---|
| | 591.33 | | 502.28 |
| | 604.33 | | 512.28 |
| | 498.27 | | 516.28 |
| | 500.27 | | 516.28 |
| | | | 525.29 |

-continued
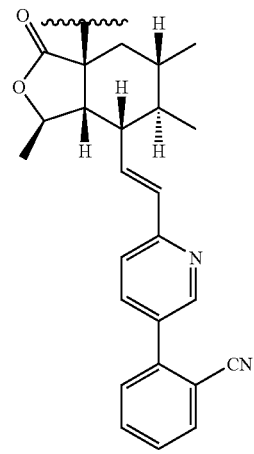
X₁ =
| Compound | MS (MH+) |
|---|---|
| 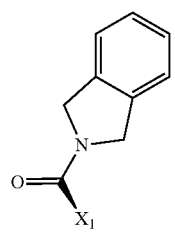 | 532.29 |
| 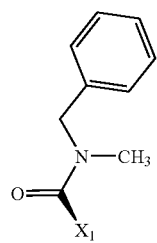 | 534.29 |
| 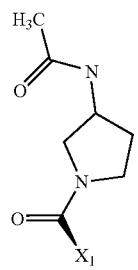 | 541.3 |
| 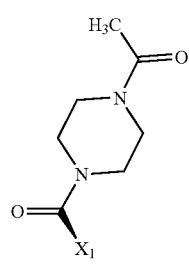 | 541.3 |
-continued
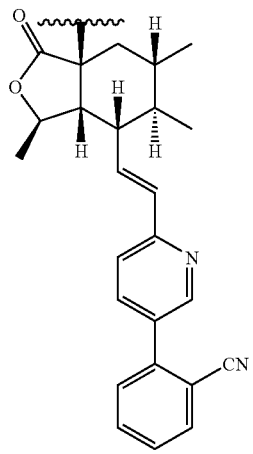
X₁ =
| Compound | MS (MH+) |
|---|---|
| 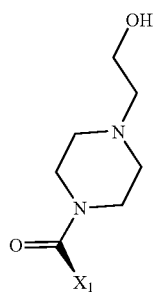 | 543.3 |
| 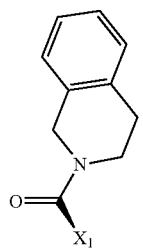 | 546.3 |
| 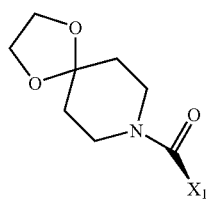 | 556.31 |
| 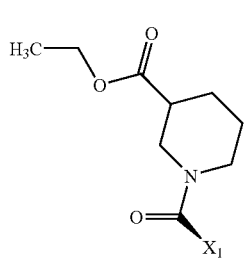 | 570.31 |

-continued
$X_1 =$ 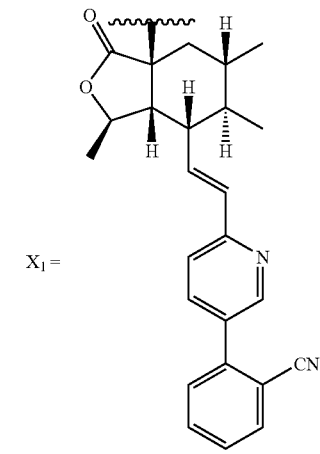
| Compound | MS (MH+) |
|---|---|
| 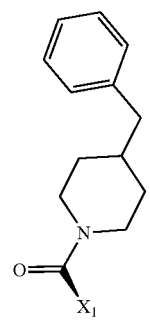 | 589.32 |
| 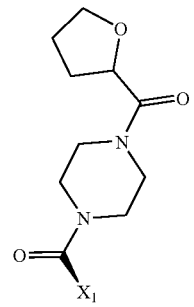 | 597.33 |
| 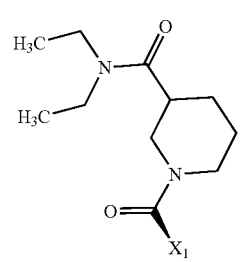 | 597.33 |
-continued
$X_1 =$ 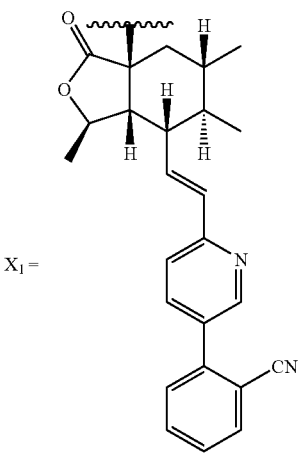
| Compound | MS (MH+) |
|---|---|
| 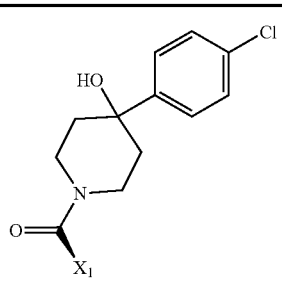 | 624.34 |
| 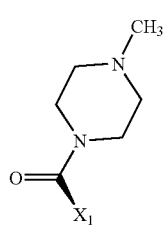 | 513.28 |
| 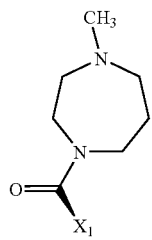 | 527.29 |
| 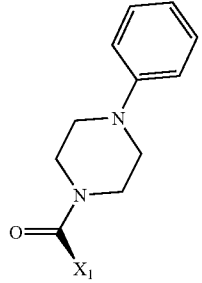 | 575.32 |

| 73 | 74 |
|---|---|
| -continued | -continued |
| 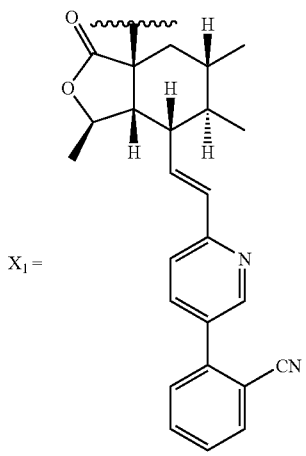 X₁ = | 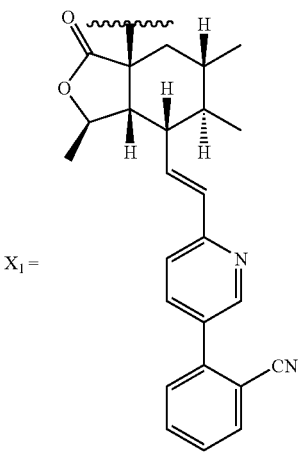 X₁ = |
| Compound | MS (MH+) | Compound | MS (MH+) |
|---|---|---|---|
| 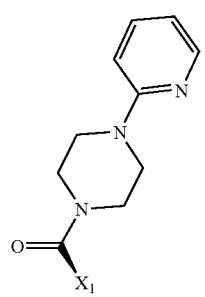 | 576.32 | 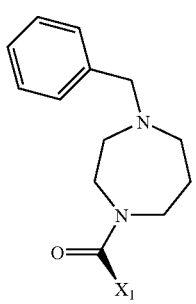 | 604.33 |
| 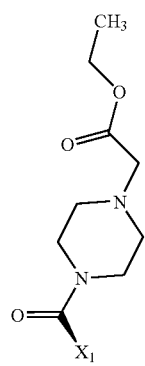 | 585.32 | 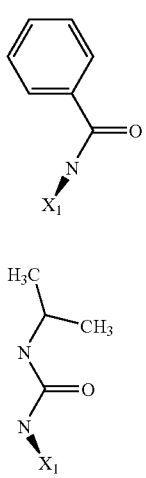 | 506.12 |
|  |  |  | 487.27 |
| 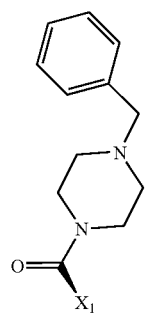 | 589.32 | 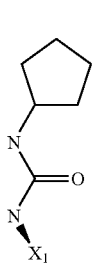 | 513.28 |

| 75 | 76 |
|---|---|
| -continued | -continued |
| $X_1 =$ 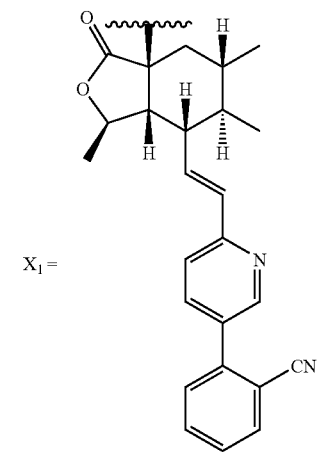 | $X_1 =$ 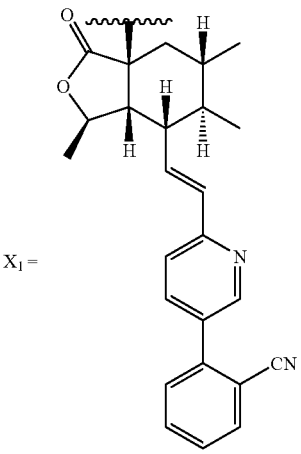 |
| Compound | MS (MH+) | Compound | MS (MH+) |
|---|---|---|---|
| 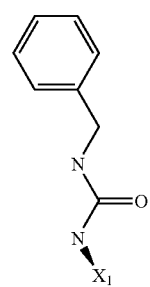 | 535.29 | 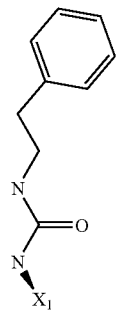 | 549.3 |
| 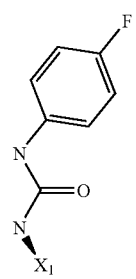 | 539.3 | 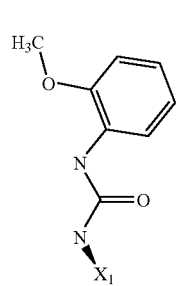 | 551.3 |
| 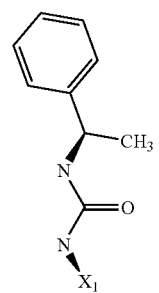 | 550.3 | 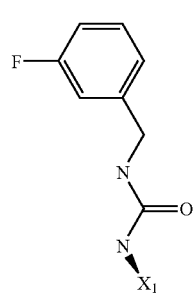 | 553.3 |

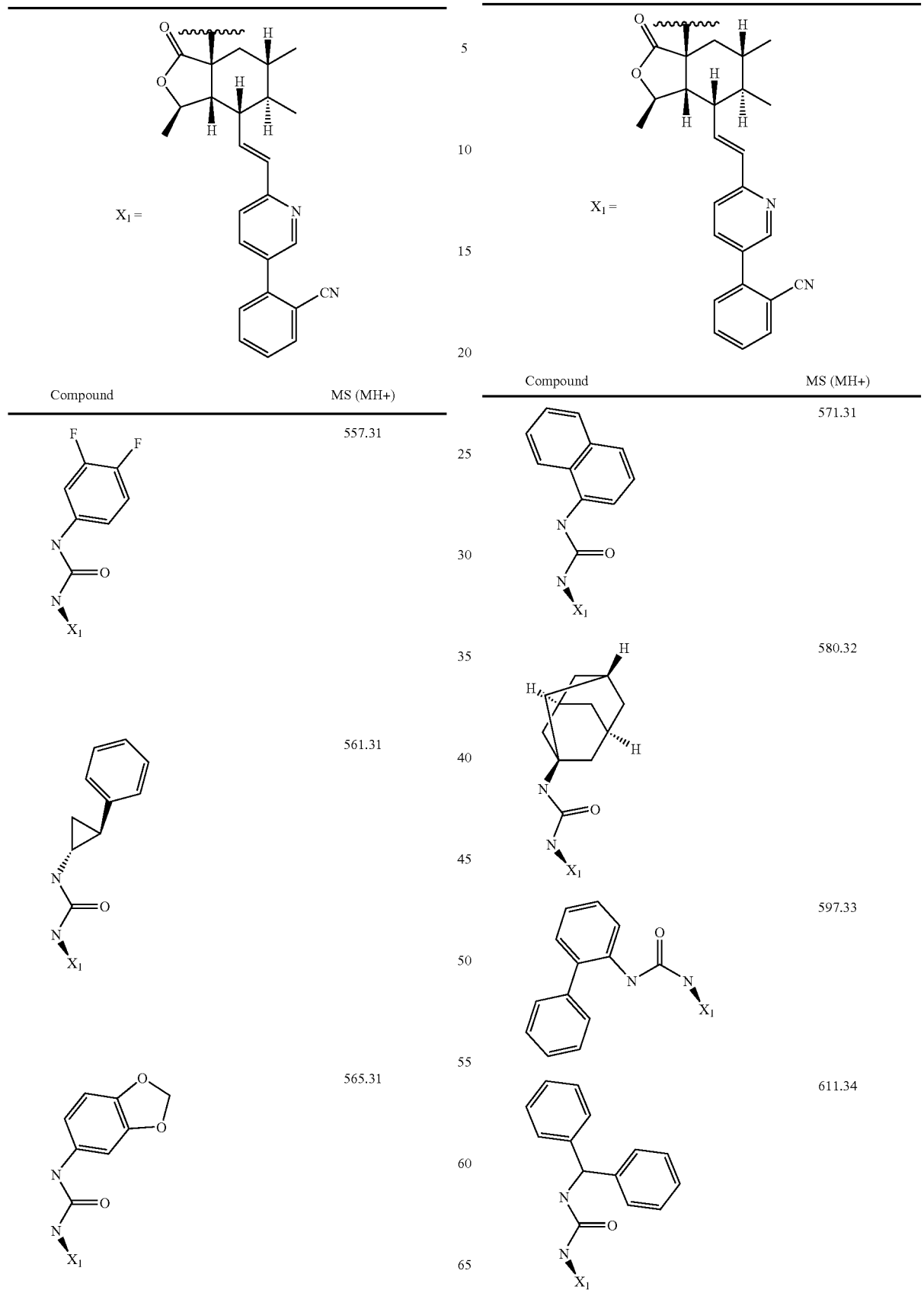

| 79 | 80 |
|---|---|
| -continued | -continued |
X₁ = 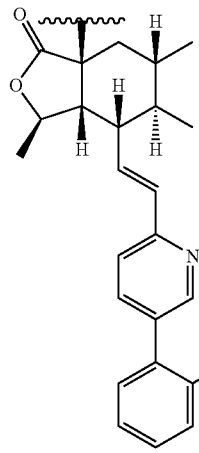   X₁ = 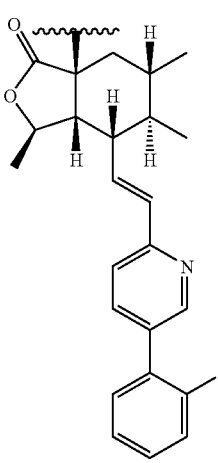
| Compound | MS (MH+) |
|---|---|
| 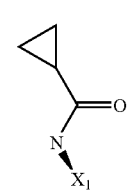 | 470.26 |
| 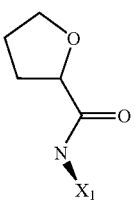 | 484.27 |
| 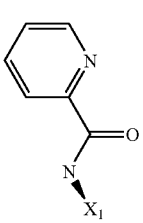 | 490.27 |
| 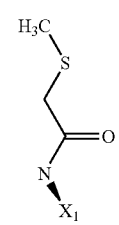 | 497.27 |
| 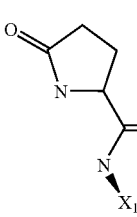 | 496.27 |
| Compound | MS (MH+) |
|---|---|
| 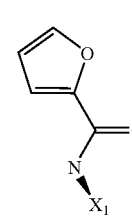 | 500.27 |
| 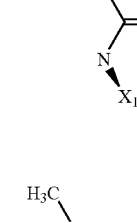 | 507.28 |
| 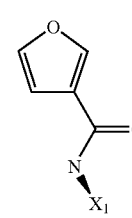 | 513.28 |
| 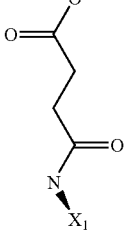 | 516.28 |

| 81 | 82 |
|---|---|
| -continued | -continued |
| 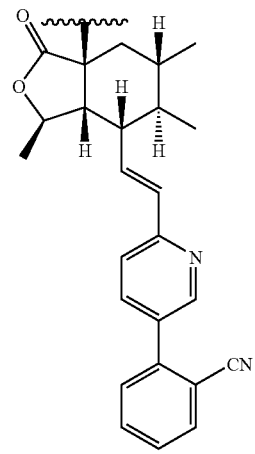 X₁ = | 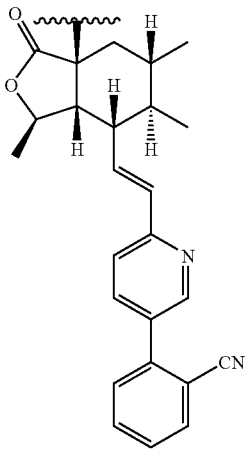 X₁ = |
| Compound | MS (MH+) | Compound | MS (MH+) |
|---|---|---|---|
| methoxyethoxyacetamide | 518.28 | 3-cyanobenzamide | 531.29 |
| furanacrylamide | 522.29 | 2-phenylpropanamide | 534.29 |
| thiopheneacetamide | 526.29 | 3-phenylpropanamide | 534.29 |
| cyclohexylacetamide | 527.29 | indole-2-carboxamide | 545.3 |

| 83 | | 84 | |
|---|---|---|---|
| -continued | | -continued | |
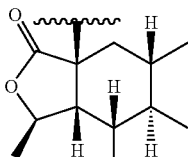
X₁ =
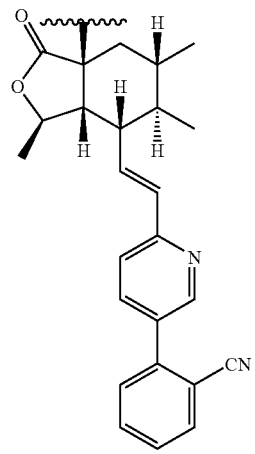
X₁ =
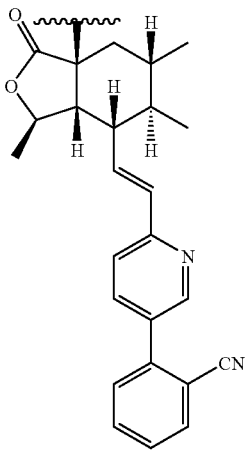
| Compound | MS (MH+) | Compound | MS (MH+) |
|---|---|---|---|
| 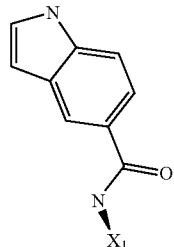 | 545.3 | 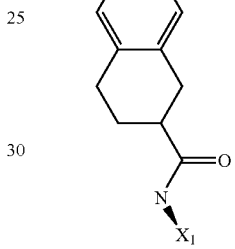 | 560.31 |
| 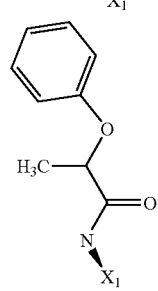 | 551.3 | | |
| 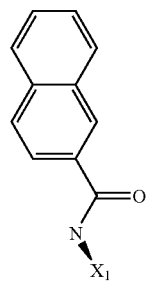 | 556.31 | 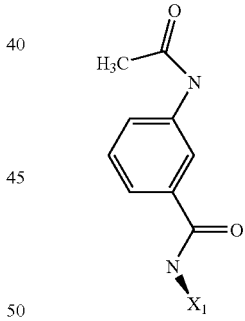 | 563.31 |
| 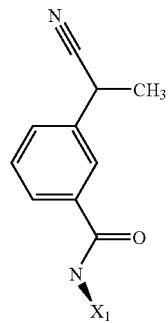 | 559.31 | 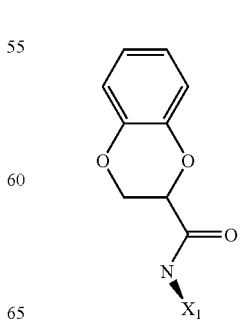 | 564.31 |

| 85 | 86 |
|---|---|
| -continued | -continued |
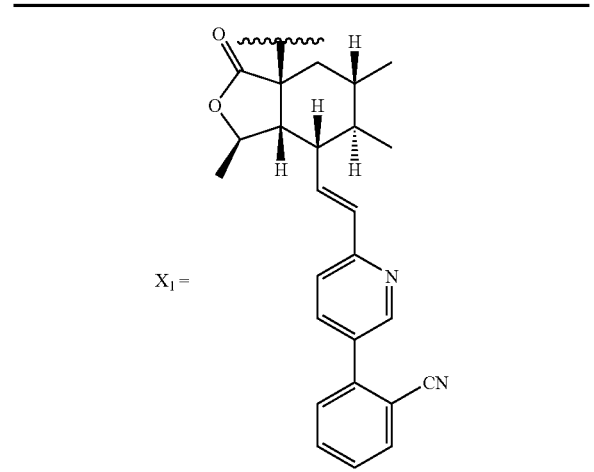
X₁ =
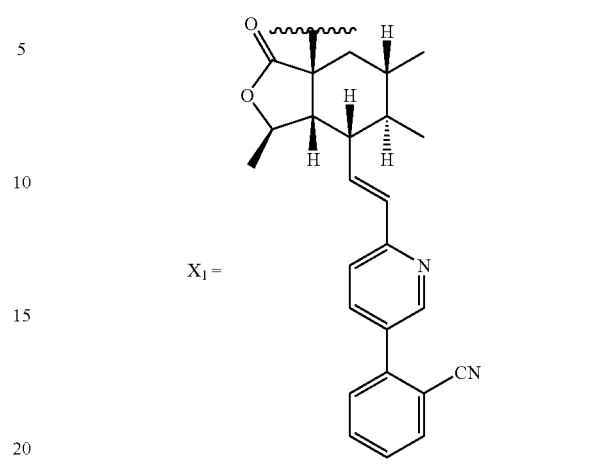
X₁ =
| Compound | MS (MH+) | Compound | MS (MH+) |
|---|---|---|---|
| 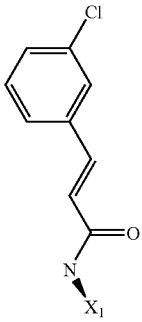 | 566.31 | 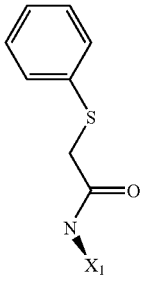 | 574.32 |
| 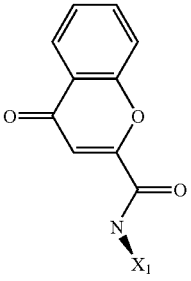 | 570.31 | 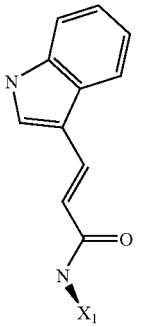 | 553.3 |
| | | 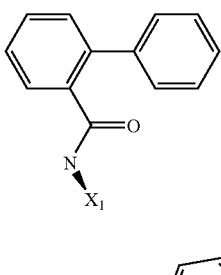 | 582.32 |
| 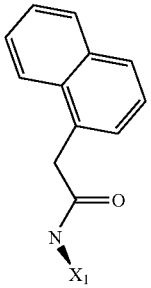 | 571.31 | 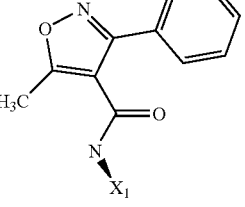 | 587.32 |

| 87 | 88 |
|---|---|
| -continued | -continued |
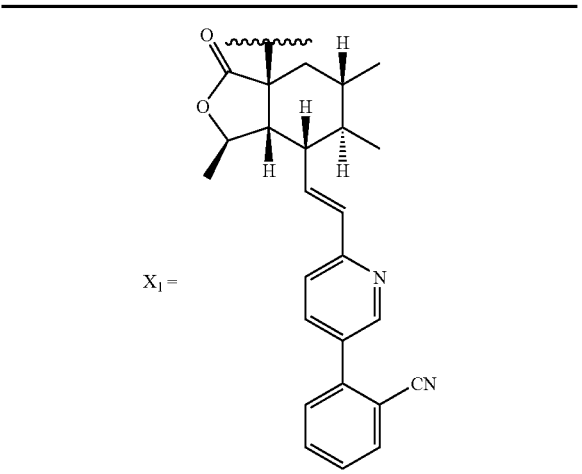
X₁ =
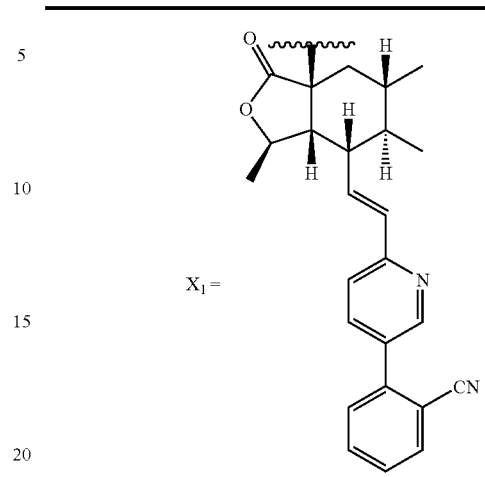
X₁ =
| Compound | MS (MH+) |
|---|---|
| 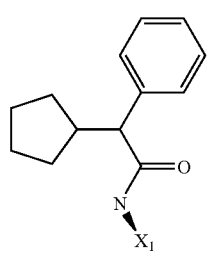 | 588.32 |
| 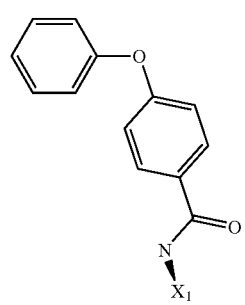 | 598.33 |
| 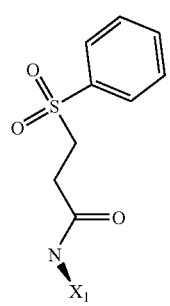 | 598.33 |
| 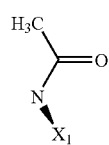 | 445.24 |
| Compound | MS (MH+) |
|---|---|
| 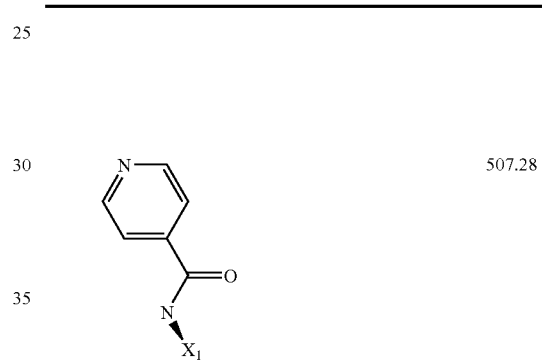 | 507.28 |
7a Hydroxymethyl
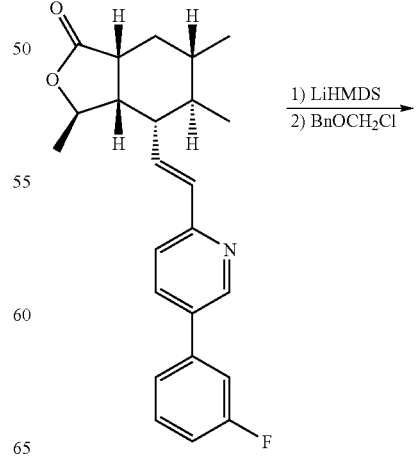 
1) LiHMDS
2) BnOCH₂Cl

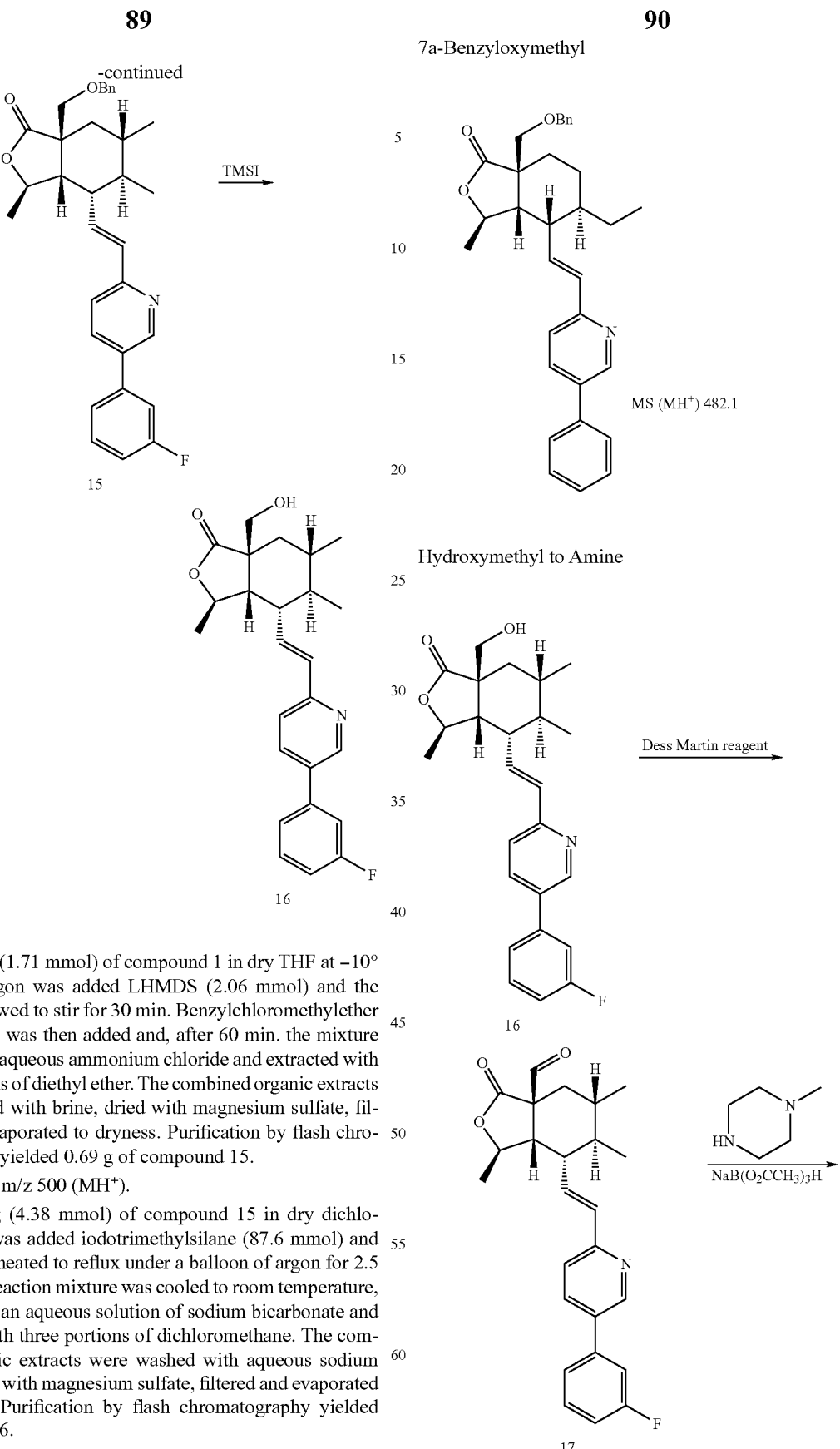

To 0.65 g (1.71 mmol) of compound 1 in dry THF at −10° C. under argon was added LHMDS (2.06 mmol) and the mixture allowed to stir for 30 min. Benzylchloromethylether (2.57 mmol) was then added and, after 60 min. the mixture poured onto aqueous ammonium chloride and extracted with three portions of diethyl ether. The combined organic extracts were washed with brine, dried with magnesium sulfate, filtered and evaporated to dryness. Purification by flash chromatography yielded 0.69 g of compound 15.

MS (ESI) m/z 500 (MH$^+$).

To 2.19 g (4.38 mmol) of compound 15 in dry dichloromethane was added iodotrimethylsilane (87.6 mmol) and the mixture heated to reflux under a balloon of argon for 2.5 hours. The reaction mixture was cooled to room temperature, poured onto an aqueous solution of sodium bicarbonate and extracted with three portions of dichloromethane. The combined organic extracts were washed with aqueous sodium sulfite, dried with magnesium sulfate, filtered and evaporated to dryness. Purification by flash chromatography yielded compound 16.

MS (ESI) m/z 410.1 (MH$^+$).

The following compound was prepared using a similar procedure:

7a-Benzyloxymethyl

MS (MH$^+$) 482.1

Hydroxymethyl to Amine

-continued

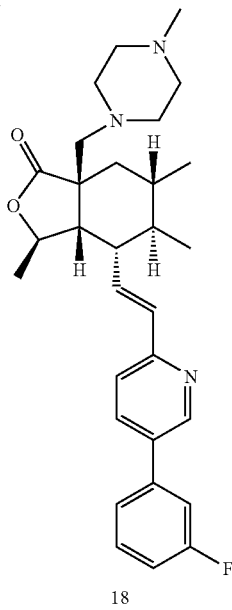

18

To 0.10 g (2.44 mmol) of compound 16 in dry dichloromethane was added 50 mg of sodium bicarbonate and 0.155 g of Dess-Martin periodinane (3.66 mmol) and the mixture allowed to stir under nitrogen for one hour. The mixture was then poured onto sodium thiosulfate and extracted with three portions of dichloromethane. The combined organic extracts were washed with brine, dried with magnesium sulfate, filtered and evaporated to dryness. Purification by flash chromatography yielded 0.087 g of compound 17.

MS (ESI) m/z 408 (MH$^+$)

To 0.150 g (0.368 mmol) of compound 17 in dry dichloromethane was added 0.074 g of N-methylpiperazine (0.736 mmol) and 0.117 g of sodium triacetoxyborohydride (0.552 mmole) and the mixture allowed to stir for 18 hrs. under nitrogen. The reaction mixture was poured onto water and extracted with three portions of dichloromethane. The combined organic extracts were washed with water, dried with magnesium sulfate, filtered and evaporated to dryness. Purification by flash chromatography yielded 0.099 g of compound 18.

MS (ESI) m/z 492 (MH$^+$)

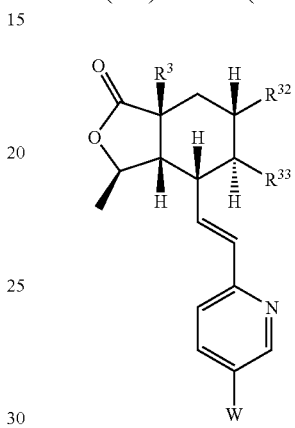

W

The following compounds were prepared using a similar procedure

| Ex. | R$^3$ | R$^{32}$ | R$^{33}$ | W | Analytical Data |
|---|---|---|---|---|---|
| OOO | ⟨pyrrolidinylmethyl⟩ | —CH$_3$ | —CH$_3$ | 3-fluorophenyl | MS (MH$^+$) 463.1 |
| PPP | ⟨3-hydroxypyrrolidinylmethyl⟩ | —CH$_3$ | —CH$_3$ | 3-fluorophenyl | HRMS (MH$^+$) 492.3026 |
| QQQ | ⟨piperidinylmethyl⟩ | —CH$_3$ | —CH$_3$ | 3-fluorophenyl | MS (MH$^+$) 477.1 |
| RRR | ⟨piperazinylmethyl⟩ | —CH$_3$ | —CH$_3$ | 3-fluorophenyl | HRMS (MH$^+$) 478.2865 |

4-Hydroxylation:

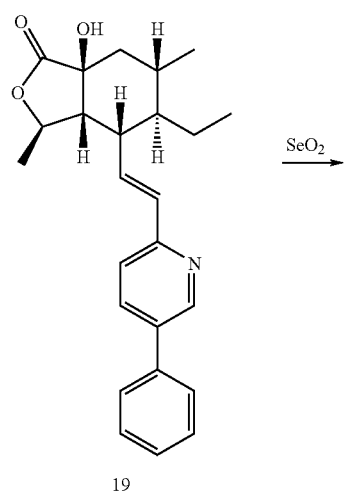

A mixture of 19 (200 mg, 0.51 mmol) and SeO$_2$ (225 mg, 2.03 mmol, 4 eq.) in 4 ml dioxane was heated in a sealed tube at 120° C. for 1.5 hr. It was filtered through a pad of florisil and rinsed with EtOAc. The eluent was washed 2× with H$_2$O, brine and dried over MgSO$_4$. It was filtered, concentrated and purified by preparative TLC eluting with 10% acetone in CH$_2$Cl$_2$ to provide 190 mg of 20. HRMS: 408.2181 (MH$^+$), calculated 408.2175

Preparation of Bicyclic and Tricyclic Alkene Derivatives

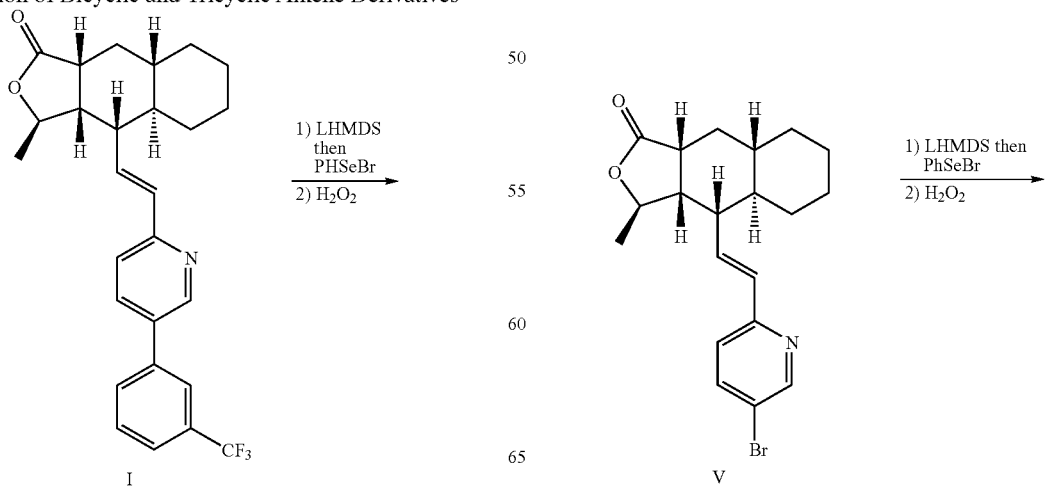

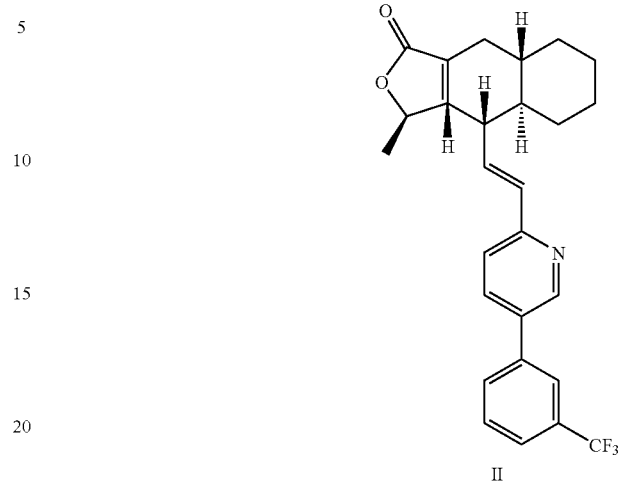

The double bond is introduced to I, by treating a compound I with LHMDS followed by PhSeBr. The resultant selenide was oxidized using hydrogen peroxide, which upon elimination provided the compound II.

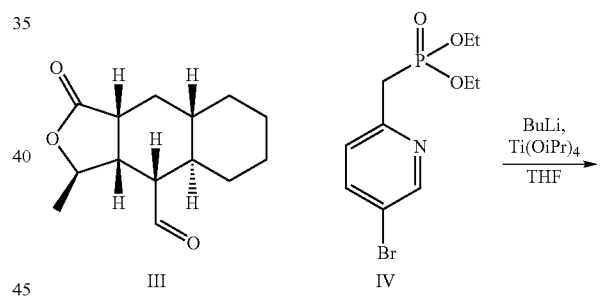

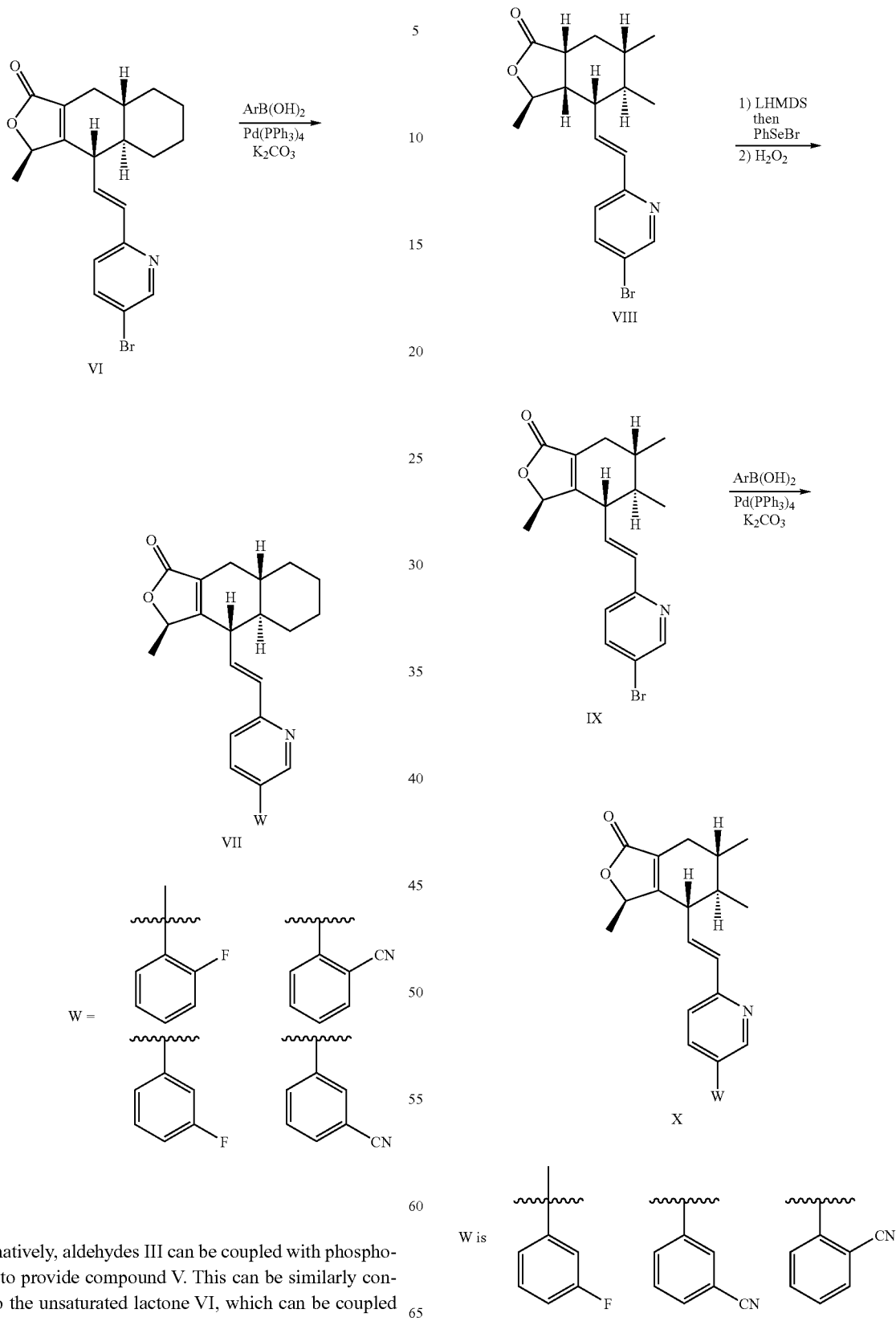
Alternatively, aldehydes III can be coupled with phosphonate IV, to provide compound V. This can be similarly converted to the unsaturated lactone VI, which can be coupled with a variety of boronic acids to provide analogs VII. Similarly compound VIII can be converted to analogs X.

Experimental for Unsaturated Lactones

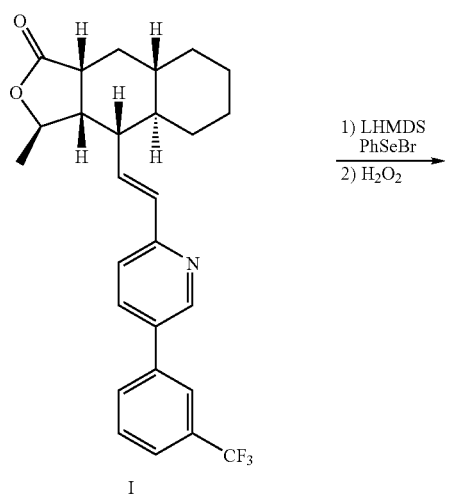

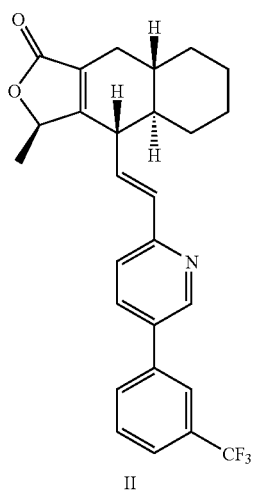

To a solution of I (2.0 g, 4.39 mmol) in 20 ml THF at 0° C. was added 1M solution of LHMDS in THF (8.8 ml, 8.8 mmol). The mixture was stirred for 20 min. at 0° C., cooled to −78° C. and a solution of PhSeBr (2.1 g, 8.9 mmol) in 10 ml THF was added. The mixture was stirred for 30min. at −78° C., 1 hr at 0° C., quenched by the addition of aq. NH$_4$Cl and extracted with EtOAc to provide the crude selenide.

The selenide was dissolved in 30 ml CH$_2$Cl$_2$ and 3.8 ml of 30% aq. H$_2$O$_2$ was added to this solution. The mixture was stirred for 1 hr at rt, diluted with EtOAc and washed with aq. NaHCO$_3$ and brine. It was dried over MgSO$_4$, filtered, concentrated and purified by chromatography to provide 1.59 g of II.

MS: 454.1 (MH$^+$)

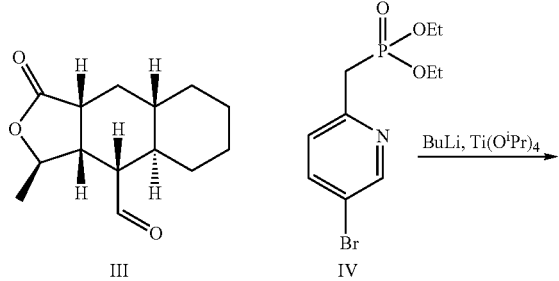

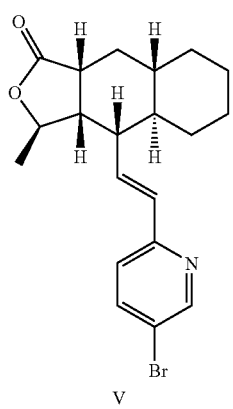

To a solution of IV (1.7 g, 5.52 mmol) in 20 ml THF at 0° C. was added a solution of 1M LHMDS in THF (5.5 ml, 5.5 mmol) and the mixture was stirred for 30 min. To this was added Ti(O$^i$Pr)$_4$ (1.9 ml, 6.44 mmol) followed by a solution of III (14.2 mmol) in 5 ml THF. The mixture was stirred for 30 min at 0° C. and quenched by the addition of aq. sodium potassium tartrate and extracted with EtOAc to provide the crude product which was purified by chromatography to provide 1.26 g of V.

MS: 390.1 (MH$^+$)

Using a similar procedure used for the preparation of II, V was converted to VI which was subjected to the standard Suzuki coupling conditions to provide product VII.

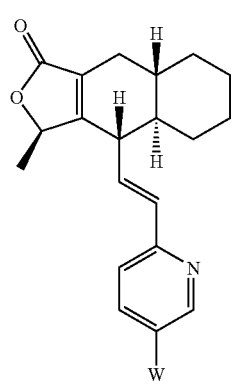

| EX. | W | Analytical Data |
|---|---|---|
| SSS | 2-F-phenyl | MS (MH$^+$) 404.1 |
| TTT | 2-CN-phenyl | MS (MH$^+$) 411.1 |

-continued

VII

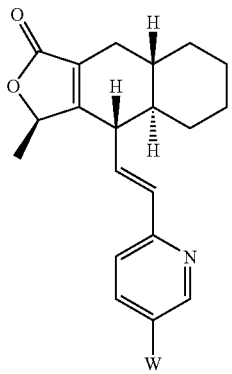

| EX. | W | Analytical Data |
|---|---|---|
| UUU | 3-F-phenyl | MS (MH+) 404.1 |
| VVV | 3-CN-phenyl | MS (MH+) 411.1 |

Similarly, VIII can be converted to product X using identical chemical procedures described above.

X

| EX | W | Analytical Data |
|---|---|---|
| WWW | 2-CN-phenyl | MS (MH+) 385.1 |
| XXX | 3-F-phenyl | MS (MH+) 378.1 |

-continued

X

| EX | W | Analytical Data |
|---|---|---|
| YYY | 3-CN-phenyl | MS (MH+) 385.1 |

Further embodiments of the invention encompass the administration of compounds of Formula I along with at least one additional cardiovascular agent. The contemplated additional cardiovascular agent is one that differs in either atomic make up or arrangement from the compounds of Formula I. Additional cardiovascular agents that can be used in combination with the novel compounds of this invention include drugs which have anti-thrombotic, anti-platelet aggregation, antiatherosclerotic, antirestenotic and/or anti-coagulant activity. Such drugs are useful in treating thrombosis-related diseases including thrombosis, atherosclerosis, restenosis, hypertension, angina pectoris, angiogenesis related disorders, arrhythmia, a cardiovascular or circulatory disease or condition, heart failure, myocardial infarction, glomerulonephritis, thrombotic stroke, thromboembolytic stroke, peripheral vascular diseases, cerebral ischemia, rheumatoid arthritis, rheumatism, astrogliosis, a fibrotic disorder of the liver, kidney, lung or intestinal tract, systemic lupus erythematosus, multiple sclerosis, osteoporosis, glomerulonephritis, renal disease, acute renal failure, chronic renal failure, renal vascular homeostasis, renal ischemia, bladder inflammation, diabetes, diabetic neuropathy, cerebral stroke, cerebral ischemia, nephritis, cancer, melanoma, renal cell carcinoma, neuropathy and/or malignant tumors, neurodegenerative and/or neurotoxic diseases, conditions, or injuries, inflammation, asthma, glaucoma, macular degeneration, psoriasis, endothelial dysfunction disorders of the liver, kidney or lung inflammatory disorders of the lungs and gastrointestinal tract, respiratory tract disease or condition, radiation fibrosis, endothelial dysfunction, periodontal diseases or wounds or a spinal cord injury, or a symptom or result thereof, as well as other disorders in which thrombin and its receptor play a pathological role. Suitable cardiovascular agents are selected from the group consisting of thromboxane A2 biosynthesis inhibitors such as aspirin; thromboxane antagonists such as seratrodast, picotamide and ramatroban; adenosine diphosphate (ADP) inhibitors such as clopidogrel; cyclooxygenase inhibitors such as aspirin, meloxicam, rofecoxib and cele coxib; angiotensin antagonists such as valsartan, telmisartan, candesartan, irbesartan, losartan and eprosartan; endothelin antagonists such as tezosentan; phosphodiesterase inhibitors such as milrinoone and enoximone; angiotensin converting enzyme (ACE) inhibitors such as captopril, enalapril, enaliprilat, spirapril, quinapril, perindopril, ramipril, fosinopril, trandolapril, lisinopril, moexipril and benazapril; neutral endopeptidase inhibitors such as candoxatril and ecadotril; anticoagulants such as ximelagatran, fondaparin and enoxaparin; diuretics such as chlorothiazide, hydrochlorothiazide, ethacrynic acid, furosemide and amiloride; platelet aggregation inhibitors such as abciximab and eptifibatide; and GP IIb/IIIa antagonists.

Preferred types of drugs for use in combination with the novel compounds of this invention are thromboxane A2 biosynthesis inhibitors, GP IIb/IIIa antagonists, thromboxane antagonists, adenosine diphosphate inhibitors, cyclooxygenase inhibitors, angiotensin antagonists, endothelin antagonists, angiotensin converting enzyme inhibitors, neutral endopeptidase inhibitors, anticoagulants, diuretics, and platelet aggregation inhibitors. Especially preferred for use in the combinations are aspirin, cangrelor and/or clopidogrel bisulfate.

When the invention comprises a combination of a compound of Formula I and another cardiovascular agent, the two active components may be co-administered simultaneously or sequentially, or a single pharmaceutical composition comprising a compound of Formula I and another cardiovascular agent in a pharmaceutically acceptable carrier can be administered. The components of the combination can be administered individually or together in any conventional dosage form such as capsule, tablet, powder, cachet, suspension, solution, suppository, nasal spray, etc. The dosage of the cardiovascular agent can be determined from published material, and may range from 1 to 1000 mg per dose.

In this specification, the term "at least one compound of Formula I" means that one to three different compounds of Formula I may be used in a pharmaceutical composition or method of treatment. Preferably one compound of Formula I is used. Similarly, the term "one or more additional cardiovascular agents" means that one to three additional drugs may be administered in combination with a compound of Formula I; preferably, one additional compound is administered in combination with a compound of Formula I. The additional cardiovascular agents can be administered sequentially or simultaneously with reference to the compound of Formula I.

When separate compounds of Formula I and the other cardiovascular agents are to be administered as separate compositions, they can be provided in a kit comprising in a single package, one container comprising a compound of Formula I in a pharmaceutically acceptable carrier, and a separate container comprising another cardiovascular agent in a pharmaceutically acceptable carrier, with the compound of Formula I and the other cardiovascular agent being present in amounts such that the combination is therapeutically effective. A kit is advantageous for administering a combination when, for example, the components must be administered at different time intervals or when they are in different dosage forms.

The following formulations exemplify some of the dosage forms of this invention. In each, the term "active compound" designates a compound of formula I.

EXAMPLE A—Tablets

| No. | Ingredient | mg/tablet | mg/tablet |
|---|---|---|---|
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
| | Total | 300 | 700 |

Method of Manufacture

Mix Item Nos. 1 and 2 in suitable mixer for 10-15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10-15 minutes. Add Item No. 5 and mix for 1-3 minutes. Compress the mixture to appropriate size and weight on a suitable tablet machine.

EXAMPLE B—Capsules

| No. | Ingredient | mg/tablet | mg/tablet |
|---|---|---|---|
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
| | Total | 250 | 700 |

Method of Manufacture

Mix Item Nos. 1, 2 and 3 in a suitable blender for 10-15 minutes. Add Item No. 4 and mix for 1-3 minutes. Fill the mixture into suitable two-piece hard gelatin capsules on a suitable encapsulating machine.

The activity of the compounds of formula I can be determined by the following procedures.

In Vitro Testing Procedure for Thrombin Receptor Antagonists: Preparation of [$^3$H]haTRAP A(pF—F)R(ChA)(hR)(I$_2$—Y)—NH$_2$ (1.03 mg) and 10% Pd/C (5.07 mg) were suspended in DMF (250 µl) and diisopropylethylamine (101 µl). The vessel was attached to the tritium line, frozen in liquid nitrogen and evacuated. Tritium gas (342 mCi) was then added to the flask, which was stirred at room temperature for 2 hours. At the completion of the reaction, the excess tritium was removed and the reacted peptide solution was diluted with DMF (0.5 ml) and filtered to remove the catalyst. The collected DMF solution of the crude peptide was diluted with water and freeze dried to remove the labile tritium. The solid peptide was redissolved in water and the freeze drying process repeated. The tritiated peptide ([$^3$H] haTRAP) was dissolved in 0.5 ml of 0.1% aqueous TFA and purified by HPLC using the following conditions: column, Vydac™ C18, 25 cm×9.4 mm I.D.; mobile phase, (A) 0.1% TFA in water, (B) 0.1% TFA in CH$_3$CN; gradient, (A/B) from 100/0 to 40/60 over 30 min; flow rate, 5 ml/min; detection, UV at 215 nm. The radiochemical purity of [$^3$H]haTRAP was 99% as analyzed by HPLC. A batch of 14.9 mCi at a specific activity of 18.4 Ci/mmol was obtained.

Preparation of Platelet Membranes

Platelet membranes were prepared using a modification of the method of Natarajan et al. (Natarajan et al, *Int. J. Peptide Protein Res.* 45:145-151 (1995)) from 20 units of platelet concentrates obtained from the North Jersey Blood Center (East Orange, N.J.) within 48 hours of collection. All steps were carried out at 4° C. under approved biohazard safety conditions. Platelets were centrifuged at 100×g for 20 minutes at 4° C. to remove red cells. The supernatants were decanted and centrifuged at 3000×g for 15 minutes to pellet platelets. Platelets were re-suspended in 10 mM Tris-HCl, pH 7.5, 150 mM NaCl, 5 mM EDTA, to a total volume of 200 ml and centrifuged at 4400×g for 10 minutes. This step was repeated two additional times. Platelets were re-suspended in 5 mM Tris-HCl, pH 7.5, 5 mM EDTA to a final volume of approximately 30 ml and were homogenized with 20 strokes in a Dounce™ homogenizer. Membranes were pelleted at 41,000×g, re-suspended in 40-50 ml 20 mM Tris-HCl, pH 7.5, 1 mM EDTA, 0.1 mM dithiothreitol, and 10 ml aliquots were frozen in liquid $N_2$ and stored at −80° C. To complete membrane preparation, aliquots were thawed, pooled, and homogenized with 5 strokes of a Dounce homogenizer. Membranes were pelleted and washed 3 times in 10 mM triethanolamine-HCl, pH 7.4, 5 mM EDTA, and re-suspended in 20-25 ml 50 mM Tris-HCl, pH 7.5, 10 mM $MgCl_2$, 1 mM EGTA, and 1% DMSO. Aliquots of membranes were frozen in liquid $N_2$ and stored at −80° C. Membranes were stable for at least 3 months. 20 units of platelet concentrates typically yielded 250 mg of membrane protein. Protein concentration was determined by a Lowry assay (Lowry et al., *J. Biol. Chem.*, 193:265-275 (1951)).

High Throughput Thrombin Receptor Radioligand Binding Assay

Thrombin receptor antagonists were screened using a modification of the thrombin receptor radioligand binding assay of Ahn et al. (Ahn et al., *Mol. Pharmacol.*, 51:350-356 (1997)). The assay was performed in 96 well Nunc plates (Cat. No. 269620) at a final assay volume of 200 μl. Platelet membranes and [$^3$H]haTRAP were diluted to 0.4 mg/ml and 22.2 nM, respectively, in binding buffer (50 mM Tris-HCl, pH 7.5, 10 mM $MgCl_2$, 1 mM EGTA, 0.1% BSA). Stock solutions (10 mM in 100% DMSO) of test compounds were further diluted in 100% DMSO. Unless otherwise indicated, 10 μl of diluted compound solutions and 90 μl of radioligand (a final concentration of 10 nM in 5% DMSO) were added to each well, and the reaction was started by the addition of 100 μl of membranes (40 μg protein/well). The binding was not significantly inhibited by 5% DMSO. Compounds were tested at three concentrations (0.1, 1 and 10 μM). The plates were covered and vortex-mixed gently on a Lab-Line™ Titer Plate Shaker for 1 hour at room temperature. Packard UniFilter™ GF/C filter plates were soaked for at least 1 hour in 0.1% polyethyleneimine. The incubated membranes were harvested using a Packard FilterMate™ Universal Harvester and were rapidly washed four times with 300 μl ice cold 50 mM Tris-HCl, pH 7.5, 10 mM $MgCl_2$, 1 mM EGTA. MicroScint™ 20 scintillation cocktail (25 μl) was added to each well, and the plates were counted in a Packard TopCount™ Microplate Scintillation Counter. The specific binding was defined as the total binding minus the nonspecific binding observed in the presence of excess (50 μM) unlabeled haTRAP. The % inhibition by a compound of [$^3$H]haTRAP binding to thrombin receptors was calculated from the following relationship:

$$\% \text{ Inhibition} = \frac{\text{Total binding} - \text{Binding in the presence of a test compound}}{\text{Total binding} - \text{Nonspecific binding}} \times 100$$

Materials

A(pF—F)R(ChA)(hR)Y—$NH_2$ and A(pF—F)R(ChA)(hR)($I_2$—Y)—$NH_2$, were custom synthesized by AnaSpec Inc. (San Jose, Calif.). The purity of these peptides was >95%. Tritium gas (97%) was purchased from EG&G Mound, Miamisburg, Ohio. The gas was subsequently loaded and stored on an IN/US Systems Inc. Trisorber. MicroScint™ 20 scintillation cocktail was obtained from Packard Instrument Co.

Protocol For Ex-Vivo Platelet Aggregation In Cynomolgus Whole Blood Drug Administration and Blood Collection:

Conscious chaired cynomolgus monkeys are allowed to equilibrate for 30 min. A needle catheter is inserted into a brachial vein for infusion of test drugs. Another needle catheter is inserted into the other brachial or saphenous vein and used for blood sampling. In those experiments where the compound is administered orally only one catheter is used. A baseline blood sample (1-2 ml) is collected in vacutainer tubes containing a thrombin inhibitor CVS 2139 (100 μg/0.1 ml saline) as an anticoagulant. The drug is then infused intravenously over a period of 30 min. Blood samples (1 ml) are collected at 5, 10, 20, 30 min during and 30, 60, 90 min after termination of the drug infusion. In PO experiments the animals are dosed with the drug using a gavage cannula. Blood samples are collected at 0, 30, 60, 90, 120, 180, 240, 300, 360 min after dosing. 0.5 ml of the blood is used for whole blood aggregation and the other 0.5 ml is used for determining the plasma concentration of the drug or its metabolites. Aggregation is performed immediately after collection of the blood sample as described below.

Whole Blood Aggregation:

A 0.5 ml blood sample is added to 0.5 ml of saline and warmed to 37° C. in a Chronolog whole blood aggregometer. Simultaneously, the impedance electrode is warmed in saline to 37° C. The blood sample with a stir bar is placed in the heating block well, the impedance electrode is placed in the blood sample and the collection software is started. The software is allowed to run until the baseline is stabilized and then a 20 Ω calibration check is performed. 20 Ω is equal to 4 blocks on the graphic produced by the computer software. The agonist (haTRAP) is added by an adjustable volume pipette (5-25 μl) and the aggregation curve is recorded for 10 minutes. Maximum aggregation in 6 minutes following agonist is the value recorded.

In vitro Platelet Agqgegation Procedure:

Platelet aggregation studies were performed according to the method of Bednar et al. (Bednar, B., Condra, C., Gould, R. J., and Connolly, T. M., *Throm. Res.*, 77:453-463 (1995)). Blood was obtained from healthy human subjects who were aspirin free for at least 7 days by venipuncture using ACD as anticoagulant. Platelet rich plasma was prepared by centrifugation at 100×g for 15 minutes at 15 deg C. Platelets were pelleted at 3000×g and washed twice in buffered saline containing 1 mM EGTA and 20 μg/ml apyrase to inhibit aggregation. Aggregation was performed at room temperature in buffered saline supplemented with 0.2 mg/ml human fibrinogen. Test compound and platelets were preincubated in 96-well flat-bottom plates for 60 minutes. Aggregation was initiated by adding 0.3 μM haTRAP or 0.1 U/ml thrombin and rapidly vortexing the mixture using a Lab Line™ Titer Plate Shaker (speed 7). Percent aggregation was monitored as increasing light transmittance at 405 nm in a Spectromax™ Plate Reader.

In vivo Antitumor Procedure:

Tests in the human breast carcinoma model in nude mouse are conducted according to the procedure reported in S. Even-Ram et al., *Nature Medicine*, 4, 8 (1988), p. 909-914.

Cannabinoid $CB_2$ Receptor Binding Assay

Binding to the human cannabinoid $CB_2$ receptor was carried out using the procedure of Showalter, et al. (1996, *J. Pharmacol Exp Ther.* 278(3), 989-99), with minor modifications. All assays were carried out in a final volume of 100 ul. Test compounds were re-suspended to 10 mM in DMSO, then serially diluted in 50 mM Tris, pH 7.1, 3 mM $MgCl_2$, 1 mM EDTA, 50% DMSO. Aliquots (10 ul) of each diluted sample were then transferred into individual wells of a 96-well microtiter plate. Membranes from human $CB_2$ transfected CHO/Ki cells (Receptor Biology, Inc) were re-suspended in binding buffer (50 mM Tris, pH 7.1, 3 mM $MgCl_2$, 1 mM EDTA, 0.1% fatty acid free bovine serum albumin), then added to the binding reaction (~15 ug in 50 ul per assay). The reactions were initiated with the addition of [$^3$H] CP-55, 940 diluted in binding buffer (specific activity=180 Ci/mmol; New England Nuclear, Boston, Mass.). The final ligand concentration in the binding reaction was 0.48 nM. Following incubation at room temperature for 2 hours, membranes were harvested by filtration through pretreated (0.5% polyethylenimine; Sigma P-3143) GF-C filter plates (Unifilter-96, Packard) using a TomTeC™ Mach 3U 96-well cell harvester (Hamden, Conn.). Plates were washed 10 times in 100 ul binding buffer, and the membranes allowed to air dry. Radioactivity on membranes was quantitated following addition of Packard Omniscint™ 20 scintillation fluid using a Top-Count™ NXT Microplate Scintillation and Luminescence Counter (Packard, Meriden, Conn.). Non-linear regression analysis was performed using Prism™ 20b. (GraphPad Software, San Diego, Calif.).

Using the test procedures described above, representative compounds of formula I were found to have thrombin receptor $IC_{50}$ values (i.e., the concentration at which a 50% inhibition of thrombin receptor was observed) of 1 to 1000 nM, preferably 1-100 nM, more preferably 1-20 nM. $CB_2$ Ki values range from 1 to 1000 nM, preferably 1-200 nM, more preferably 1-100 nM.

We claim:

1. A compound represented by structural formula I:

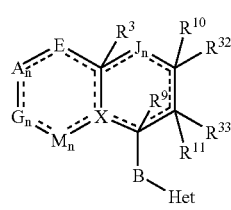

formula I or a pharmaceutically acceptable salt of said compound, wherein ----- represents a double bond or a single bond, as permitted by the valency requirement; with the proviso that $R^3$ is absent when the carbon to which $R^3$ would be attached is part of a double bond;

B is —$(CH_2)_{n4}CR^{12}$=$CR^{12a}(CH_2)_{n5}$—, wherein $n_4$ and $n_5$ are independently 0-2, and $R^{12}$ and $R^{12a}$ are independently selected from the group consisting of hydrogen, alkyl and halogen;

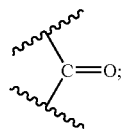

E is

M is independently selected from the group consisting of and

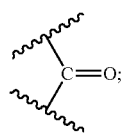

—$(CR^1R^2)$—, —O—, and

A is O;

G and J are each —$(CR^1R^2)$— for each of An, Gn and Jn, n is 1:

for Mn, n is 0:

X is —CH—, with the proviso that selection of A, G, M and X do not result in adjacent oxygen atoms;

each n is 0, 1 or 2 with the proviso that all n variables cannot be 0;

Het is a mono-, bi— or tricyclic heteroaromatic group of 5 to 14 atoms comprised of 1 to 13 carbon atoms and 1 to 4 heteroatoms independently selected from the group consisting of N, O and S, with the proviso that there are no adjacent oxygen or sulfur atoms present in the heteroaromatic group, wherein a ring nitrogen can form an N-oxide or a quaternary group with an alkyl group, wherein Het is attached to B by a carbon atom ring member, and wherein the Het group is substituted by 1 to 4 moieties, W, wherein each W is independently selected from the group consisting of hydrogen; alkyl; fluoroalkyl; difluoroalkyl; trifluoroalkyl; cycloalkyl; heterocycloalkyl; heterocycloalkyl substituted by alkyl or alkenyl; alkenyl; $R^{21}$-arylalkyl; $R^{21}$-aryl-alkenyl; heteroaryl; heteroarylalkyl; heteroarylalkenyl; hydroxyalkyl; dihydroxyalkyl; aminoalkyl; alkylaminoalkyl; di-(alkyl)-aminoalkyl; thioalkyl; alkoxy; alkenyloxy; halogen; -$NR^4R^5$;—CN; —OH; —$C(O)OR^{17}$; —$COR^{16}$; —$OS(O_2)CF_3$; —$CH_2OCH_2CF_3$; alkylthio; —$C(O)NR^4R^5$; —$OCHR^6$-phenyl; phenoxyalkyl; —$NHCOR^{16}$; —$NHSO_2R^{16}$; biphenyl; —$OC(R^6)_2COOR^7$; —$OC(R^6)_2C(O)NR^4R^5$; alkoxy substituted by alkyl, amino or —$NHC(O)OR^{17}$; aryl;

aryl substituted by 1 to 3 substituents independently selected from the group consisting of alkyl, halogen, alkoxy, methylenedioxy, carboxylic acid, carboxamide, amine, urea, amide, sulfonamide, —CN, —$CF_3$, —$OCF_3$, —OH, alkylamino-, di-(alkyl)amino-, —$NR^{25}R^{26}$alkyl-, hydroxyalkyl-, —$C(O)OR^{17}$, —$COR^{17}$, —$NHCOR^{16}$, —$NHS(O)_2R^{16}$, —$NHS(O)_2$ $CH_2CF_3$, —$C(O)NR^{25}R^{26}$, —$NR^{25}$—C(O)—

$NR^{25}R^{26}$, —S(O)$R^{13}$, —$S^{13}$ and —$SR^{13}$; or alkyl optionally substituted with —$NR^1R^2$, —$NR^1COR^2$, —$NR^1CONR^1R^2$, —$NR^1C(O)OR^2$, —$NR^1S(O)_2R^2$, —$NR^1S(O)_2NR^1R^2$, —C(O)OH, —C(O)$OR^1$, —CON$R^1R^2$heteroaryl, hydroxyalkyl, alkyl or —S(O)$_2$-alkyl; —C(O)$NR^4R^5$ or heteroaryl;

wherein adjacent carbons on the Het ring can optionally form a ring with a methylenedioxy group;

$R^1$ and $R^2$ are independently selected from the group consisting of hydrogen, alkyl, fluoroalkyl, difluoroalkyl, trifluoroalkyl, cycloalkyl, alkenyl, alkoxy, arylalkyl, arylalkenyl, heteroarylalkyl, heteroarylalkenyl, hydroxy, hydroxyalkyl, alkoxyalkyl, aminoalkyl, aryl and thioalkyl; or $R^1$ and $R^2$ when attached to nitrogen, taken together, form a mono or bicyclic heterocyclic ring of 4 to 10 atoms, with 1-3 heteroatoms selected from —O—, —N—, —S—, —S(O)—, —S(O)$_2$— and

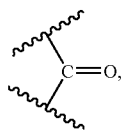

with the proviso that S and O ring atoms are not adjacent to each other, where said heterocyclic ring is unsubstituted or substituted with one or more groups selected from alkyl, halogen, hydroxy, alkoxy, aryloxy and arylalkoxy;

$R^3$ is aralkoxy, aryloxy, heteroaryl, heteroaralkoxy, —CN, —NO$_2$, —O-aryl, —O-heteroaryl, N$_3$, —C(O)$NR^{18}R^{19}$, —C(=$NR^1$)$NR^1R^2$, —N($R^1$)C=($NR^1$)$NR^1R^2$; —N=C($R^1$)$NR^1R^2$, —$NR^{18}C(O)R^{19}$, —$NR^{18}C(O)NR^{18}R^{19}$, —$NR^{18}C(O)OR^{19}$, —$NR^{18}S(O)_2R^{19}$, —$NR^{18}S(O)_2NR^{18}R^{19}$, —NHN$R^{18}R^{19}$, —$NR^{18}NR^{18}R^{19}$ or -alkyl-$NR^{18}R^{19}$;

$R^6$ is hydrogen, alkyl or phenyl;

$R^7$ is hydrogen or alkyl;

each $R^{13}$ is independently selected from hydrogen, alkyl, cycloalkyl, haloalkyl, halogen, —(CH$_2$)$_{n6}$NHC(O)$OR^{16b}$, —(CH$_2$)$_{n6}$NHC(O)$R^{16b}$, —(CH$_2$)$_{n6}$NHC(O)$NR^4R^5$, —(CH$_2$)$_{n6}$NHSO$_2R^{16}$, —(CH$_2$)$_{n6}$NHSO$_2NR^4R^5$, and —(CH$_2$)$_{n6}$C(O)$NR^{28}R^{29}$, where $n_6$ is 0-4;

each $R^{14}$ is independently selected from the group consisting of hydrogen, alkyl, —OH, alkoxy, arylalkyl, heteroaryl, heteroarylalkyl, heterocyclyl, heterocyclylalkyl, halogen, haloalkyl, —(CH$_2$)$_{n6}$NHC(O)$OR^{16b}$, —(CH$_2$)$_{n6}$NHC(O)$R^{16b}$, —(CH$_2$)$_{n6}$NHC(O)$NR^4R^5$, —(CH$_2$)$_{n6}$NHSO$_2R^{16}$, —(CH$_2$)$_{n6}$NHSO$_2NR^4R^5$, and —(CH$_2$)$_{n6}$C(O)$NR^{28}R^{29}$ where $n_6$ is 0-4; where $R^4$ and $R^5$ are independently selected from the group consisting of hydrogen, alkyl, phenyl, benzyl and cycloalkyl, or $R^4$ and $R^5$ together can form a ring with the nitrogen to which they are attached, wherein said ring formed by $R^4$ and $R^5$ is optionally substituted with =O, OH, $OR^1$ or —C(O)OH; or $R^{13}$ and $R^{14}$ taken together form a spirocyclic or a heterospirocyclic ring of 3-6 ring atoms, wherein said heterospirocyclic ring contains 2 to 5 carbon ring atoms and 1 or 2 hetero ring atoms selected from the group consisting of O, S and N;

$R^{16}$ is independently selected from the group consisting of hydrogen, alkyl, phenyl and benzyl;

$R^{16a}$ is independently selected from the group consisting of hydrogen, alkyl, phenyl and benzyl;

$R^{16b}$ is hydrogen, alkoxy, alkyl, alkoxyalkyl-, $R^{22}$—O—C(O)-alkyl-, cycloalkyl, $R^{21}$-aryl, $R^{21}$-arylalkyl, haloalkyl, alkenyl, halo substituted alkenyl, alkynyl, halo substituted alkynyl, $R^{21}$-heteroaryl, ($R^{21}$-heteroaryl)-alkyl-, ($R^{21}$ heterocycloalkyl)-alkyl-, $R^{28}R^{29}$N-alkyl-, $R^{28}R^{29}$N—C(O)-alkyl-, $R^{28}R^{29}$N—C(O)O-alkyl-, $R^{28}$OC(O)N($R^{29}$)-alkyl-, $R^{28}S(O)_2N(R^{29})$-alkyl-, $R^{28}R^{29}$N—C(O)—N($R^{29}$)-alkyl-, $R^{28}R^{29}$N—S(O)$_2$N($R^{29}$)-alkyl-, $R^{28}$-C(O)N($R^{29}$)-alkyl-, $R^{28}R^{29}$N—S(O)$_2$-alkyl-, HOS(O)$_2$-alkyl-, (OH)$_2$P(O)$_2$-alkyl-, $R^{28}$-S-alkyl-, $R^{28}$-S(O)$_2$-alkyl- or hydroxyalkyl;

$R^{17}$ is independently selected from the group consisting of hydrogen, alkyl, phenyl and benzyl;

$R^{18}$ and $R^{19}$ are hydrogen, alkyl, aryl, $R^{21}$-aryl, heteroaryl, cycloalkyl, heterocyclyl, alkoxyalkyl, haloalkoxyalkyl, aryloxyalkyl, arylalkoxyalkyl, heteroaryloxyalkyl, heteroarylalkoxyalkyl, cycloalkyloxyalkyl, (heterocyclyl)alkyloxyalkyl, alkoxyalkyloxyalkyl, —S(O)$_2$-alkyl, —C(NH)$NR^1R^2$ or alkyl substituted with one or two moieties selected from cycloalkyl, halogen, hydroxy, —$NR^1R^2$, —$NR^1C(O)R^2$, —$NR^1C(O)NR^1R^2$, —$NR^1C(O)OR^2$, —$NR^1S(O)_2R^2$, —$NR^1S(O)_2NR^1R^2$, —C(O)OH, —C(O)$OR^1$ and —C(O)$NR^1R^2$; or $R^{18}$ and $R^{19}$ together with the nitrogen to which they are attached, form a mono or bicyclic heterocyclic ring of 4 to 10 atoms, having 1-3 hetero ring atoms selected from —O—, —N—, —S—, —S(O)—, —S(O)$_2$ - and

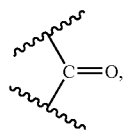

with the proviso that S and O atoms are not adjacent to each other, the ring being unsubstituted or substituted with one or more groups selected from alkyl, halogen, hydroxy, alkoxy, aryloxy, arylalkoxy, —$NR^1R^2$, —$NR^1COR^2$, —$NR^1C(O)NR^1R^2$, —$NR^1C(O)OR^2$, —$NR^1S(O)_2R^2$, —$NR^1S(O)_2NR^1R^2$, —C(O)$OR^1$, —CON$R^1R^2$ and alkyl substituted with —$NR^1R^2$, —$NR^1COR^2$, —$NR^1CONR^1R^2$, —$NR^1C(O)OR^2$, —$NR^1S(O)_2R^2$, —$NR^1S(O)_2NR^1R^2$, —C(O)$OR^1$ or —CON$R^1R^2$;

$R^{21}$ is 1 to 3 moieties and each $R^{21}$ is independently selected from the group consisting of hydrogen, —CN, —CF$_3$, —OCF$_3$, halogen, —NO$_2$, alkyl, —OH, alkoxy, alkylamino-, di-(alkyl)amino-, -$NR^{25}R^{26}$alkyl-, hydroxyalkyl-, —C(O)$OR^{17}$, —COR$^{17}$, —NHCOR$^{16}$, —NHS(O)$_2R^{16}$, —C(NH)—NH$_2$, —NHS(O)$_2$CH$_2$CF$_3$, —C(O)$NR^{25}R^{26}$, —$NR^{25}$—C(O)—$NR^{25}R^{26}$, —S(O)$R^{13}$, —S(O)$_2R^{13}$, —SR$^{13}$; —SO$_2NR^4R^5$ and —CONR$^4R^5$; or two adjacent $R^{21}$ moieties can form a methylenedioxy group;

$R^{22}$ is hydrogen, alkyl, phenyl, benzyl, —COR$^{16}$, —CONR$^{18}R^{19}$, —COR$^{23}$, —S(O)$R^{31}$, —S(O)$_2R^{31}$, —S(O$_2$)$NR^{24}R^{25}$ or —C(O)$OR^{27}$;

$R^{23}$ is

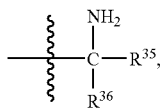

wherein $R^{35}$ and $R^{36}$ are independently selected from the group consisting of hydrogen, alkyl, and $R^{37}$-substituted alkyl, wherein $R^{37}$ is selected from the group consisting of HO—, HS—, $CH_2S$—, —$NH_2$, phenyl, p-hydroxyphenyl and indolyl; or $R^{23}$ is alkyl; haloalkyl; alkenyl; haloalkenyl; alkynyl; cycloalkyl; cycloalkylalkyl; cycloalkyl substituted by 1 to 3 substituents selected from the group consisting of alkoxyalkyl, alkyl, halogen, hydroxy, alkoxy, aryloxy, arylalkoxy, —$NR^1R^2$,
—$NR^1C(O)R^2$, —$NR^1C(O)NR^1R^2$, —$NR^1C(O)OR^2$, —$NR^1S(O)_2R^2$, —$NR^1S(O)_2NR^1R^2$, —C(O)OH, —$C(O)OR^1$ and —$CONR^1R^2$; aryl; aralkyl; heteroaryl; heterocycloalkyl;
alkyl substituted with —$NR^1R^2$, —$NR^1COR^2$, —$NR^1CONR^1R^2$, —$NR^1C(O)OR^{2,}$ —$NR^1S(O_2)R^{2,}$ —$NR^1S(O_2)NR^1R^2$, —C(O)OH, —$C(O)OR^1$, —$CONR^1R^2$ and —$SO_3H$;
$R^{24}$, $R^{25}$ and $R^{26}$ are independently selected from the group consisting of hydrogen, alkyl, haloalkyl, alkenyl, alkynyl, aryl, aralkyl, cycloalkyl, halocycloalkyl, alkoxyalkyl, hydroxy and alkoxy;
$R^{27}$ is 1 to 3 moieties and each $R^{27}$ is selected from the group consisting of hydrogen, alkyl, and cycloalkyl, wherein $R^{27}$ is optionally substituted with —OH, —C(O)OH, halogen and alkoxy;
$R^{28}$ and $R^{29}$ are independently selected from the group consisting of hydrogen, alkyl, alkoxy, arylalkyl, heteroaryl, heteroarylalkyl, hydroxyalkyl, alkoxyalkyl, heterocyclyl, heterocyclylalkyl, and haloalkyl; or
$R^{28}$ and $R^{29}$ taken together form a spirocyclic or a heterospirocyclic ring having 3-6 ring atoms;
$R^{32}$ and $R^{33}$ are independently selected from the group consisting of hydrogen,
$R^{34}$-alkyl, $R^{34}$-alkenyl and $R^{34}$-alkynyl,
$R^9$ is hydrogen, OH, alkoxy, halogen or haloalkyl
$R^{10}$ and $R^{11}$ are independently selected from the group consisting of $R^1$ and —$OR^1$;
R is 1 to 5 moieties and each R is independently selected from the group consisting of hydrogen, alkyl, halogen, hydroxy, amino, alkylamino, dialkylamino, alkoxy, —$COR^{16}$, —$C(O)OR^{17}$, —$C(O)NR^4R^5$, —$SOR^{16}$, —$S(O_2)R^{16}$, —$NR^{16}COR^{16a}$, —$NR^{16}C(O)OR^{16a}$, —$NR^{16}CONR^4R^5$, —$NR^{16}S(O_2)NR^4R^5$, fluoroalkyl, difluoroalkyl, trifluoroalkyl, cycloalkyl, alkenyl, arylalkyl, arylalkenyl, heteroarylalkyl, heteroarylalkenyl, hydroxyalkyl, aminoalkyl, aryl and thioalkyl;
$R^{34}$ is 1 to 3 moieties and each $R^{34}$ is independently selected from the group consisting of hydrogen, halogen, —OH, alkoxy, $R^{47}$-aryl, alkyl-C(O)—, alkenyl-C(O)—, alkynyl-C(O)—, heterocycloalkyl, $R^{39}$-cycloalkyl, $R^{39}$-cycloalkenyl, —$OC(O)R^{43}$, —$C(O)OR^{43}$, —$C(O)R^{43}$, —$C(O)NR^{43}R^{44}$, —$NR^{43}R^{44}$, -$NR^{43}C(O)R^{44}$, —$NR^{43}C(O)NR^{44}R^{45}$,
—$NHSO_2R^{43}$, —$OC(O)NR^{43}R^{44}$, $R^{34}$-alkenyloxy, $R^{34}$-alkynyloxy, $R^{40}$-heterocycloalkyloxy, $R^{42}$-cycloalkyloxy, $R^{42}$-cycloalkenyloxy, $R^{42}$-cycloalkyl-NH—, —$NHSO_2NHR^{16}$ and
—CH(=$NOR^{17}$);

$R^{38}$ is 1 to 3 moieties and each $R^{38}$ is independently selected from the group consisting of hydrogen, heterocycloalkyl, halogen, —$C(O)OR^{48}$, —CN, —C(O)$NR^{49}R^{50}$,
—$NR^{51}C(O)R^{52}$, —$OR^{48}$, cycloalkyl, cycloalkylalkyl, alkylcycloalkylalkyl, haloalkylcycloalkylalkyl, hydroxyalkyl, alkoxyalkyl, and $R^{52}$-heteroaryl; or two $R^{38}$ groups on adjacent ring carbons form a fused methylenedioxy group;
$R^{39}$ is 1 to 3 moieties and each $R^{39}$ is independently selected from the group consisting of hydrogen, halogen and alkoxy;
$R^{40}$ is 1 to 3 moieties and each $R^{40}$ is independently selected from the group consisting of hydrogen, $R^{41}$-alkyl, $R^{41}$-alkenyl and $R^{41}$-alkynyl;
$R^{41}$ is hydrogen, —OH or alkoxy;
$R^{42}$ is 1 to 3 moieties and each $R^{42}$ is independently selected from the group consisting of hydrogen, alkyl, —OH, alkoxy and halogen;
$R^{43}$, $R^{44}$ and $R^{45}$ are independently selected from the group consisting of hydrogen, alkyl, alkoxyalkyl, $R^{38}$-arylalkyl, $R^{46}$-cycloalkyl, $R^{53}$-cycloalkylalkyl, $R^{38}$-aryl, heterocycloalkyl, heteroaryl, heterocycloalkylalkyl and heteroarylalkyl;
$R^{46}$ is hydrogen, alkyl, hydroxyalkyl or alkoxy;
$R^{47}$ is 1 to 3 moieties and each $R^{47}$ is independently selected from the group consisting of hydrogen, alkyl, —OH, halogen, —CN, alkoxy, trihaloalkoxy, alkylamino, di(alkyl)amino, —$OCF_3$, hydroxyalkyl, —CHO, —C(O)alkylamino, —C(O)di(alkyl)amino,
—$NH_2$, —NHC(O)alkyl and —N(alkyl)C(O)alkyl;
$R^{48}$ is hydrogen, alkyl, haloalkyl, dihaloalkyl or trifluoroalkyl;
$R^{49}$ and $R^{50}$ are independently selected from the group consisting of hydrogen, alkyl, aralkyl, phenyl and cycloalkyl, or $R^{49}$ and $R^{50}$ together are —$(CH_2)_4$—, —$(CH_2)_5$— or
—$(CH_2)_2$—$NR^{39}$—$(CH_2)_2$— and form a ring with the nitrogen to which they are attached;
$R^{51}$ and $R^{52}$ are independently selected from the group consisting of hydrogen, alkyl, aralkyl, phenyl and cycloalkyl, or $R^{51}$ and $R^{52}$ in the group —$NR^{39}C(O)R^{40}$, together with the nitrogen atoms to which they are attached, form a cyclic lactam having 5-8 ring members;
$R^{53}$ is hydrogen, alkoxy, —$SOR^{16}$, —$SO_2R^{17}$, —C(O)$OR^{17}$, —C(O)$NR^{18}R^{19}$, alkyl, halogen, fluoroalkyl, difluoroalkyl, trifluoroalkyl, cycloalkyl, alkenyl, aralkyl, arylalkenyl, heteroarylalkyl, heteroarylalkenyl, hydroxyalkyl, aminoalkyl, aryl, thioalkyl, alkoxyalkyl or alkylaminoalkyl; and
$R^{54}$ is selected from the group consisting of hydrogen; alkyl; fluoroalkyl; difluoroalkyl; trifluoroalkyl; cycloalkyl; cycloalkyl substituted by 1 to 3 substituents selected from the group consisting of alkoxyalkyl, alkyl, halogen, hydroxy, alkoxy, aryloxy, arylalkoxy, —$NR^1R^2$, —$NR^1C(O)R^2$, —$NR^1C(O)NR^1R^2$, —$NR^1C(O)OR^2$, —$NR^1S(O)_2R^2$, —$NR^1S(O)_2NR^1R^2$, —C(O)OH, —$C(O)OR^1$ and —$CONR^1R^2$; alkenyl; alkoxy; arylalkyl; arylalkenyl; heteroarylalkyl; heteroarylalkenyl; hydroxy; alkoxy; hydroxyalkyl; alkoxyalkyl; aminoalkyl; aryl; heteroaryl; thioalkyl and alkyl substituted by 1 to 3 subsituents selected from the group consisting of urea, sulfonamide, carboxamide, carboxylic acid, carboxylic ester and sulfonyl urea; and pharmaceutically acceptable salts thereof.

2. A compound of claim 1 wherein A is O.

3. A compound of claim 2 wherein for $A_n$, n is 1 and $M_n$ is absent, wherein a compound of formula I has the following structure:

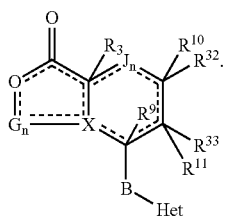

formula I

4. A compound of claim 1 wherein G is —$CR^1R^2$—.

5. A compound of claim 1 wherein $R^1$ and $R^2$ are hydrogen.

6. A compound of claim 1 wherein J is —$CR^1R^2$—.

7. A compound of claim 1 wherein $R^1$ is hydrogen and $R^2$ is methyl.

8. A compound of claim 1 wherein for $J_n$, n is 1.

9. A compound of claim 1 wherein $A_n$ is oxygen, G is —CH(Me), and $M_n$ is absent wherein a compound of formula I has the following structure:

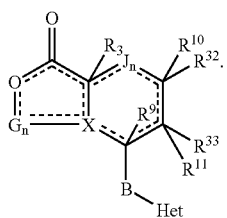

formula I

10. A compound of claim 1 wherein X is CH.

11. A compound of claim 1 wherein B is —$(CH_2)_{n4}CR^{12}$=$CR^{12a}(CH_2)_{n5}$—, where $_{n4}$ and $_{n5}$ are 0.

12. A compound of claim 1 wherein $R^3$ is —$C(O)NR^{18}R^{19}$.

13. A compound of claim 1 wherein $R^{18}$ and $R^{19}$ are hydrogen, alkyl, heteroaryl,
—C(NH)—$NH_2$, aryl, $R^{21}$-aryl, or alkyl substituted with one or two moieties selected from cycloalkyl, halogen, hydroxy, —$NR^1R^2$, —$NR^1C(O)R^2$, —$NR^1C(O)NR^1R^2$, —$NR^1C(O)OR^2$,
—$NR^1S(O)_2R^2$, —$NR^1S(O)_2NR^1R^2$, —C(O)OH, —C(O)OR^1$ or —C(O)NR^1R^2$; where $R^1$ and $R^2$ are hydrogen, alkyl or alkoxy; or $R^{18}$ and $R^{19}$ together with the nitrogen to which they are attached, form a mono or bicyclic heterocyclic ring of 4 to 10 atoms, with 1-3 heteroatoms selected from O, N, S, S(O), S(O)$_2$ and C=O, with the proviso that the S or O atom are not adjacent to each other, unsubstituted or substituted with one or more groups selected from alkyl, halogen, hydroxy, alkoxy, aryloxy, arylalkoxy, —$NR^1R^2$, —$NR^1COR^2$,
—$NR^1C(O)NR^1R^2$, —$NR^1C(O)OR^2$, —$NR^1S(O)_2R^2$, —$NR^1S(O_2)NR^1R^2$, —C(O)OH,
—C(O)OR^1$, —CONR^1R^2$ and alkyl optionally substituted with —$NR^1R^2$, —$NR^1COR^2$, —$NR^1CONR^1R^2$,
—$NR^1C(O)OR^2$, —$NR^1S(O)_2R^2$, —$NR^1S(O)_2NR^1R^2$, —C(O)OH, —C(O)OR^1$ or —CONR^1R^2$.

14. A compound of claim 1 wherein Het is pyridyl attached to B by a ring carbon and is substituted by 1 to 2 substituents selected from $R^{21}$-phenyl and $R^{21}$-pyridyl.

15. A compound of claim 1 wherein W is aryl, heteroaryl or aryl substituted by halogen or —CN.

16. A compound of claim 1 wherein $R^{32}$ and $R^{33}$ are hydrogen or alkyl.

17. A compound of claim 1 wherein

B is cis or trans —$(CH_2)_{n4}CR^2$=$CR^{12a}(CH_2)_{n5}$-, where $n_4$ and $n^5$ are 0;

$A_n$ is O where n is 1;

$G_n$ is $CH_2$, CH(alkyl) or C(alkyl)$_2$;

X is —CH—;

$J_n$ is $CH_2$ where n is 1;

$R^3$ is —$C(O)NR^{18}R^{19}$;

$R^{10}$ and $R^{11}$ are hydrogen;

$R^{18}$ and $R^{19}$ are hydrogen, alkyl, heteroaryl, —C(NH)—$NH_2$, aryl, $R^{21}$-aryl, or alkyl substituted with one or two moieties selected from cycloalkyl, halogen, hydroxy,
—$NR^1R^2$, —$NR^1C(O)R^2$, —$NR^1C(O)NR^1R^2$, —$NR^1C(O)OR^2$, —$NR^1S(O)_2R^2$, —$NR^1S(O)_2NR^1R^2$, —C(O)OH, —C(O)OR^1$ or —C(O)NR^1R^2$; where $R^1$ and $R^2$ are hydrogen, alkyl or alkoxy; or $R^{18}$ and $R^{19}$ together with the nitrogen to which they are attached, form a mono or bicyclic heterocyclic ring of 4 to 10 atoms, with 1-3 heteroatoms selected from O, N, S, S(O), S(O)$_2$ and C=O, with the proviso that the S or O atom are not adjacent to each other, unsubstituted or substituted with one or more groups selected from alkyl, halogen, hydroxy, alkoxy, aryloxy, arylalkoxy, —$NR^1R^2$, —$NR^1COR^2$,
—$NR^1C(O)NR^1R^2$, —$NR^1C(O)OR^2$, —$NR^1S(O)_2R^2$, —$NR^1S(O_2)NR^1R^2$, —C(O)OH, —C(O)OR^1$, —CONR^1R^2$ and alkyl optionally substituted with —$NR^1R^2$, —$NR^1COR^2$, —$NR^1CONR^1R^2$,
—$NR^1C(O)OR^2$, —$NR^1S(O)_2R^2$, —$NR^1S(O)_2NR^1R^2$, —C(O)OH, —C(O)OR^1$ or —CONR^1R^2$;

Het is pyridyl;

W is phenyl or heteroaryl wherein said phenyl or heteroaryl substituted with the following moieties, halogen, —CN, —$CF_3$, OH, O-alkyl, —$SO_2NR^4R^5$, or —$CONR^4R^5$, or two adjacent moieties form a fused methylene dioxy ring with the carbons to which they attached; and $R^{32}$ and $R^{33}$ are hydrogen or alkyl.

18. The compound of claim 17 wherein $R^3$, $R^{32}$, $R^{33}$ and W are defined as follows:

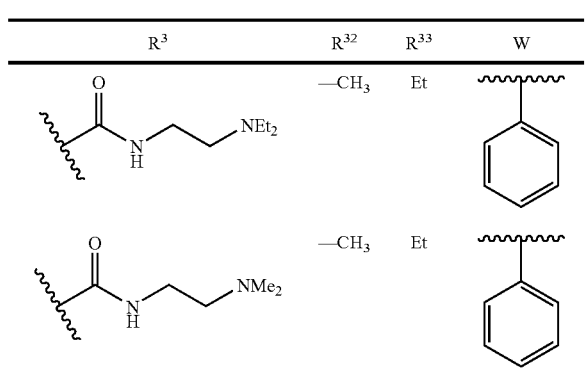

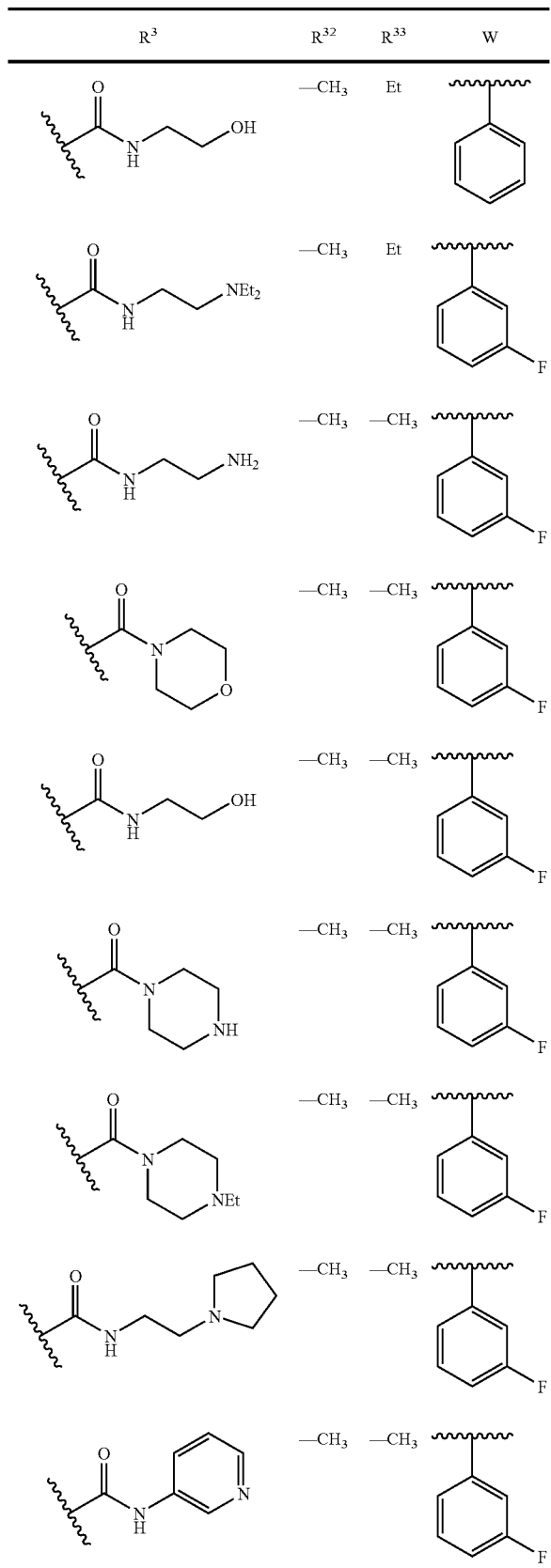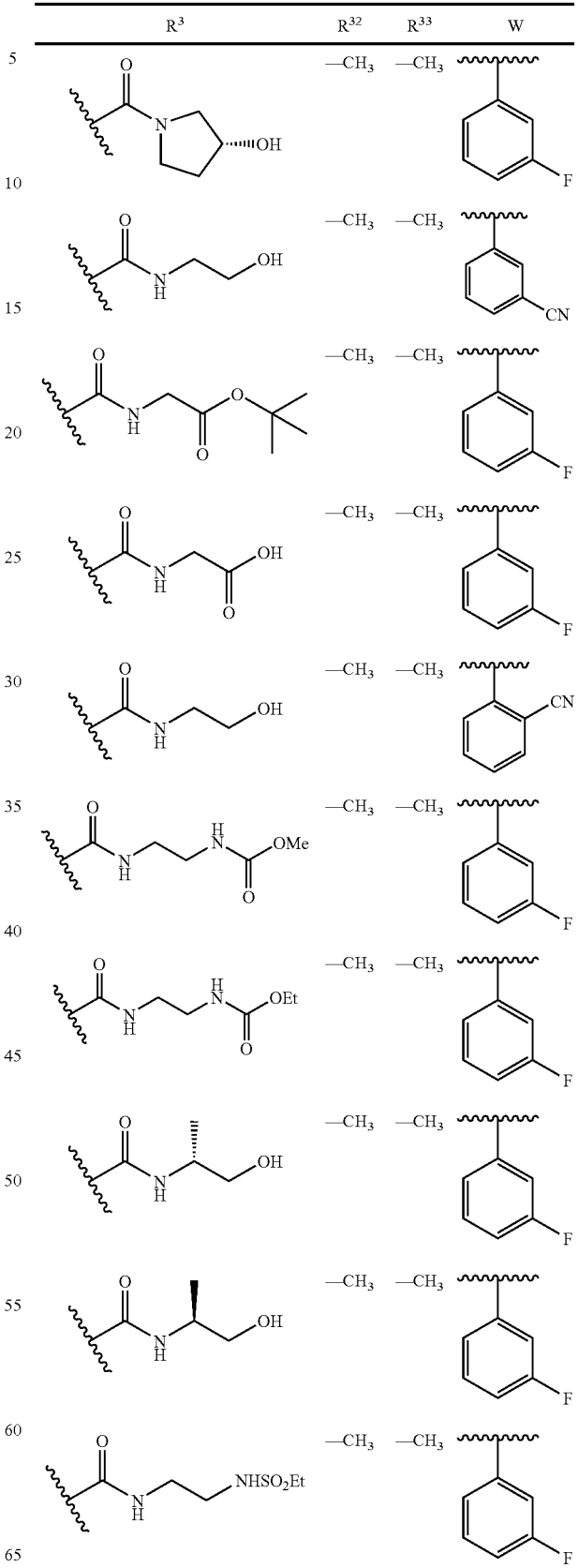

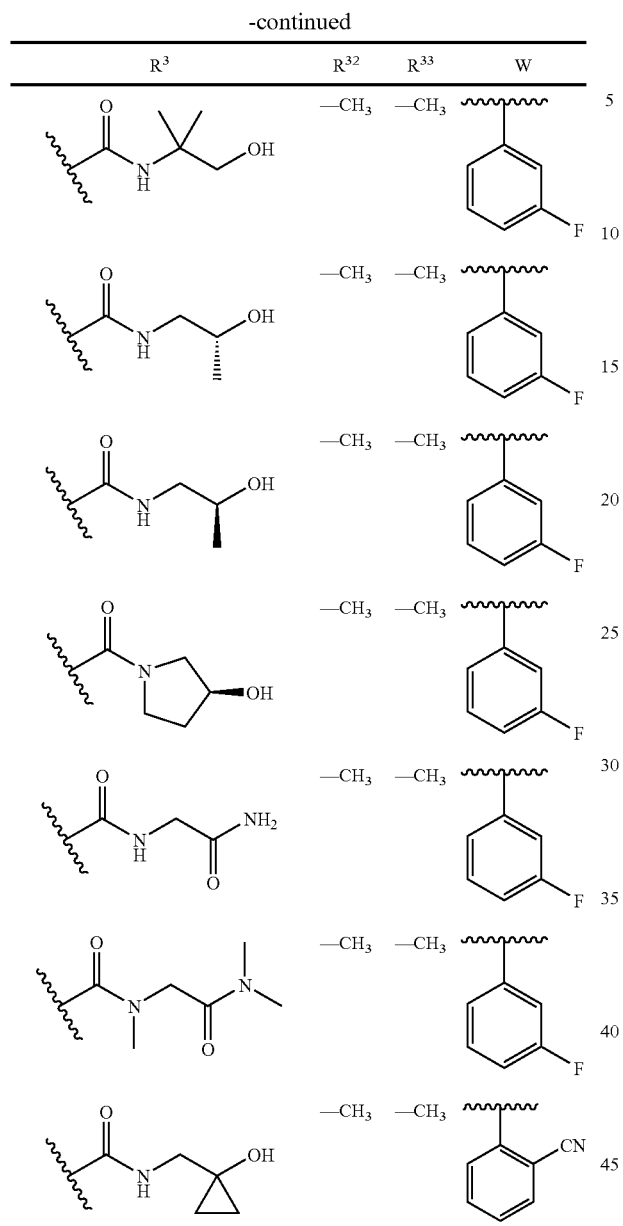
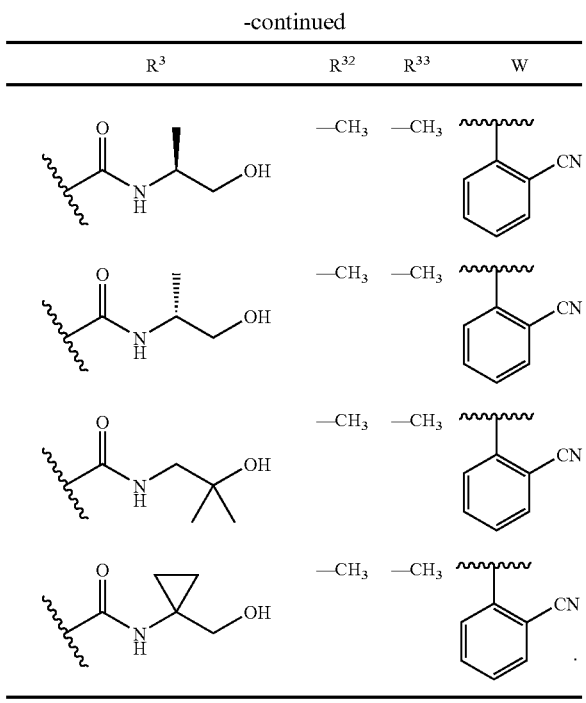
19. The compound of claim 1 with the following structure
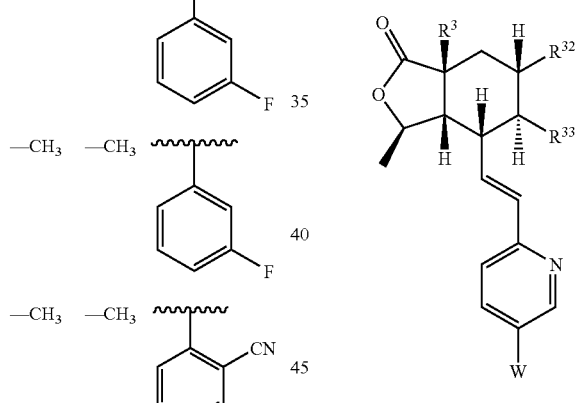
wherein W, R³, R³² and R³³ are defined as follows:
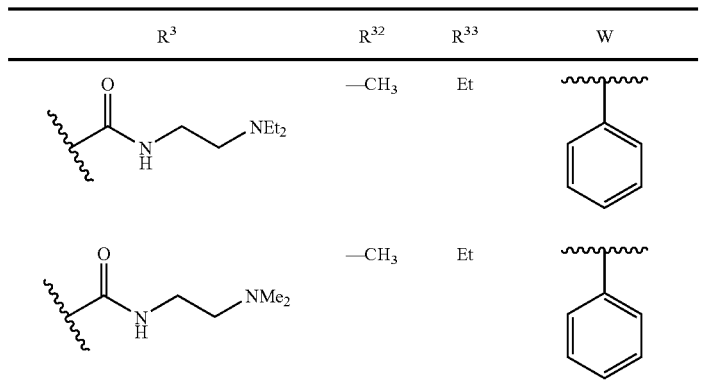

-continued
| R³ | R³² | R³³ | W |
|---|---|---|---|
| 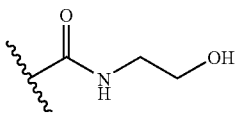 | —CH₃ | Et | 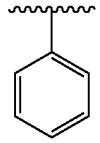 |
| 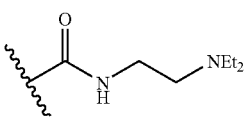 | —CH₃ | Et | 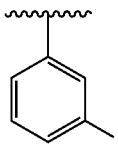 |
| 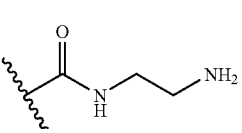 | —CH₃ | —CH₃ | 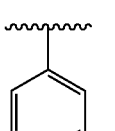 |
| 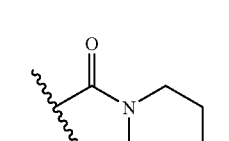 | —CH₃ | —CH₃ | 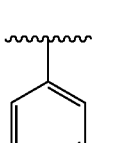 |
| 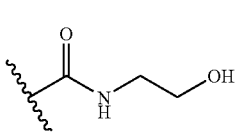 | —CH₃ | —CH₃ | 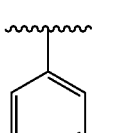 |
| 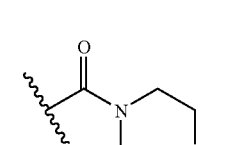 | —CH₃ | —CH₃ | 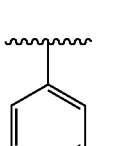 |
| 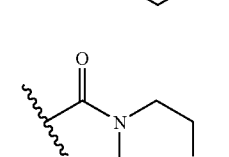 | —CH₃ | —CH₃ | 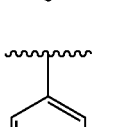 |
| 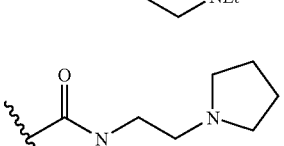 | —CH₃ | —CH₃ |  |
| 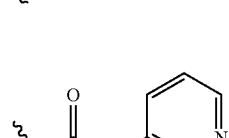 | —CH₃ | —CH₃ |  |

-continued

| R³ | R³² | R³³ | W |
|---|---|---|---|
| (pyrrolidine with OH, acylated) | —CH₃ | —CH₃ | 3-F-phenyl |
| —C(O)NH-CH₂CH₂-OH | —CH₃ | —CH₃ | 3-CN-phenyl |
| —C(O)NH-CH₂-C(O)O-tBu | —CH₃ | —CH₃ | 3-F-phenyl |
| —C(O)NH-CH₂-COOH | —CH₃ | —CH₃ | 3-F-phenyl |
| —C(O)NH-CH₂CH₂-OH | —CH₃ | —CH₃ | 2-CN-phenyl |
| —C(O)NH-CH₂CH₂-NHC(O)OMe | —CH₃ | —CH₃ | 3-F-phenyl |
| —C(O)NH-CH₂CH₂-NHC(O)OEt | —CH₃ | —CH₃ | 3-F-phenyl |
| —C(O)NH-CH(CH₃)-CH₂OH (S) | —CH₃ | —CH₃ | 3-F-phenyl |
| —C(O)NH-CH(CH₃)-CH₂OH (R) | —CH₃ | —CH₃ | 3-F-phenyl |
| —C(O)NH-CH₂CH₂-NHSO₂Et | —CH₃ | —CH₃ | 3-F-phenyl |

-continued

| R³ | R³² | R³³ | W |
|---|---|---|---|
| (amide with -NH-C(CH₃)₂-CH₂OH) | —CH₃ | —CH₃ | 3-F-phenyl |
| (amide with -NH-CH₂-CH(OH)-CH₃) | —CH₃ | —CH₃ | 3-F-phenyl |
| (amide with -NH-CH₂-CH(OH)-CH₃, opposite stereo) | —CH₃ | —CH₃ | 3-F-phenyl |
| (acyl pyrrolidine with 3-OH) | —CH₃ | —CH₃ | 3-F-phenyl |
| (amide with -NH-CH₂-C(O)NH₂) | —CH₃ | —CH₃ | 3-F-phenyl |
| (amide with -N(CH₃)-CH₂-C(O)N(CH₃)₂) | —CH₃ | —CH₃ | 3-F-phenyl |
| (amide with -NH-CH₂-C(OH)(cyclopropyl)) | —CH₃ | —CH₃ | 2-CN-phenyl |
| (amide with -NH-CH(CH₃)-CH₂OH) | —CH₃ | —CH₃ | 2-CN-phenyl |
| (amide with -NH-CH(CH₃)-CH₂OH, opposite stereo) | —CH₃ | —CH₃ | 2-CN-phenyl |
| (amide with -NH-CH₂-C(CH₃)₂-OH) | —CH₃ | —CH₃ | 2-CN-phenyl |

-continued

| R³ | R³² | R³³ | W |
|---|---|---|---|
| 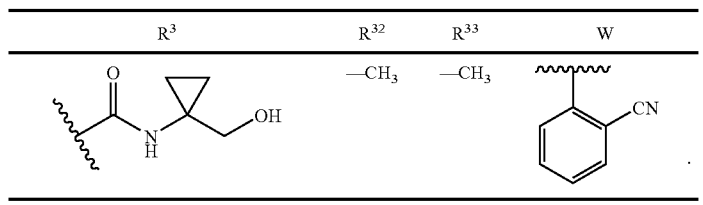 | —CH₃ | —CH₃ | 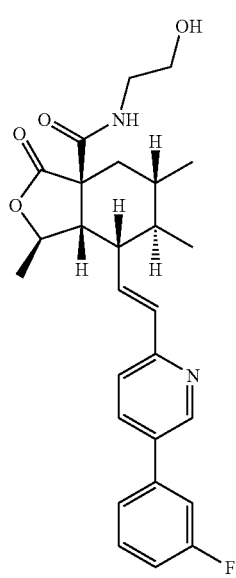 |

20. A compound of claim 1 with the following formulae:

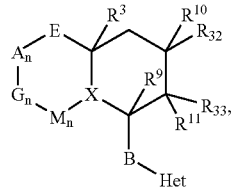

where X is —CH—.

21. A pharmaceutical composition comprising an effective amount of a compound of claim 1 and a pharmaceutically acceptable carrier.

22. A compound of claim 1 in purified form.

23. A compound of claim 1 in isolated form.

24. A compound of claim 1 with the following formulae:

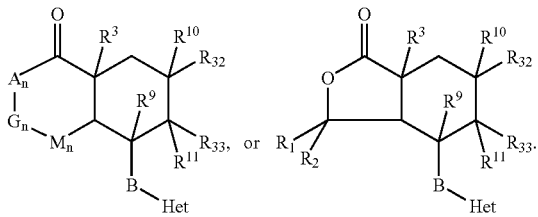

25. The compound of claim 1 that has the formula

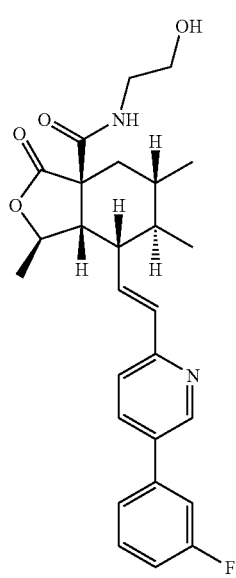

or pharmaceutically acceptable salt thereof.

* * * * *

UNITED STATES PATENT AND TRADEMARK OFFICE
CERTIFICATE OF CORRECTION

PATENT NO. : 7,488,752 B2
APPLICATION NO. : 11/243708
DATED : February 10, 2009
INVENTOR(S) : Chackalamannil et al.

It is certified that error appears in the above-identified patent and that said Letters Patent is hereby corrected as shown below:

Delete Title Page, and Replace with Title Page. (Attached)

In the Claims:

Claim 1, Col. 107, Line 1: Please correct "-$S^{13}$" to --$S(O)_2R^{13}$--

Claim 2: Please delete, entire claim and Renumber Claims 3-25 to 2-24

Signed and Sealed this

Thirtieth Day of June, 2009

JOHN DOLL
*Acting Director of the United States Patent and Trademark Office*

United States Patent
Chackalamannil et al.

(10) Patent No.: US 7,488,752 B2
(45) Date of Patent: Feb. 10, 2009

(54) THROMBIN RECEPTOR ANTAGONISTS

(75) Inventors: Samuel Chackalamannil, Califon, NJ (US); Mariappan V. Chelliah, Edison, NJ (US); Yan Xia, Edison, NJ (US); Keith A. Eagen, West Orange, NJ (US)

(73) Assignee: Schering Corporation, Kenilworth, NJ (US)

( * ) Notice: Subject to any disclaimer, the term of this patent is extended or adjusted under 35 U.S.C. 154(b) by 377 days.

(21) Appl. No.: 11/243,708

(22) Filed: Oct. 5, 2005

(65) Prior Publication Data
US 2006/0079684 A1    Apr. 13, 2006

Related U.S. Application Data

(60) Provisional application No. 60/617,514, filed on Oct. 8, 2004.

(51) Int. Cl.
*A01N 43/08* (2006.01)
*A61K 31/34* (2006.01)
*C07D 307/00* (2006.01)
*C07D 307/93* (2006.01)
*C07D 407/00* (2006.01)

(52) U.S. Cl. .................................... 514/469; 549/302
(58) Field of Classification Search ................. 549/302; 514/469
See application file for complete search history.

(56) References Cited

U.S. PATENT DOCUMENTS

| | | |
|---|---|---|
| 6,063,847 A | 5/2000 | Chackalamannil et al. |
| 6,326,380 B1 | 12/2001 | Chackalamannil et al. |
| 6,645,987 B2 | 11/2003 | Chackalamannil et al. |
| 7,037,920 B2 | 5/2006 | Chackalamannil et al. |
| 2004/0152736 A1 | 8/2004 | Chackalamannil et al. |

FOREIGN PATENT DOCUMENTS

| | | |
|---|---|---|
| WO | 0196330 | * 12/2001 |
| WO | WO 01/96330 A2 | 12/2001 |

OTHER PUBLICATIONS

Bensaid et al., "The Cannabinoid $CB_1$ Receptor Antagonist SR 141716 Increases Acrp30 mRNA Expression in Adipose Tissue of Obese fa/fa Rats and in Cultured Adipocyte Cells", Molecular Pharmacology, 63(4):908-914 (2003).
Bernatowicz et al., "Development of Potent Thrombin Receptor Antagonist Peptides", *J. Med. Chem.*, 39:4879-4887 (1996).
Chackalamannil, "A Highly Efficient Total Synthesis of (+)-Himbacine", *J. Am. Chem. Soc.*, 118:9812-9813 (1996).
Pertwee, "Pharmacology of Cannabinoid Receptor Ligands", *Current Medicinal Chemistry*, 6(8):635-664 (1999).
Wermuth, "Molecular Variations Based on Isosteric Replacements", *The Practice of Medicinal Chemistry*, pp. 203-237 (1996).
International Search Report for corresponding PCT Application No. PCT/US2005/035745 International Filing Date Jul. 19, 2006.

* cited by examiner

*Primary Examiner*—D. Margaret Seaman
*Assistant Examiner*—Niloofar Rahmani
(74) *Attorney, Agent, or Firm*—William Y. Lee; Serena Farquharson-Torres

(57) ABSTRACT

Heterocyclic-substituted tricyclics of the formula

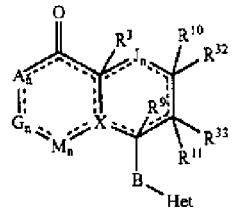

formula I or a pharmaceutically acceptable salt or solvate of said compound, isomer or racemic mixture wherein $z,1$ represents an optional double bond, the dotted line is optionally a bond or no bond, resulting in a double bond or a single bond, as permitted by the valency requirement and wherein A, B, G, M, X, J, n, Het, $R^3$, $R^{10}$, $R^{11}$, $R^{32}$ and $R^{33}$ are herein defined and the remaining substituents are as defined in the specification, are disclosed, as well as pharmaceutical compositions containing them and a method of treating diseases associated with thrombosis, atherosclerosis, restenosis, hypertension, angina pectoris, arrhythmia, heart failure, and cancer by administering said compounds. Combination therapy with other cardiovascular agents is also claimed.

24 Claims, No Drawings